United States Patent
Meksem et al.

(10) Patent No.: US 12,270,039 B2
(45) Date of Patent: Apr. 8, 2025

(54) COMPOSITIONS AND METHODS TO INCREASE OLEIC ACID CONTENT IN SOYBEANS

(71) Applicant: Board of Trustees of Southern Illinois University, Carbondale, IL (US)

(72) Inventors: Khalid Meksem, Carbondale, IL (US); Naoufal Lakhssassi, Carbondale, IL (US); Dounya Knizia, Carbondale, IL (US)

(73) Assignee: Board of Trustees of Southern Illinois University, Carbondale, IL (US)

( * ) Notice: Subject to any disclaimer, the term of this patent is extended or adjusted under 35 U.S.C. 154(b) by 178 days.

(21) Appl. No.: 17/745,148

(22) Filed: May 16, 2022

(65) Prior Publication Data

US 2022/0364106 A1    Nov. 17, 2022

Related U.S. Application Data

(60) Provisional application No. 63/188,993, filed on May 14, 2021.

(51) Int. Cl.
   *C12N 15/82*     (2006.01)
(52) U.S. Cl.
   CPC ............................. *C12N 15/8247* (2013.01)
(58) Field of Classification Search
   CPC combination set(s) only.
   See application file for complete search history.

(56) References Cited

U.S. PATENT DOCUMENTS

| | | | |
|---|---|---|---|
| 2012/0246748 A1 * | 9/2012 | Guo ................... | C12N 15/8275 536/23.6 |
| 2017/0367383 A1 * | 12/2017 | Esquivel ................. | A23L 13/60 |
| 2018/0028512 A1 * | 2/2018 | Lee .......................... | A61P 13/02 |
| 2018/0094234 A1 * | 4/2018 | Lyte .......................... | C12N 1/20 |

FOREIGN PATENT DOCUMENTS

| | | | | |
|---|---|---|---|---|
| AU | 2004200281 A1 | 2/2004 | | |
| CN | 111073904 A | * | 4/2020 | ........... C07K 14/415 |
| WO | WO-2019173125 A1 | * | 9/2019 | ......... C12N 15/8213 |

OTHER PUBLICATIONS

Nachtschatt et al., European Journal of Lipid Science and Technology 122.12 (2020): 2000181 (Year: 2020).*
Lakhssassi, et al., Cells 10.5 (2021): 1245 (Year: 2021).*
Yeom et al., Frontiers in Plant Science 10 (2020): 496713; (Year: 2020).*
Lakhssassi et al., Frontiers in Plant Science 8 (2017): 246749 (Year: 2017).*
Haun, et al., Plant biotechnology journal 12.7 (2014): 934-940 (Year: 2014).*
Zrimec et al. Nature communications 13.1 (2022): 5099 (Year: 2022).*
Benfey and Chua, 1990, The Cauliflower Mosaic Virus 35S Promoter: Combinatorial Regulation of Transcription in Plants, Science 250: 959-966. (Year: 1990).*
Morton et al., 2014, Paired-End Analysis of Transcription Start Sites in *Arabidopsis* Reveals Plant-Specific Promoter Signatures, The Plant Cell 26: 2746-2760. (Year: 2014).*
Dutt et al., 2014, Temporal and Spatial Control of Gene Expression in Horticultural Crops, Horticulture Research 1, 14047: 1-17. (Year: 2014).*
Amin, N. et al., CRISPR-Cas9 Mediated Targeted Disruption of FAD2-2 Microsomal Omega-6 Desaturase in Soybean (*Glycine max*.L), 2019, BMC Biotechnology, 19:9, 10 pages.
Alfonso, M., "Improving Soybean Seed Oil Without Poor Agronomics," 2020, J Exp Botany, 71/22:6856-6860, 4 pages.
Almeida, D.M., et al., "Regulation of Na+ and K+ Homeostatis in Plants: Towards Improved Salt Stress Tolerance in Crop Plants," 2017, Genet Mol Biol, 40/1 (suppl): 326-345, 20 pages.
Anai, T., et al., "Two High-Oleic-Acid Soybean Mutants, M23 and KK21, Have Disrupted Microsomal Omega-6 Fatty Acid Desaturase, Encoded by GmFAD2-1a," 2008, Breeding Science, 58:447-452, 6 pages.
Anders, S., et al., "HTSeq-a Python Framework to Work with High-Througput Sequencing Data," 2015, Bioinformatics, 31/2:166-169, 4 pages.
Ascherio, A., et al., "Health Effects of Trans Fatty Acids," 1997, Am J Clin Nutr, 66(suppl):1006S-1010S, 5 pages.
Bachleda, N., et al., "Effects of High Oleic Acid Soybean on Seed Yield, Protein and Oil Contents, and Seed Germination Revealed by Near-Isogeneic Lines," 2017, Plant Breeding, 136:539-547, 9 pages.
Bansal, V., "A Statistical Method for the Detection of Variants from Next-Generation Resequencing of DNA Pools," 2010, Bioinformatics, 26:i318-i324, 7 pages.
Bolger, A.M., et al., "Trimmomatic: A Flexible Trimmer of Illumina Sequence Data," 2014, Bioinformatics, 30:2114-2120, 7 pages.
Buhr, T., et al., "Ribozyme Termination of RNA Transcripts Down-Regulate Seed Fatty Acid Genes in Transgenic Soybean," 2002, The Plant J, 30/2:155-163, 9 pages.

(Continued)

*Primary Examiner* — Bratislav Stankovic
(74) *Attorney, Agent, or Firm* — Stinson LLP

(57) ABSTRACT

The present invention is directed to a transgenic soybean plant with increased oleic acid content comprising a polynucleotide encoding a fatty acid desaturase (FAD) related promoter that functions in the soybean plant operably linked to a polynucleotide encoding a polypeptide having FAD activity. The invention is also related to a plant of an agronomically elite soybean variety with increased oleic acid content comprising a polynucleotide encoding a fatty acid desaturase (FAD) related promoter that functions in the soybean plant operably linked to a polynucleotide encoding a polypeptide having FAD activity. The invention is still further directed to a method of increasing the oleic acid content of a soybean plant comprising transforming the soybean plant with a polynucleotide encoding a fatty acid desaturase (FAD) related promoter that functions in the soybean plant operably linked to a polynucleotide encoding a polypeptide having FAD activity.

5 Claims, 26 Drawing Sheets
(8 of 26 Drawing Sheet(s) Filed in Color)
Specification includes a Sequence Listing.

(56) References Cited

OTHER PUBLICATIONS

Cahoon, E.B., et al., "Biosynthetic Origin of Conjugated Double Bonds: Production of Fatty Acid Components of High-Value Drying Oils in Transgenic Soybean Embryos," 1999, PNAS, 96/22:12935-12940, 6 pages.

Cahoon, E.B., et al., "Dimorphecolic Acid is Synthesized by the Coordinate Activities of Two Divergent Delta12-Oleic Acid Desaturases," 2004, J Biolog Chem, 279/13:12495-12502, 8 pages.

Cartharius, K., "MatInspector and Beyond: Promoter Analysis Based on Transcription Factor Binding Sites," 2005, Bioinformatics, 21/13:2933-2942, 10 pages.

Chang, W-C., et al., "PlantPAN: Plant Promoter Analysis Navigator, for Identifying Combinatorial cis-Regulatory Elements with Distance Constraint in Plant Gene Groups," 2008, BMC Genomics, 9/56, 14 pages.

Chen, X., et al., "Genome-wide Analysis of Soybean HD-Zip Gene Family and Expression Profiling under Salinity and Drought Treatments," 2014, POLS One, 9/2:e87156, 17 pages.

Clark, K.J., et al., "Determination of the Optimal Ratio of Linoleic Acid to alpha-Linolenic Acid in Infant Formulas," 1992, J Pediatrics, S151-S158, 8 pages.

Cooper, J.L., et al., "TILLING to Detect Induced Mutations in Soybeans," 2008, BMC Plant Biology, 8/9, 10 pages.

Danecek, P., et al., "The Varian Call Format and VCFtools," 2011, Bioinformatics, 27/15:2156-2158, 3 pages.

Dierking, E.C., et al., "New Sources of Soybean Seen Meal and Oil Composition Traits Identified Through Tilling," 2009, BMC Plant Biology, 9:89, 11 pages.

Dobin, A., et al., "Mapping RNA-seq Reads with STAR," 2015, Curr Protoc Bioinformatics, 51, 23 pages.

Dong, C-J., et al., "Characterization of the Fatty Acid Desaturase Genes in Cucumber: Structure, Phylogeny, and Expression Patterns," 2016, PLoS One, 11/3:e0149917, 22 pages.

Dyer, J.M., et al., "Immunocytological Localization of Two Plant Fatty Acid Desaturases in the Endoplasmic Reticulum," 2001, FEBS Letters, 494:44-47, 4 pages.

Dyer, J.M., et al., "Molecular Analysis of a Bifunctional Fatty Acid Conjugase/Desaturase from Tung. Implications for the Evolution of Plant Fatty Acid Divesity," 2002, Plant Physiol, 130:2027-2038, 12 pages.

Eckardt, N.A., "Two Genomes are Better than One: Widespread Paleopolyploidy in Plants and Evolutionary Effects," 2004, The Plant Cell, 16:1647-1649, 3 pages.

Fehr, W.R., "Breeding for Modified Fatty Acid Composition in Soybean," 2007, Crop Sci, 47/S3:S72-S87, 16 pages.

Finn, R.D., "Pfam: The Protein Families Database," 2014, Nucl Acid Res, 42:D222-D230, 9 pages.

Garrison, E., et al. "Haplotype-based Variant Detection from Short-Read Sequencing," 2012, arXiv:1207.3907v2 [q-bio.GN], 9 pages.

Haun, W., et al., "Improved Soybean Oil Quality by Tageted Mutagenesis of the Fatty Acid Desaurase 2 Gene Family," 2014, Plant Biotech J, 12:934-940, 7 pages.

Heffner, E.L., et al., "Genomic Selection for Crop Improvement," 2009, Crop Sci, 49, 12 pages.

Hewezi, T., et al., "*Arabidopsis* Spermidine Synthase is Targeted by an Effector Protein of the Cyst Nematode," 2010, Plant Physiol, 152:968-984, 17 pages.

Higo, K., et al., "Plant cis-Acting Regulatory DNA Elements (Place) Database: 1999," 1999, Nucl Acids Res, 27/1:297-300, 4 pages.

Hoshino, T., et al., "Novel GmFAD2-1b Mutant Alleles Created by Reverse Genetics Induce Marked Elevation of Oleic Acid Content in Soybean Seeds in Combination with GmFAD2-1a Mutant Alleles," 2010, Breeding Science, 60:419-425, 7 pages.

Javell, M., et al., "Overexpression of the Epidermis-Specific Homeodomain-Leucine Zipper IV Transcription Factor Outer Cell Layer1 in Maize Identifies Target Genes Involved in Lipid Metabolism and Cuticle Biosynthesis," 2010, Plant Physiol, 154:273-287, 14 pages.

Juretic, N., et al., "The Evolutionary Fate of Mule-mediated Duplications of Host Gene Fragments in Rice," 2005, Genome Research, 15:1292-1297, 6 pages.

Kavithamani, D., et al., "Deveopment of New Vegetable Soybean (*Glycine max* L. Merill) Mutants with High Protein and Less Fibre Content," 2010, J Plant Breeding, 1/4:1060-1065, 6 pages.

Kelley, L.A., et al., "The Phyre2 Web Portal for Protein Modeling, Prediction and Analysis," 2015, Nature Protocols, 10/6:845-858, 14 pages.

Kramer, J.K.G., et al., "Evaluating Acid and Base Catalysts in the Methylation of Milk and Rumen Fatty Acids with Special Emphasis on Conjugated Dienes and Total trans Fatty Acids," 1997, Lipids, 32/11:1219-1228, 10 pages.

Lakhssassi, N., et al., "Characterization of the FAD2 Gene Family in Soybean Reveals the Limitations of Gel-based Tilling in Genes with High Copy Number," 2017, Frontiers in Plant Science, vol. 8, Art. 324, 15 pages.

Lakhssassi, N., et al., "Stearoyl-Acyl Carrier Protein Desaturase Mutations Uncover an Impact of Stearic Acid in Leaf and Nodule Structure," 2017, Plant Physiol, 174:1531-1543, 13 pages.

Lakhssassi, N., et al., "Characterization of the Soluble NSF Attachment Protein Gene Family Identifies Two Members Involved in Additive Resistance to a Plant Pathogen," 2017, Sci Rep, 7:45226, 11 pages.

Lakhssassi, N., et al., "Soybean Tilling-by-Sequencing+ Reveals the Role of Novel GmSACPD Members in Unsaturated Fatty Acid Biosynthesis While Maintaining Healthy Nodules," 2020, J Exp Bot, 71/22:6969-6987, 19 pages.

Lakhssassi, N., et al., "Tilling-by-Sequencing+ Reveals the Role of Novel Fatty Acid Desaturses (GmFAD2-2s) in Increasing Soybean Seed Oleic Acid Content," 2021, Cells, 10:1245, 20 pages.

Lakhssassi, N., et al., "Tilling-by-Sequencing+ to Decipher Oil Biosynthesis Pathway in Soybeans: A New and Effective Platform for High-Throughput Gene Functional Analysis," 2021, Int J Mol Sci, 22:4219, 21 pages.

Li,W-H., et al., "Pseudogenes as a Paradigm of Neutral Evolution," 1981, Nature, 262:237-239, 3 pages.

Li, H., et al., "Fast and Accurate Short Read Alignment with Burrows-Wheeler Transform," 2009, Bioinformatics, 25/14:1754-1760, 7 pages.

Li, H., et al., "The Sequence Alignment/Map Format and SAMtools," 2009, Bioinformatics, 25/16:2078-2079, 2 pages.

Liu, J., et al., "Soybean Kinome: Functional Classification and Gene Expression Patterns," 2015, J Exp Bot, 66/7:1919-1934, 16 pages.

Love, M.I., "Moderated Estimation of Fold Change and Dispersion for RNA-seq Data with DESeq2," 2014, Genome Biol, 15:550, 21 pages.

Marchler-Bauer, A., et al., CDD: NCBI's Conserved Domain Database, 2015, Nucl Acids Res, 43:D222-D226, 5 pages.

Miao, X., et al., Cloning and Functional Analysis of the FAD2 Gene Family from Desert Shrub Artemisia sphaerocephala, 2019, BMC Plant Biol, 19:481, 13 pages.

O'Keefe, S.F., et al., "Comparison of Oxidative Stability of High- and Normal-Oleic Peanut Oils," 1993, JAOCS, 70/5:489-492, 4 pages.

Pettersen, E.F., et al., "UCSF Chimera—A Visualization System for Exploratory Research and Analysis," 2004, J Comput Chem, 25:1605-1612, 8 pages.

Pham, A-T., et al., "Mutant Alleles of FAD1-1A and FAD2-1B Combine to Produce Soybeans with the High Oleic Acid Seed Oil Trait," 2010, BMC Plant Biol, 10:195, 13 pages.

Pham, A-T., et al., "A Novel FAD2-1 A Allele in a Soybean Plant Introduction Offers an Alternate Means to Produce Soybean Seed Oil with 85% Oleic Acid Content," 2011, Theor Appl Genet, 123:793-802, 10 pages.

Pham, A-T., et al., "Combinations of Mutant FAD2 and FAD3 Genes to Produce High Oleic Acid and Low Linolenic Acid Soybean Oil," 2012, Theor Appl Genet, 125:503-515, 13 pages.

Raneses, A.R., et al., "Potential Biodiesel Markets and Their Economic Effects on the Agricultural Sector of the United States," 1999, Industrial Crops and Products, 9:151-162, 12 pages.

Robinson, J.T., et al., "Integrative Genomics Viewer," 2011, Nat Biotechnol, 29/1:24-26, 6 pages.

(56) References Cited

OTHER PUBLICATIONS

Roman, A., et al., "Contribution of the Different Omega-3 Fatty Acid Desaturase Genes to the Cold Response in Soybean," 2012, J Exp Bot, 63/13:4973-4982, 10 pages.

Sahari, M.A., et al., "Characteristics of Tea Seed Oil in Comparison with Sunflower and Olive Oils and its Effect as a Natural Antioxidant," 2004, JAOCS, 81:585-588, 4 pages.

Saitou, N., et al., "The Neighbor-joining Method: A New Method for Reconstructing Phylogenetic Trees," 1987, Mol Biol Evol, 4/4:406-425, 20 pages.

Schmutz, J., et al., "Genome Sequence of the Palaeopolyploid Soybean," 2010, Nature, 463:178-183, 6 pages.

Su, M.H., et al., "Chemical Composition of Seed Oils in Native Taiwanese *Camellia* Species," 2014, Food Chem, 156:369-373, 5 pages.

Tamura, K., et al., "MEGA6: Molecular Evolutionary Genetics Analysis Version 6.0," 2013, Mol Biol Evol, 30/12:2725-2729, 5 pages.

Tang, G-Q., et al., "Oleate Desaturase Enzymes of Soybean: Evidence of Regulation Through Differential Stability and Phosphorylation," 2005, The Plant J, 44:433-446, 14 pages.

Taylor, D.C., et al., "Field Testing of Transgenic Rapeseed cv. Hero Transformed with a Yeast sn-2 Acyltransferase Results in Increased Oil Content, Erucic Acid Content and Seed Yield," 2001, Molec Breeding, 8:317-322, 6 pages.

Todorova, R., "Expression and Localization of FAD2 Desaturase from Spinach in Tobacco Cells," 2008, Russian J Plant Physiol, 55/4:513-520, 8 pages.

Trapnell, C., et al., "TopHat: Discovering Splice Junctions with RNA-Seq," 2009, Bioinformatics, 25/9:1105-1111, 7 pages.

Walsh, T.A., et al., "Canola Engineered with a Microalgal Polyketide Synthase-like System Produces Oil Enriched in Docosahexaenoic Acid," 2016, Nature Biotech, 34/8:881-889, 9 pages.

Wei, C-C., et al., "Antioxidative Activities of Both Oleic Acid and Camellia Tenuifolia Seed Oil are Regulated by the Transcription Factor DAF-16/FOXO in Caenorhabditis elegans," 2016, PLoS One, 116:e0157195, 15 pages.

Wu, N., et al., "Constructions and Analysis of GmFAD2-1A and GmFAD2-2A Soybean Fatty Acid Desaturase Mutants Based on CRISPR/Cas9 Technology," 2020, Int J Mol Sci, 21/1104, 11 pages.

Zhang, J., et al., "*Arabidopsis* Fatty Acid Desaturase FAD2 is Required for Salt Tolerance during Seed Germination and Early Seedling Growth," 2012, PLoS One, 7/1:e30355, 12 pages.

Zhou, Z., et al., "Assessment of Phenotypic Variations and Correlation Among Seed Composition Traits in Mutagenized Soybean Populations," 2019, Genes, 10/975, 14 pages.

\* cited by examiner

FIG. 1

| Scaffold | Start | Stop | Glyma | #probes | bp covered | bp in region | % coverage | expected coverage with Flanking data |
|---|---|---|---|---|---|---|---|---|
| Chr10 | 50013364 | 50013926 | Glyma.10G278000 | 12 | 560 | 562 | 0.996441 | 100 |
| Chr10 | 50014094 | 50015460 | Glyma.10G278000 | 32 | 1360 | 1366 | 0.995608 | 100 |
| Chr20 | 35315510 | 35316655 | Glyma.20G111000 | 26 | 1120 | 1145 | 0.978166 | 100 |
| Chr20 | 35316764 | 35317641 | Glyma.20G111000 | 19 | 840 | 877 | 0.957811 | 100 |
| Chr20 | 35317682 | 35319063 | Glyma.20G111000 | 32 | 1360 | 1381 | 0.984794 | 100 |
| Chr19 | 40814864 | 40815305 | Glyma.19G147300 | 9 | 440 | 441 | 0.997732 | 100 |
| Chr19 | 40815527 | 40815975 | Glyma.19G147300 | 9 | 440 | 448 | 0.982143 | 100 |
| Chr19 | 40819962 | 40820319 | Glyma.19G147400 | 6 | 320 | 357 | 0.896359 | 100 |
| Chr19 | 40821993 | 40822850 | Glyma.19G147400 | 17 | 760 | 857 | 0.886815 | 100 |
| Chr19 | 40823429 | 40824926 | Glyma.19G147400 | 35 | 1480 | 1497 | 0.988644 | 100 |
| Chr03 | 36014506 | 36014942 | Glyma.03G144500 | 7 | 360 | 436 | 0.825688 | 100 |
| Chr03 | 36018896 | 36019188 | Glyma.03G144500 | 5 | 280 | 292 | 0.958904 | 100 |
| Chr03 | 36019431 | 36020913 | Glyma.03G144500 | 35 | 1480 | 1482 | 0.998651 | 100 |
| Chr09 | 22174485 | 22175865 | Glyma.09G111900 | 32 | 1360 | 1380 | 0.985507 | 100 |
| Chr09 | 22178991 | 22179274 | Glyma.09G111900 | 5 | 280 | 283 | 0.989399 | 100 |
| Chr15 | 22308021 | 22308902 | Glyma.15G195200 | 20 | 880 | 881 | 0.998865 | 100 |

FIG. 2

| Gene | Gene model | Primers | Primer Sequences | SEQ ID NO | Products (bps) |
|---|---|---|---|---|---|
| GmFAD2-1A | Glyma.10G278000 | FAD2-1A-Fw | CACATTCAGCAAACAACTGA | 1 | 1272 |
| | | FAD2-1A-Rv | TGTACTAATACATGACAAAAC | 2 | |
| GmFAD2-1B | Glyma.20G111000 | FAD2-1B-Fw | GTATTAGACATTCAGCAACAAC | 3 | 1273 |
| | | FAD2-1B-Rv | TTAAGTGATAAGTGACAAAAC | 4 | |
| GmFAD2-2A | Glyma.19G147300 | FAD2-2A-Fw | GTTCATGAAAAGTGCATGGT | 5 | 1114 |
| | | FAD2-2A-Rv | ATTCATCCTAACCGTCACA | 6 | |
| GmFAD2-2B | Glyma.19G147400 | FAD2-2B-Fw | TCGCTTTGATGAGAAACATT | 7 | 1355 |
| | | FAD2-2B-Rv | ACAAAGGAAAGTTCAAACCA | 8 | |
| GmFAD2-2C | Glyma.03G144500 | FAD2-2C-Fw | GTTCATTCTGATTCGGTGAG | 9 | 1350 |
| | | FAD2-2C-Rv | CCCAATAAGCAACCATGATA | 10 | |
| GmFAD2-2D | Glyma.09G111900 | FAD2-2D-Fw | TTGATGAGTTAGTTTTGCAATTA | 11 | 1350 |
| | | FAD2-2D-Rv | TTTATAAGACCATAAGGAACA | 12 | |
| GmFAD2-2E | Glyma.15G195200 | FAD2-2E-Fw | TCACCATAGCCTTCTACCTC | 13 | 1035 |
| | | FAD2-2E-Rv | AGCAACCATGCTACTAAACAG | 14 | |

FIG. 7

| Gene ID | Amplicon size (bp) | Base changes | Type of base changes | | | InDel | Mutation density (Kb) | AA substitutions | Missense mutations | Nonsense mutations | Silent mutations |
|---|---|---|---|---|---|---|---|---|---|---|---|
| | | | G>A | C>T | Others | | | | | | |
| Glyma.10G278000 | 1928 | 50 | 13 | 29 | 8 | 0 | 1/155 | 28 | 17 | 0 | 11 |
| Glyma.20G111000 | 3403 | 89 | 22 | 29 | 38 | 3 | 1/154 | 25 | 11 | 1 | 13 |
| Glyma.19G147300 | 889 | 28 | 13 | 12 | 3 | 1 | 1/128 | 13 | 9 | 1 | 3 |
| Glyma.19G147400 | 2711 | 79 | 26 | 39 | 14 | 5 | 1/138 | 39 | 28 | 2 | 9 |
| Glyma.03G144500 | 2210 | 87 | 29 | 35 | 23 | 3 | 1/102 | 28 | 15 | 1 | 12 |
| Glyma.09G111900 | 1663 | 55 | 18 | 23 | 14 | 2 | 1/121 | 33 | 25 | 2 | 6 |
| Glyma.15G195200 | 881 | 53 | 16 | 24 | 13 | 2 | 1/67 | 30 | 25 | 0 | 5 |
| Total | | 441 | 137 | 191 | 113 | 16 | | 196 | 130 | 7 | 59 |

FIG. 8

| Gene ID | Plant ID | Nucleotide change | Amino acid substitution | C16:0 | C18:0 | C18:1 | C18:2 | C18:3 |
|---|---|---|---|---|---|---|---|---|
| GmFAD2-2A Glyma.19g147300 | F390 | G410T | R137L | 10.4 | 3.5 | 29.6 | 50.1 | 6.4 |
| | F601 | G283A | A95T | 9.6 | 4.8 | 24.8 | 54.3 | 6.4 |
| | F300 | C134T | T45I | 10.7 | 4.1 | 25.1 | 54.0 | 6.1 |
| | F1410 | C38A | P13H | 10.6 | 5.1 | 27.8 | 50.9 | 5.6 |
| | F960 | C91T | R31C | 10.2 | 3.6 | 24.2 | 54.3 | 7.6 |
| | F935 | C103T | R35C | 10.3 | 3.7 | 25.1 | 53.4 | 7.5 |
| | F239 | C211T | P71S | 11.1 | 4.2 | 26.8 | 53.3 | 4.6 |
| | F1044 | C345T | A82V | 10.0 | 5.2 | 26.1 | 54.1 | 4.6 |
| | F1202 | C331T | H111Y | 9.4 | 4.1 | 31.0 | 49.0 | 5.5 |
| | F141 | G346A | V116I | 10.8 | 5.1 | 27.9 | 50.3 | 5.8 |
| | F1581 | C376T | R126C | 10.5 | 4.5 | 28.6 | 51.2 | 5.2 |
| | F1493 | C379T | R127C | 9.7 | 3.4 | 25.8 | 54.5 | 6.6 |
| GmFAD2-2B Glyma.19g147400 | F211 | G994A | A332T | 10.7 | 3.9 | 25.1 | 52.0 | 8.4 |
| | F185 | C277T | Q93* | 9.6 | 3.5 | 25.6 | 50.6 | 10.7 |
| | F45 | G1118A | S373N | 10.8 | 3.7 | 26.3 | 52.1 | 7.1 |
| | F1103 | G284A | C95Y | 10.3 | 3.5 | 28.1 | 51.3 | 6.9 |
| | F1496 | G460A | D154N | 9.7 | 4.8 | 27.8 | 51.3 | 6.4 |
| | F1562 | G466A | V156I | 9.9 | 4.2 | 27.3 | 52.2 | 6.4 |
| | F253 | A672T | Q224H | 10.1 | 4.3 | 27.4 | 52.7 | 5.6 |
| | F921 | C1049T | P350L | 10.2 | 3.7 | 24.1 | 53.5 | 8.5 |
| GmFAD2-2C Glyma.03G144500 | 496-1 | C625T | H209Y | 9.9 | 3.1 | 28.3 | 50.5 | 8.3 |
| | 1106 | G1114A | E372K | 10.2 | 4.2 | 29.6 | 50.8 | 5.3 |
| | 468 | C88T | P30S | 9.9 | 5.6 | 28.2 | 50.0 | 6.2 |
| | 595 | G781A | V261M | 10.4 | 5.1 | 25.7 | 53.5 | 5.3 |
| | 268 | C88T | P30S | 10.2 | 5.9 | 21.7 | 55.0 | 7.1 |
| | F408 | G49A | E17K | 10.3 | 4.3 | 28.9 | 51.3 | 5.2 |
| | F1222 | G175A | D59N | 10.4 | 4.0 | 25.2 | 52.7 | 7.7 |
| | F1748 | C259T | P87S | 10.3 | 4.7 | 26.1 | 51.0 | 7.9 |
| | F1111 | C313A | H105N | 10.5 | 5.3 | 25.5 | 52.7 | 6.0 |
| | F58 | A672T | Q224H | 10.2 | 4.9 | 24.4 | 53.7 | 6.9 |
| | F1165 | G799A | V267M | 9.3 | 3.2 | 27.9 | 50.2 | 9.4 |
| GmFAD2-2D Glyma.09G111900 | 313 | C643T | P215S | 11.0 | 4.9 | 26.9 | 48.8 | 8.4 |
| | 81 | A622T | R208* | 10.3 | 5.2 | 32.7 | 46.5 | 5.2 |
| | 369 | C751T | L251F | 10.7 | 5.0 | 25.3 | 53.1 | 5.9 |
| | 1436 | G1094T | C365F | 10.4 | 5.2 | 27.7 | 50.0 | 6.7 |
| | F1381 | A1020T | K340N | 10.1 | 4.1 | 28.9 | 50.2 | 6.7 |
| | F275 | G905A | R302K | 10.5 | 6.4 | 29.2 | 47.7 | 6.2 |
| | F1117 | G579A | W193* | 10.6 | 4.4 | 27.7 | 50.6 | 6.7 |
| | F470 | G510A | W170* | 9.7 | 4.7 | 30.5 | 48.1 | 6.9 |
| | F1268 | C439T | H147Y | 9.8 | 4.0 | 26.0 | 52.5 | 7.6 |
| GmFAD2-2E Glyma.15g195200 | F1087 | G329A | G110E | 10.3 | 3.8 | 21.3 | 55.7 | 8.9 |
| | F380 | C502T | P168S | 9.9 | 4.2 | 24.6 | 53.5 | 7.7 |
| | F9 | C829T | P277S | 10.9 | 4.3 | 24.0 | 53.6 | 7.3 |
| | F1215 | A803T | E268V | 10.6 | 4.9 | 29.9 | 48.4 | 6.2 |
| | F602 | G754A | E252K | 10.4 | 4.2 | 25.2 | 54.0 | 6.2 |
| | F1328 | G751A | G251R | 10.2 | 4.7 | 27.2 | 52.4 | 5.5 |
| | F1285 | G721A | E241K | 10.4 | 3.9 | 24.4 | 52.5 | 8.8 |
| | F1065 | C706T | H236Y | 11.3 | 4.8 | 29.8 | 47.6 | 6.5 |
| | F226 | G628A | D210N | 11.3 | 5.0 | 33.7 | 44.9 | 5.1 |
| | F69 | G626A | R209K | 10.5 | 4.5 | 25.9 | 52.1 | 7.0 |
| | F1803 | G605A | G202E | 12.3 | 5.0 | 32.0 | 45.5 | 5.2 |
| | F480 | T595A | W199R | 10.9 | 4.5 | 26.4 | 51.6 | 6.6 |
| | F372 | C397T | L133F | 10.5 | 3.6 | 25.7 | 53.9 | 6.3 |
| | F1180 | C350T | A117V | 10.5 | 4.2 | 24.0 | 54.5 | 6.9 |
| | F123 | C334T | P112S | 10.4 | 5.3 | 28.6 | 50.4 | 5.3 |
| | F238 | G328A | G110R | 10.2 | 6.3 | 27.2 | 50.5 | 5.8 |
| | F1480 | C167T | S56F | 9.8 | 4.2 | 25.7 | 53.0 | 7.3 |
| | F1711 | T166A | S56T | 9.4 | 5.1 | 35.2 | 43.5 | 6.3 |
| | F1462 | G61A | A21T | 9.7 | 3.8 | 33.3 | 47.8 | 5.4 |
| | FWT | | | 11.6 | 3.32 | 18 | 54.52 | 6.19 |

FIG. 11

COMPOSITIONS AND METHODS TO INCREASE OLEIC ACID CONTENT IN SOYBEANS

CROSS REFERENCE TO RELATED APPLICATIONS

This application claims the benefit of U.S. Provisional Patent Application No. 63/188,993, filed May 14, 2021, the entire contents of which are incorporate by reference herein.

INCORPORATION OF SEQUENCE LISTING

A paper copy of the Sequence Listing and a computer readable form of the Sequence Listing containing the file named "3512490.0042_Sequence_Listing_ST25," which is 55,496 bytes in size (as measured in MICROSOFT WINDOWS® EXPLORER) and was created on May 12, 2022, are provided herein and are herein incorporated by reference. This Sequence Listing consists of SEQ ID NOs: 1-29.

FIELD OF THE INVENTION

The present invention generally relates to compositions and methods to increase oleic acid content in soybeans.

BACKGROUND OF THE INVENTION

Soybean oil is one of the most consumed vegetable oils worldwide. Soybean oil's utilization is determined by its fatty acid composition. Usually, the content of oleic acid (18:1, ω-9) in soybean oil is about 18-20%. Consumption of oil with high oleic acid content is desirable because this monounsaturated fatty acid improves shelf life and reduces the need for hydrogenation. Additionally, oil high in oleic acid and low in saturated fatty acids are desired by the biodiesel industry, in order to improve the oxidative stability while increasing cold flow.

In plants, mutations can be artificially induced by mutagenic agents and their utilization for production of new superior varieties of species from the traditional variety. Genetic modification of the fatty acid composition of soybean oil is an important goal to improving soybean breeding for better oil traits. While traditional breeding may take several years to achieve traits of interest, mutation breeding is the most useful and vital technology for soybean production. Selection of effective and efficient mutagens is very essential for recovering a high frequency of desirable mutants.

Mutations within the GmFAD2-1A and GmFAD2-1B genes encoding fatty acid desaturases (omega-6 FAD; EC 1.3.1.35) in soybeans were used to produce high oleic acid soybean germplasm. However, it has been reported that high seed oleic acid derived from GmFAD2-1 may have a possible reduction in seed germination when planted in cold soil. The soybean community and industry are making tremendous efforts to determine the optimum allele combinations to produce environmentally stable high oleic/low linolenic acid soybean varieties for US soybean production environments (USB# 1720-162-0109). Therefore, looking for new alternatives to increase soybean seed oleic acid content while maintaining good yield is considered as high priority for the soybean industry. The fatty acid desaturase-2 enzyme (FAD2) is responsible for the conversion of oleic acid to linoleic acid in the developing soybean seeds by introducing a double bond at the Δ12 position of oleic acid. This mono-unsaturated fatty acid contains only one double bond in its carbon chain. The high polyunsaturated fatty acid content in soybean oil exhibits low oxidative stability and must be hydrogenated for many applications, but such process introduces trans fats that cause a number of health problems in humans. Elevated oleic acid content in soybean oil improves oxidative stability and shelf life to avoid hydrogenation and is considered healthier for human consumption. Edible oils containing high level of oleic acid and low level of linoleic acid are considered with higher oxidative stability and can be used as a natural antioxidant in food stability. The traditional GmFAD2-1A and GmFAD2-B genes were well characterized for their role in unsaturated fatty acid biosynthesis. However, members of the GmFAD2-2 subfamily have not yet been characterized. Initially, the expression of the two microsomal GmFAD2-1 desaturases has been mainly detected in developing soybean seeds, therefore, GmFAD2-1A and GmFAD2-1B were regarded as the best candidate genes to develop soybean lines with elevated oleic acid content. However, members of the other GmFAD2-2 gene subfamily were poorly characterized for their role in the fatty acid pathway. The GmFAD2-2 gene family in soybean is composed of five members including GmFAD2-2A (Glyma.19G147300), GmFAD2-2B (Glyma.19G147400), and GmFAD2-2C (Glyma.03G144500), GmFAD2-2D (Glyma.09G111900) and GmFAD2-2E (Glyma.15G195200). Using CRISPR/Cas9, it has been shown recently that GmFAD2-1A and GmFAD2-2A mutants accumulate high levels of soybean seed oleic acid.

Conventional breeding and genetic engineering have been widely applied to produce soybeans with oleic acid content >80% of the total oil. Although downregulation of GmFAD2-1 genes can achieve the elevated levels of oleate through ribozyme-terminated antisense, restrictive regulations from foreign destinations hindered the potentials in exportation of these transgenic soybean. Identification of mutations in GmFAD2-1 genes via reverse genetic approaches appears to be a sustainable strategy to develop non-transgenic soybean with high oleic acid content. Several soybean lines with more than 80% seed oleic acid content have been produced through combining GmFAD2-1A and GmFAD2-1B alleles (soybean diversity). Additionally, using targeted mutagenesis with transcription activator-like effector nucleases (TALENs) in GmFAD2-1 genes, non-transgenic high oleic acid content (80%) can be obtained.

The use of silencing and/or CRISPR techniques is another strategy that could be used to produce high oleic acid soybean lines. However, although it has been accepted in the U.S. as non-transgenic approach, there is still a worldwide debate about the technology and concerns of the vectors used and transgenesis approach to produce and study the desired traits. Therefore, the characterization and availability of TILLING mutants within the GmFAD2-2 gene family members will not only elucidate and attribute a new function of these genes, but will definitely speed up the use of these genes in breeding process.

Using ethyl-methanesulfonate (EMS) mutagenesis effects on DNA, significant changes to the genes and gene network underlying the oil profile in soybean can be achieved. These changes are difficult to achieve using standard breeding techniques. In one embodiment, the present invention is directed to a population of soybean EMS mutagenized lines and TILLING by sequencing+, to functionally characterize the five members of the GmFAD2-2 subfamily in soybean.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a table showing the designed GmFAD2-1A, GmFAD2-1B, GmFAD2-2A, GmFAD2-2B, GmFAD2-2C, GmFAD2-2D, and GmFAD2-2E probes used for TILLING by Target Capture Sequencing.

FIG. 2 is a table showing the primers (SEQ ID NOs: 1-14) used for target Sanger sequencing.

FIG. 3A Six chromosomes carry the GmFAD2 gene family. Glyma.10G278000 (Chr10: 50,013,484-50,015,460); Glyma.20G111000 (Chr20: 35,315,629-35,319,062); Glyma.19G147300 (Chr19: 40,814,864-40,815,855); Glyma.19G147400 (Chr19: 40,819,961-40,824,925); Glyma.03G144500 (Chr03: 36,014,623-36,020,910), Glyma.09G111900 (Chr09: 22,174,486-22,179,275), Glyma.15G195200 (Chr15: 22,308,021-22,308,902). FIG. 3B illustrates gene structures of soybean fatty acid desaturases from three gene families. The structures of 19 soybean fatty acid desaturases genes were plotted with yellow boxes representing exons (coding DNA sequence, CDS), black lines illustrating introns, and blue boxes indicating 5'-UTR and 3'-UTR regions. The size of gene structures could be measured by the scale in the unit of base pair (bp) at the bottom. The gene structure was drawn using the Gene Structure Display Server.

FIG. 5A illustrates an expression of the seven GmFAD2 members in Williams 82 that were retrieved from publicly available RNA-seq data fron the SoyBase (http://www.soybase.org/soyseq). FIG. 5B illustrates the RNAseq data of Forrest cultivar.

FIG. 7 is a table showing the SNP mutations, InDels, and mutation density for the GmFAD2-1A, GmFAD2-1B, GmFAD2-2A, GmFAD2-2B, GmFAD2-2C, GmFAD2-2D, and GmFAD2-2E genes.

FIG. 8 is a table showing all fifty-nine isolated EMS Gmfad2-2 TILLING mutants showing increase in the seed oleic acid content.

(FIG. 10A) All identified cis-elements at the GmFAD2-1 and GmFAD2-2 promoter region (−2 Kb upstream). FIG. 10B Shows the conserved Arabidopsis homeobox protein domain (P$AHBP) that was shared between all GmFAD2-1 and GmFAD2-2 subfamily members with a total match that was significantly higher (459) when compared to the other cis-elements shown in FIG. 10A.

DETAILED DESCRIPTION OF THE INVENTION

Transgenic Soybean Plants

Figure 3A:
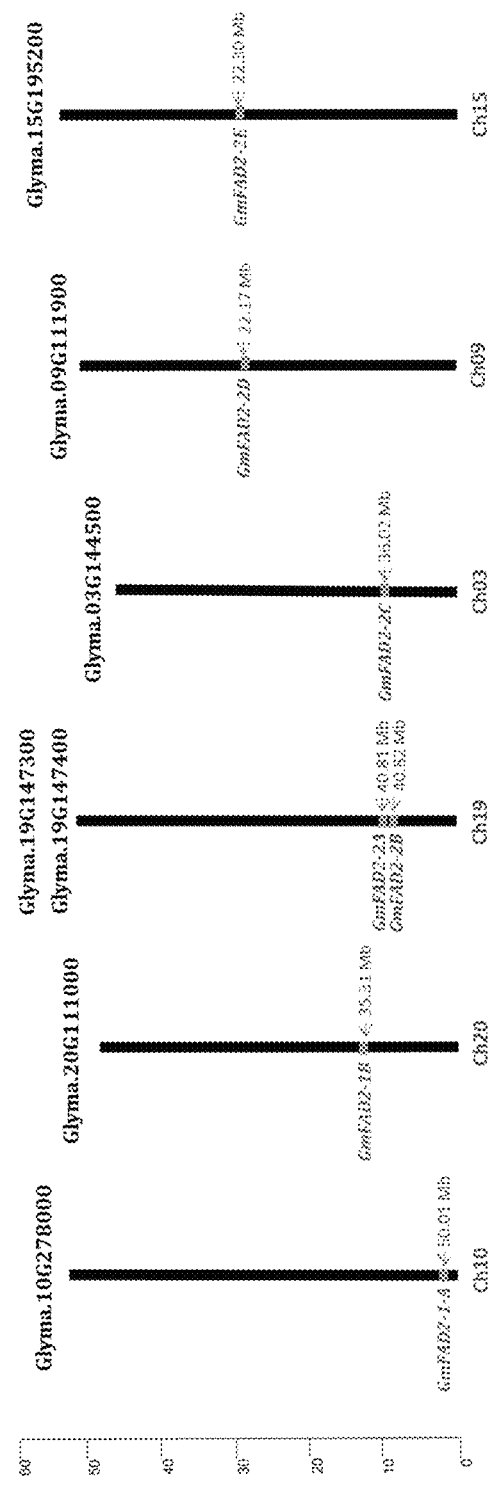
FIGS. 3A and 3B are a series of bar graphs showing the physical positions and gene structures corresponding to the seven GmFAD2s are shown.

One embodiment of the present invention is a transgenic soybean plant with increased oleic acid content comprising a polynucleotide encoding a fatty acid desaturase (FAD) related promoter that functions in the soybean plant operably linked to a polynucleotide encoding a polypeptide having FAD activity.

In one embodiment, the polynucleotide encoding a FAD related promoter may comprise any wild type FAD promoter sequence, or a sequence at least 95% identical thereto, or a full length complement thereof, or a functional fragment thereof. In certain embodiments, the wild type FAD promoter sequence can be selected from the group consisting of a promoter sequence of FAD2-2A, FAD2-2B, FAD2-2C, FAD2-2D, and FAD2-2E.

In some embodiments, the polynucleotide encoding a polypeptide having FAD activity may comprise any wild type FAD genomic or coding sequence, or a sequence at least 95% identical thereto, or a full length complement thereof, or a functional fragment thereof. In one embodiment, the wild type FAD genomic or coding sequence can be selected from the group consisting of a genomic or coding sequence of FAD2-2A, FAD2-2B, FAD2-2C, FAD2-2D, and FAD2-2E.

In various embodiments, the polypeptide having FAD activity may comprise any wild type FAD amino acid sequence, or a sequence at least 95% identical thereto, or a full-length complement thereof, or a functional fragment thereof. In one embodiment, the wild type FAD amino acid sequence can be selected from the group consisting of an amino acid sequence of FAD2-2A, FAD2-2B, FAD2-2C, FAD2-2D, and FAD2-2E.

In some embodiments, the polynucleotide encoding a FAD related promoter may comprise any wild type FAD2-2A promoter sequence, or a sequence at least 95% identical thereto, or a full length complement thereof, or a functional fragment thereof. For example, in one embodiment, the wild type FAD2-2A promoter sequence can comprise the wild type "Forrest" FAD2-2A promoter sequence (SEQ ID NO: 15). In another embodiment, the polynucleotide encoding a polypeptide having FAD activity may comprise any wild type FAD2-2A genomic or coding sequence, or a sequence at least 95% identical thereto, or a full length complement thereof, or a functional fragment thereof. In certain embodiments, the wild type FAD2-2A coding sequence may comprise the wild type "Forrest" FAD2-2A coding sequence (SEQ ID NO: 16), or a sequence at least 95% identical thereto, or a full-length complement thereof, or a functional fragment thereof, and may further comprise one or more mutations of the wild type "Forrest" FAD2-2A coding sequence (SEQ ID NO: 16) selected from the group consisting of C38A, C91T, C103T, C134T, C211T, C245T, G283A, C331T, G346A, C376T, C379T, and G410T. In one embodiment, the polypeptide having FAD activity may comprise the wild type "Forrest" FAD2-2A amino acid sequence (SEQ ID NO: 17), or a sequence at least 95% identical thereto, or a full-length complement thereof, or a functional fragment thereof, and may further comprise one or more mutations of the wild type "Forrest" FAD2-2A amino acid sequence (SEQ ID NO: 17) selected from the group consisting of P13H, R31C, R35C, T45I, P71S, A82V, A95T, H111Y, V116I, R126C, R127C, and R137L.

In another embodiment, the polynucleotide encoding a FAD related promoter may comprise any wild type FAD2-2B promoter sequence, or a sequence at least 95% identical thereto, or a full length complement thereof, or a functional fragment thereof. For example, in one embodiment, the wild type FAD2-2B promoter sequence can comprise the wild type "Forrest" FAD2-2B promoter sequence (SEQ ID NO: 18). In certain embodiments, the polynucleotide encoding a polypeptide having FAD activity may comprise any wild type FAD2-2B genomic or coding sequence, or a sequence at least 95% identical thereto, or a full length complement thereof, or a functional fragment thereof. In one embodiment, the wild type FAD2-2B coding sequence may comprise the wild type "Forrest" FAD2-2B coding sequence (SEQ ID NO: 19), or a sequence at least 95% identical thereto, or a full-length complement thereof, or a functional fragment thereof, and may further comprise one or more mutations of the wild type "Forrest" FAD2-2B coding sequence (SEQ ID NO: 19) selected from the group consisting of C277T, G284A, G460A, G466A, A672T, G994A, C1049T, and G1118A. In another embodiment, the polypeptide having FAD activity may comprise the wild type "Forrest" FAD2-2B amino acid sequence (SEQ ID NO: 20), or a sequence at least 95% identical thereto, or a full-length complement thereof, or a functional fragment thereof, and may further comprise one or more mutations of the wild type "Forrest" FAD2-2B amino acid sequence (SEQ ID NO: 20) selected from the group consisting of Q93*, C95Y, D154N, V156I, Q224H, A332T, P350L, and S373N.

In one embodiment, the polynucleotide encoding a FAD related promoter may comprise any wild type FAD2-2C promoter sequence, or a sequence at least 95% identical thereto, or a full length complement thereof, or a functional fragment thereof. For example, in one embodiment, the wild type FAD2-2C promoter sequence can comprise the wild type "Forrest" FAD2-2C promoter sequence (SEQ ID NO: 21). In certain embodiments, the polynucleotide encoding a polypeptide having FAD activity may comprise any wild type FAD2-2C genomic or coding sequence, or a sequence at least 95% identical thereto, or a full length complement thereof, or a functional fragment thereof. In one embodiment, the wild type FAD2-2C coding sequence may comprise the wild type "Forrest" FAD2-2C coding sequence (SEQ ID NO: 22), or a sequence at least 95% identical thereto, or a full-length complement thereof, or a functional fragment thereof, and may further comprise one or more mutations of the wild type "Forrest" FAD2-2C coding sequence (SEQ ID NO: 22) selected from the group consisting of: G49A, C88T, G175A, C259T, C313A, C625T, A672T, G781A, G799A, and G1114A. In another embodiment, the polypeptide having FAD activity may comprise the wild type "Forrest" FAD2-2C amino acid sequence (SEQ ID NO: 23), or a sequence at least 95% identical thereto, or a full-length complement thereof, or a functional fragment thereof, and may further comprise one or more mutations of the wild type "Forrest" FAD2-2C amino acid sequence (SEQ ID NO: 23) selected from the group consisting of: E17K, P30S, D59N, P87S, H105N, H209Y, Q224H, V261M, V267M, and E372K.

In one embodiment, the polynucleotide encoding a FAD related promoter may comprise any wild type FAD2-2D promoter sequence, or a sequence at least 95% identical thereto, or a full length complement thereof, or a functional fragment thereof. For example, in one embodiment, the wild type FAD2-2D promoter sequence can comprise the wild type "Forrest" FAD2-2D promoter sequence (SEQ ID NO: 24). In another embodiment, the polynucleotide encoding a polypeptide having FAD activity may comprise any wild type FAD2-2D genomic or coding sequence, or a sequence at least 95% identical thereto, or a full length complement thereof, or a functional fragment thereof. In still further embodiments, the wild type FAD2-2D coding sequence may comprise the wild type "Forrest" FAD2-2D coding sequence (SEQ ID NO: 25), or a sequence at least 95% identical thereto, or a full-length complement thereof, or a functional fragment thereof, and may further comprise one or more mutations of the wild type "Forrest" FAD2-2D coding sequence (SEQ ID NO: 25) selected from the group consisting of C439T, G510A, G579A, A622T, C643T, C751T, G905A, A1020T, and G1094T. In another embodiment, the polypeptide having FAD activity may comprise the wild type "Forrest" FAD2-2D amino acid sequence (SEQ ID NO: 26), or a sequence at least 95% identical thereto, or a full-length complement thereof, or a functional fragment thereof, and may further comprise one or more mutations of the wild type "Forrest" FAD2-2D amino acid sequence (SEQ ID NO: 26) selected from the group consisting of H147Y, W170*, W193*, R208*, P215S, L251F, R302K, K340N, and C365F.

In one embodiment, the polynucleotide encoding a FAD related promoter may comprise any wild type FAD2-2E promoter sequence, or a sequence at least 95% identical thereto, or a full length complement thereof, or a functional fragment thereof. For example, in one embodiment, the wild type FAD2-2E promoter sequence can comprise the wild type "Forrest" FAD2-2E promoter sequence (SEQ ID NO: 27). In some embodiments, the polynucleotide encoding a polypeptide having FAD activity may comprise any wild type FAD2-2E genomic or coding sequence, or a sequence at least 95% identical thereto, or a full length complement thereof, or a functional fragment thereof. In one embodiment, the wild type FAD2-2E coding sequence may comprise the wild type "Forrest" FAD2-2E coding sequence (SEQ ID NO: 28), or a sequence at least 95% identical thereto, or a full-length complement thereof, or a functional fragment thereof, and may further comprise one or more mutations of the wild type "Forrest" FAD2-2E coding sequence (SEQ ID NO: 28) selected from the group consisting of G61A, T166A, C167T, G328A, G329A, C334T, C350T, C397T, C502T, T595A, G605A, G626A, G628A, C706T, G721A, G751A, G754A, A803T, and C829T. In another embodiment, the polypeptide having FAD activity may comprise the wild type "Forrest" FAD2-2E amino acid sequence (SEQ ID NO: 29), or a sequence at least 95% identical thereto, or a full-length complement thereof, or a functional fragment thereof, and may further comprise one or more mutations of the wild type "Forrest" FAD2-2E amino acid sequence (SEQ ID NO: 29) selected from the group consisting of A21T, S56F, S56T, G110E, G110R, P112S, A117V, L133F, P168S, W199R, G202E, R209K, D210N, H236Y, E241K, G251R, E252K, E268V, and P277S.

In one embodiment, the transgenic soybean plant with increased oleic acid content may comprise two or more polynucleotides, each encoding a FAD related promoter that functions in the soybean plant, provided that each polynucleotide encoding a FAD related promoter that functions in the soybean plant is operably linked to a polynucleotide encoding a polypeptide having FAD activity.

In certain embodiments, the two or more polynucleotides encoding a FAD related promoter may be selected from the group consisting of:

(i) any wild type FAD2-2A promoter sequence, or a sequence at least 95% identical thereto, or a full length complement thereof, or a functional fragment thereof, wherein the polypeptide having FAD activity comprises the wild type "Forrest" FAD2-2A amino acid sequence (SEQ ID NO: 17), or a sequence at least 95% identical thereto, or a full-length complement thereof, or a functional fragment thereof, and further comprises one or more mutations of the wild type "Forrest" FAD2-2A amino acid sequence (SEQ ID NO: 17) selected from the group consisting of: P13H, R31C, R35C, T45I, P71S, A82V, A95T, H111Y, V116I, R126C, R127C, and R137L. In one embodiment, the wild type FAD2-2A promoter sequence may be the wild type "Forrest" FAD2-2A promoter sequence (SEQ ID NO: 15), wherein the polynucleotide encoding a polypeptide having FAD activity comprises the wild type "Forrest" FAD2-2A coding sequence (SEQ ID NO: 16), or a sequence at least 95% identical thereto, or a full-length complement thereof, or a functional fragment thereof, and further comprises one or more mutations of the wild type "Forrest" FAD2-2A coding sequence (SEQ ID NO: 16) selected from the group consisting of C38A, C91T, C103T, C134T, C211T, C245T, G283A, C331T, G346A, C376T, C379T, and G410T;

(ii) any wild type FAD2-2B promoter sequence, or a sequence at least 95% identical thereto, or a full length complement thereof, or a functional fragment thereof, wherein the polypeptide having FAD activity comprises the wild type "Forrest" FAD2-2B amino acid sequence (SEQ ID NO: 20), or a sequence at least 95% identical thereto, or a full-length complement thereof, or a functional fragment thereof, and further comprises one or more mutations of the wild type "Forrest" FAD2-2B amino acid sequence (SEQ ID NO: 20) selected from the group consisting of: Q93*, C95Y, D154N, V156I, Q224H, A332T, P350L, and S373N. In one embodiment, the wild type FAD2-2B promoter sequence may be the wild type "Forrest" FAD2-2B promoter sequence (SEQ ID NO: 18), wherein the polynucleotide encoding a polypeptide having FAD activity comprises the wild type "Forrest" FAD2-2B coding sequence (SEQ ID NO: 19), or a sequence at least 95% identical thereto, or a full-length complement thereof, or a functional fragment thereof, and further comprises one or more mutations of the wild type "Forrest" FAD2-2B coding sequence (SEQ ID NO: 19) selected from the group consisting of: C277T, G284A, G460A, G466A, A672T, G994A, C1049T, and G1118A;

(iii) any wild type FAD2-2C promoter sequence, or a sequence at least 95% identical thereto, or a full length complement thereof, or a functional fragment thereof, wherein the polypeptide having FAD activity comprises the wild type "Forrest" FAD2-2C amino acid sequence (SEQ ID NO: 23), or a sequence at least 95% identical thereto, or a full-length complement thereof, or a functional fragment thereof, and further comprises one or more mutations of the wild type "Forrest" FAD2-2C amino acid sequence (SEQ ID NO: 23) selected from the group consisting of: E17K, P30S, D59N, P87S, H105N, H209Y, Q224H, V261M, V267M, and E372K. In one embodiment, the wild type FAD2-2C promoter sequence may be the wild type "Forrest" FAD2-2C promoter sequence (SEQ ID NO: 21), wherein the polynucleotide encoding a polypeptide having FAD activity comprises the wild type "Forrest" FAD2-2C coding sequence (SEQ ID NO: 22), or a sequence at least 95% identical thereto, or a full-length complement thereof, or a functional fragment thereof, and further comprises one or more mutations of the wild type "Forrest" FAD2-2C coding sequence (SEQ ID NO: 22) selected from the group consisting of: G49A, C88T, G175A, C259T, C313A, C625T, A672T, G781A, G799A, and G1114A;

(iv) any wild type FAD2-2D promoter sequence, or a sequence at least 95% identical thereto, or a full length complement thereof, or a functional fragment thereof, wherein the polypeptide having FAD activity comprises the wild type "Forrest" FAD2-2D amino acid sequence (SEQ ID NO: 26), or a sequence at least 95% identical thereto, or a full-length complement thereof, or a functional fragment thereof, and further comprises one or more mutations of the wild type "Forrest" FAD2-2D amino acid sequence (SEQ ID NO: 26) selected from the group consisting of: H147Y, W170*, W193*, R208*, P215S, L251F, R302K, K340N, and C365F. In one embodiment, the wild type FAD2-2D promoter sequence may be the wild type "Forrest" FAD2-2D promoter sequence (SEQ ID NO: 24), wherein the polynucleotide encoding a polypeptide having FAD activity comprises the wild type "Forrest" FAD2-2D coding sequence (SEQ ID NO: 25), or a sequence at least 95% identical thereto, or a full-length complement thereof, or a functional fragment thereof, and further comprises one or more mutations of the wild type "Forrest" FAD2-2D coding sequence (SEQ ID NO: 25) selected from the group consisting of: C439T, G510A, G579A, A622T, C643T, C751T, G905A, A1020T, and G1094T; and (v) any wild type FAD2-2E promoter sequence, or a sequence at least 95% identical thereto, or a full length complement thereof, or a functional fragment thereof, wherein the polypeptide having FAD activity comprises the wild type "Forrest" FAD2-2E amino acid sequence (SEQ ID NO: 29), or a sequence at least 95% identical thereto, or a full-length complement thereof, or a functional fragment thereof, and further comprises one or more mutations of the wild type "Forrest" FAD2-2E amino acid sequence (SEQ ID NO: 29) selected from the group consisting of: A21T, S56F, S56T, G110E, G110R, P112S, A117V, L133F, P168S, W199R, G202E, R209K, D210N, H236Y, E241K, G251R, E252K, E268V, and P277S. In one embodiment, the wild type FAD2-2E promoter sequence may be the wild type "Forrest" FAD2-2E promoter sequence (SEQ ID NO: 27), wherein the polynucleotide encoding a polypeptide having FAD activity comprises the wild type "Forrest" FAD2-2E coding sequence (SEQ ID NO: 28), or a sequence at least 95% identical thereto, or a full-length complement thereof, or a functional fragment thereof, and further comprises one or more mutations of the wild type "Forrest" FAD2-2E coding sequence (SEQ ID NO: 28) selected from the group consisting of: G61A, T166A, C167T, G328A, G329A, C334T, C350T, C397T, C502T, T595A, G605A, G626A, G628A, C706T, G721A, G751A, G754A, A803T, and C829T.

In one embodiment, the transgenic soybean plant may have increased oleic acid content compared to a control soybean plant lacking the polynucleotide encoding a polypeptide having FAD activity as described above. In certain embodiments, the increased oleic acid content may comprise an at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, at least about 60%, at least about 70%, at least about 80%, at least about 90%, or at least about 100% increase in oleic acid content as compared to the control soybean plant lacking the polynucleotide encoding a polypeptide having FAD activity as described above.

An additional embodiment of the present invention is directed to a plant part of any of the transgenic soybean plants described above.

Agronomically Elite Soybean Varieties

Another embodiment of the present invention is directed to a plant of an agronomically elite soybean variety with increased oleic acid content comprising a polynucleotide encoding a fatty acid desaturase (FAD) related promoter that functions in the soybean plant operably linked to a polynucleotide encoding a polypeptide having FAD activity.

The polynucleotide encoding a FAD related promoter may comprise any wild type FAD promoter sequence, or a sequence at least 95% identical thereto, or a full length complement thereof, or a functional fragment thereof. In one embodiment, the wild type FAD promoter sequence can be selected from the group consisting of a promoter sequence of FAD2-2A, FAD2-2B, FAD2-2C, FAD2-2D, and FAD2-2E.

In certain embodiments, the polynucleotide encoding a polypeptide having FAD activity may comprise any wild type FAD genomic or coding sequence, or a sequence at least 95% identical thereto, or a full length complement thereof, or a functional fragment thereof. In one embodiment, the wild type FAD genomic or coding sequence can be selected from the group consisting of a genomic or coding sequence of FAD2-2A, FAD2-2B, FAD2-2C, FAD2-2D, and FAD2-2E.

The polypeptide having FAD activity may comprise any wild type FAD sequence, or a sequence at least 95% identical thereto, or a full-length complement thereof, or a functional fragment thereof. In one embodiment, the wild type FAD amino acid sequence can be selected from the group consisting of an amino acid sequence of FAD2-2A, FAD2-2B, FAD2-2C, FAD2-2D, and FAD2-2E.

In one embodiment, the polynucleotide encoding a FAD related promoter may comprise any wild type FAD2-2A promoter sequence, or a sequence at least 95% identical thereto, or a full length complement thereof, or a functional fragment thereof. For example, the wild type FAD2-2A promoter sequence can comprise the wild type "Forrest" FAD2-2A promoter sequence (SEQ ID NO: 15). In certain embodiment, the polynucleotide encoding a polypeptide having FAD activity may comprise any wild type FAD2-2A genomic or coding sequence, or a sequence at least 95% identical thereto, or a full length complement thereof, or a functional fragment thereof. In some embodiment, the wild type FAD2-2A coding sequence may comprise the wild type "Forrest" FAD2-2A coding sequence (SEQ ID NO: 16), or a sequence at least 95% identical thereto, or a full-length complement thereof, or a functional fragment thereof, and may further comprise one or more mutations of the wild type "Forrest" FAD2-2A coding sequence (SEQ ID NO: 16) selected from the group consisting of: C38A, C91T, C103T, C134T, C211T, C245T, G283A, C331T, G346A, C376T, C379T, and G410T. In one embodiment, the polypeptide having FAD activity may comprise the wild type "Forrest" FAD2-2A amino acid sequence (SEQ ID NO: 17), or a sequence at least 95% identical thereto, or a full-length complement thereof, or a functional fragment thereof, and may further comprise one or more mutations of the wild type "Forrest" FAD2-2A amino acid sequence (SEQ ID NO: 17) selected from the group consisting of: P13H, R31C, R35C, T45I, P71S, A82V, A95T, H111Y, V116I, R126C, R127C, and R137L.

In another embodiment, the polynucleotide encoding a FAD related promoter may comprise any wild type FAD2-2B promoter sequence, or a sequence at least 95% identical thereto, or a full length complement thereof, or a functional fragment thereof. In one embodiment, the wild type FAD2-2B promoter sequence can comprise the wild type "Forrest" FAD2-2B promoter sequence (SEQ ID NO: 18). In certain embodiments, the polynucleotide encoding a polypeptide having FAD activity may comprise any wild type FAD2-2B genomic or coding sequence, or a sequence at least 95% identical thereto, or a full length complement thereof, or a functional fragment thereof. In some embodiments, the wild type FAD2-2B coding sequence may comprise the wild type "Forrest" FAD2-2B coding sequence (SEQ ID NO: 19), or a sequence at least 95% identical thereto, or a full-length complement thereof, or a functional fragment thereof, and may further comprise one or more mutations of the wild type "Forrest" FAD2-2B coding sequence (SEQ ID NO: 19) selected from the group consisting of: C277T, G284A, G460A, G466A, A672T, G994A, C1049T, and G1118A. In one embodiment, the polypeptide having FAD activity may comprise the wild type "Forrest" FAD2-2B amino acid sequence (SEQ ID NO: 20), or a sequence at least 95% identical thereto, or a full-length complement thereof, or a functional fragment thereof, and may further comprise one or more mutations of the wild type "Forrest" FAD2-2B amino acid sequence (SEQ ID NO: 20) selected from the group consisting of: Q93*, C95Y, D154N, V156I, Q224H, A332T, P350L, and S373N.

In one embodiment, the polynucleotide encoding a FAD related promoter may comprise any wild type FAD2-2C promoter sequence, or a sequence at least 95% identical thereto, or a full length complement thereof, or a functional fragment thereof. In another embodiment, the wild type FAD2-2C promoter sequence can comprise the wild type "Forrest" FAD2-2C promoter sequence (SEQ ID NO: 21). In certain embodiments, the polynucleotide encoding a polypeptide having FAD activity may comprise any wild type FAD2-2C genomic or coding sequence, or a sequence at least 95% identical thereto, or a full length complement thereof, or a functional fragment thereof. In a specific embodiment, the wild type FAD2-2C coding sequence may comprise the wild type "Forrest" FAD2-2C coding sequence (SEQ ID NO: 22), or a sequence at least 95% identical thereto, or a full-length complement thereof, or a functional fragment thereof, and may further comprise one or more mutations of the wild type "Forrest" FAD2-2C coding sequence (SEQ ID NO: 22) selected from the group consisting of: G49A, C88T, G175A, C259T, C313A, C625T, A672T, G781A, G799A, and G1114A. In further embodiments, the polypeptide having FAD activity may comprise the wild type "Forrest" FAD2-2C amino acid sequence (SEQ ID NO: 23), or a sequence at least 95% identical thereto, or a full-length complement thereof, or a functional fragment thereof, and may further comprise one or more mutations of the wild type "Forrest" FAD2-2C amino acid sequence (SEQ ID NO: 23) selected from the group consisting of: E17K, P30S, D59N, P87S, H105N, H209Y, Q224H, V261M, V267M, and E372K.

In one embodiment, the polynucleotide encoding a FAD related promoter may comprise any wild type FAD2-2D promoter sequence, or a sequence at least 95% identical thereto, or a full length complement thereof, or a functional fragment thereof. For example, in one embodiment, the wild type FAD2-2D promoter sequence can comprise the wild type "Forrest" FAD2-2D promoter sequence (SEQ ID NO: 24). In another embodiment, the polynucleotide encoding a polypeptide having FAD activity may comprise any wild type FAD2-2D genomic or coding sequence, or a sequence at least 95% identical thereto, or a full length complement thereof, or a functional fragment thereof. In a further embodiment, the wild type FAD2-2D coding sequence may comprise the wild type "Forrest" FAD2-2D coding sequence (SEQ ID NO: 25), or a sequence at least 95% identical thereto, or a full-length complement thereof, or a functional fragment thereof, and may further comprise one or more mutations of the wild type "Forrest" FAD2-2D coding sequence (SEQ ID NO: 25) selected from the group consisting of: C439T, G510A, G579A, A622T, C643T, C751T, G905A, A1020T, and G1094T. In a still further embodiment, the polypeptide having FAD activity may comprise the wild type "Forrest" FAD2-2D amino acid sequence (SEQ ID NO: 26), or a sequence at least 95% identical thereto, or a full-length complement thereof, or a functional fragment thereof, and may further comprise one or more mutations of the wild type "Forrest" FAD2-2D amino acid sequence (SEQ ID NO: 26) selected from the group consisting of: H147Y, W170*, W193*, R208*, P215S, L251F, R302K, K340N, and C365F.

In one embodiment, the polynucleotide encoding a FAD related promoter may comprise any wild type FAD2-2E promoter sequence, or a sequence at least 95% identical thereto, or a full length complement thereof, or a functional fragment thereof. For example, in one embodiment, the wild type FAD2-2E promoter sequence can comprise the wild type "Forrest" FAD2-2E promoter sequence (SEQ ID NO: 27). In certain embodiments, the polynucleotide encoding a polypeptide having FAD activity may comprise any wild type FAD2-2E genomic or coding sequence, or a sequence at least 95% identical thereto, or a full length complement thereof, or a functional fragment thereof. In some embodiments, the wild type FAD2-2E coding sequence may comprise the wild type "Forrest" FAD2-2E coding sequence (SEQ ID NO: 28), or a sequence at least 95% identical thereto, or a full-length complement thereof, or a functional fragment thereof, and may further comprise one or more mutations of the wild type "Forrest" FAD2-2E coding sequence (SEQ ID NO: 28) selected from the group consisting of: G61A, T166A, C167T, G328A, G329A, C334T, C350T, C397T, C502T, T595A, G605A, G626A, G628A, C706T, G721A, G751A, G754A, A803T, and C829T. In another embodiment, the polypeptide having FAD activity may comprise the wild type "Forrest" FAD2-2E amino acid sequence (SEQ ID NO: 29), or a sequence at least 95% identical thereto, or a full-length complement thereof, or a functional fragment thereof, and may further comprise one or more mutations of the wild type "Forrest" FAD2-2E amino acid sequence (SEQ ID NO: 29) selected from the group consisting of: A21T, S56F, S56T, G110E, G110R, P112S, A117V, L133F, P168S, W199R, G202E, R209K, D210N, H236Y, E241K, G251R, E252K, E268V, and P277S.

In one embodiment, the plant with increased oleic acid content may comprise two or more polynucleotides encoding a FAD related promoter that functions in the soybean plant, provided that each polynucleotide encoding a FAD related promoter that functions in the soybean plant is operably linked to a polynucleotide encoding a polypeptide having FAD activity.

In one embodiment, the more than one polynucleotide encoding a FAD related promoter may be selected from the group consisting of:
(i) any wild type FAD2-2A promoter sequence, or a sequence at least 95% identical thereto, or a full length complement thereof, or a functional fragment thereof, wherein the wild type FAD2-2A promoter sequence may be the wild type "Forrest" FAD2-2A promoter sequence (SEQ ID NO: 15), wherein the polynucleotide encoding a polypeptide having FAD activity comprises the wild type "Forrest" FAD2-2A coding sequence (SEQ ID NO: 16), or a sequence at least 95% identical thereto, or a full-length complement thereof, or a functional fragment thereof, and further comprises one or more mutations of the wild type "Forrest" FAD2-2A coding sequence (SEQ ID NO: 16) selected from the group consisting of: C38A, C91T, C103T, C134T, C211T, C245T, G283A, C331T, G346A, C376T, C379T, and G410T, wherein the polypeptide having FAD activity comprises the wild type "Forrest" FAD2-2A amino acid sequence (SEQ ID NO: 17), or a sequence at least 95% identical thereto, or a full-length complement thereof, or a functional fragment thereof, and further comprises one or more mutations of the wild type "Forrest" FAD2-2A amino acid sequence (SEQ ID NO: 17) selected from the group consisting of: P13H, R31C, R35C, T45I, P71S, A82V, A95T, H111Y, V116I, R126C, R127C, and R137L;

(ii) any wild type FAD2-2B promoter sequence, or a sequence at least 95% identical thereto, or a full length complement thereof, or a functional fragment thereof, wherein the wild type FAD2-2B promoter sequence may be the wild type "Forrest" FAD2-2B promoter sequence (SEQ ID NO: 18), wherein the polynucleotide encoding a polypeptide having FAD activity comprises the wild type "Forrest" FAD2-2B coding sequence (SEQ ID NO: 19), or a sequence at least 95% identical thereto, or a full-length complement thereof, or a functional fragment thereof, and further comprises one or more mutations of the wild type "Forrest" FAD2-2B coding sequence (SEQ ID NO: 19) selected from the group consisting of: C277T, G284A, G460A, G466A, A672T, G994A, C1049T, and G1118A, wherein the polypeptide having FAD activity comprises the wild type "Forrest" FAD2-2B amino acid sequence (SEQ ID NO: 20), or a sequence at least 95% identical thereto, or a full-length complement thereof, or a functional fragment thereof, and further comprises one or more mutations of the wild type "Forrest" FAD2-2B amino acid sequence (SEQ ID NO: 20) selected from the group consisting of: Q93*, C95Y, D154N, V156I, Q224H, A332T, P350L, and S373N;

(iii) any wild type FAD2-2C promoter sequence, or a sequence at least 95% identical thereto, or a full length complement thereof, or a functional fragment thereof, wherein the wild type FAD2-2C promoter sequence may be the wild type "Forrest" FAD2-2C promoter sequence (SEQ ID NO: 21), wherein the polynucleotide encoding a polypeptide having FAD activity comprises the wild type "Forrest" FAD2-2C coding sequence (SEQ ID NO: 22), or a sequence at least 95% identical thereto, or a full-length complement thereof, or a functional fragment thereof, and further comprises one or more mutations of the wild type "Forrest" FAD2-2C coding sequence (SEQ ID NO: 22) selected from the group consisting of: G49A, C88T, G175A, C259T, C313A, C625T, A672T, G781A, G799A, and G1114A, wherein the polypeptide having FAD activity comprises the wild type "Forrest" FAD2-2C amino acid sequence (SEQ ID NO: 23), or a sequence at least 95% identical thereto, or a full-length complement thereof, or a functional fragment thereof, and further comprises one or more mutations of the wild type "Forrest" FAD2-2C amino acid sequence (SEQ ID NO: 23) selected from the group consisting of: E17K, P30S, D59N, P87S, H105N, H209Y, Q224H, V261M, V267M, and E372K;

(iv) any wild type FAD2-2D promoter sequence, or a sequence at least 95% identical thereto, or a full length complement thereof, or a functional fragment thereof, wherein the wild type FAD2-2D promoter sequence may be the wild type "Forrest" FAD2-2D promoter sequence (SEQ ID NO: 24), wherein the polynucleotide encoding a polypeptide having FAD activity comprises the wild type "Forrest" FAD2-2D coding sequence (SEQ ID NO: 25), or a sequence at least 95% identical thereto, or a full-length complement thereof, or a functional fragment thereof, and further comprises one or more mutations of the wild type "Forrest" FAD2-2D coding sequence (SEQ ID NO: 25) selected from the group consisting of: C439T, G510A, G579A, A622T, C643T, C751T, G905A, A1020T, and G1094T, wherein the polypeptide having FAD activity comprises the wild type "Forrest" FAD2-2D amino acid sequence (SEQ ID NO: 26), or a sequence at least 95% identical thereto, or a full-length complement thereof, or a functional fragment thereof, and further comprises one or more mutations of the wild type "Forrest" FAD2-2D amino acid sequence (SEQ ID NO: 26) selected from the group consisting of: H147Y, W170*, W193*, R208*, P215S, L251F, R302K, K340N, and C365F; and (v) any wild type FAD2-2E promoter sequence, or a sequence at least 95% identical thereto, or a full length complement thereof, or a functional fragment thereof, wherein the wild type FAD2-2E promoter sequence may be the wild type "Forrest" FAD2-2E promoter sequence (SEQ ID NO: 27), wherein the polynucleotide encoding a polypeptide having FAD activity comprises the wild type "Forrest" FAD2-2E coding sequence (SEQ ID NO: 28), or a sequence at least 95% identical thereto, or a full-length complement thereof, or a functional fragment thereof, and further comprises one or more mutations of the wild type "Forrest" FAD2-2E coding sequence (SEQ ID NO: 28) selected from the group consisting of: G61A, T166A, C167T, G328A, G329A, C334T, C350T, C397T, C502T, T595A, G605A, G626A, G628A, C706T, G721A, G751A, G754A, A803T, and C829T, wherein the polypeptide having FAD activity comprises the wild type "Forrest" FAD2-2E amino acid sequence (SEQ ID NO: 29), or a sequence at least 95% identical thereto, or a full-length complement thereof, or a functional fragment thereof, and further comprises one or more mutations of the wild type "Forrest" FAD2-2E amino acid sequence (SEQ ID NO: 29) selected from the group consisting of: A21T, S56F, S56T, G110E, G110R, P112S, A117V, L133F, P168S, W199R, G202E, R209K, D210N, H236Y, E241K, G251R, E252K, E268V, and P277S.

In one embodiment, the plant may have increased oleic acid content compared to a control soybean plant lacking the polynucleotide encoding a polypeptide having FAD activity as described above. For example, in one embodiment, the increased oleic acid content may comprise an at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, at least about 60%, at least about 70%, at least about 80%, at least about 90%, or at least about 100% increase in oleic acid content as compared to the control soybean plant lacking the polynucleotide encoding a polypeptide having FAD activity as described above.

An additional embodiment of the invention is directed to a plant part of any of the plants described above.

Methods of Increasing Seed Oleic Acid Content

Another embodiment of the present invention is directed to a method of increasing oleic acid content of a soybean plant. The method comprises transforming the soybean plant with a polynucleotide encoding a fatty acid desaturase (FAD) related promoter that functions in the soybean plant operably linked to a polynucleotide encoding a polypeptide having FAD activity.

In one embodiment, the polynucleotide encoding a FAD related promoter may comprise any wild type FAD promoter sequence, or a sequence at least 95% identical thereto, or a full length complement thereof, or a functional fragment thereof. For example, in one embodiment, the wild type FAD promoter sequence can be selected from the group consisting of a promoter sequence of FAD2-2A, FAD2-2B, FAD2-2C, FAD2-2D, and FAD2-2E.

In certain embodiments, the polynucleotide encoding a polypeptide having FAD activity may comprise any wild type FAD genomic or coding sequence, or a sequence at least 95% identical thereto, or a full length complement thereof, or a functional fragment thereof. In other embodiments, the wild type FAD genomic or coding sequence can be selected from the group consisting of a genomic or coding sequence of FAD2-2A, FAD2-2B, FAD2-2C, FAD2-2D, and FAD2-2E.

In one embodiment, the polypeptide having FAD activity may comprise any wild type FAD sequence, or a sequence at least 95% identical thereto, or a full-length complement thereof, or a functional fragment thereof. For example, in one embodiment, the wild type FAD amino acid sequence can be selected from the group consisting of an amino acid sequence of FAD2-2A, FAD2-2B, FAD2-2C, FAD2-2D, and FAD2-2E.

In one embodiment, the polynucleotide encoding a FAD related promoter may comprise any wild type FAD2-2A promoter sequence, or a sequence at least 95% identical thereto, or a full length complement thereof, or a functional fragment thereof. For example, in one embodiment, the wild type FAD2-2A promoter sequence can comprise the wild type "Forrest" FAD2-2A promoter sequence (SEQ ID NO: 15). In certain embodiments, the polynucleotide encoding a polypeptide having FAD activity may comprise any wild type FAD2-2A genomic or coding sequence, or a sequence at least 95% identical thereto, or a full length complement thereof, or a functional fragment thereof. In other embodiments, the wild type FAD2-2A coding sequence may comprise the wild type "Forrest" FAD2-2A coding sequence (SEQ ID NO: 16), or a sequence at least 95% identical thereto, or a full-length complement thereof, or a functional fragment thereof, and may further comprise one or more mutations of the wild type "Forrest" FAD2-2A coding sequence (SEQ ID NO: 16) selected from the group consisting of: C38A, C91T, C103T, C134T, C211T, C245T, G283A, C331T, G346A, C376T, C379T, and G410T. In still further embodiments, the polypeptide having FAD activity may comprise the wild type "Forrest" FAD2-2A amino acid sequence (SEQ ID NO: 17), or a sequence at least 95% identical thereto, or a full-length complement thereof, or a functional fragment thereof, and may further comprise one or more mutations of the wild type "Forrest" FAD2-2A amino acid sequence (SEQ ID NO: 17) selected from the group consisting of: P13H, R31C, R35C, T45I, P71S, A82V, A95T, H111Y, V116I, R126C, R127C, and R137L.

In one embodiment, the polynucleotide encoding a FAD related promoter may comprise any wild type FAD2-2B promoter sequence, or a sequence at least 95% identical thereto, or a full length complement thereof, or a functional fragment thereof. For example, in one embodiment, the wild type FAD2-2B promoter sequence can comprise the wild type "Forrest" FAD2-2B promoter sequence (SEQ ID NO: 18). In some embodiments, the polynucleotide encoding a polypeptide having FAD activity may comprise any wild type FAD2-2B genomic or coding sequence, or a sequence at least 95% identical thereto, or a full length complement thereof, or a functional fragment thereof. In other embodiments, the wild type FAD2-2B coding sequence may comprise the wild type "Forrest" FAD2-2B coding sequence (SEQ ID NO: 19), or a sequence at least 95% identical thereto, or a full-length complement thereof, or a functional fragment thereof, and may further comprise one or more mutations of the wild type "Forrest" FAD2-2B coding sequence (SEQ ID NO: 19) selected from the group consisting of: C277T, G284A, G460A, G466A, A672T, G994A, C1049T, and G1118A. In still further embodiments, the polypeptide having FAD activity may comprise the wild type "Forrest" FAD2-2B amino acid sequence (SEQ ID NO: 20), or a sequence at least 95% identical thereto, or a full-length complement thereof, or a functional fragment thereof, and may further comprise one or more mutations of the wild type "Forrest" FAD2-2B amino acid sequence (SEQ ID NO: 20) selected from the group consisting of: Q93*, C95Y, D154N, V156I, Q224H, A332T, P350L, and S373N.

In one embodiment, the polynucleotide encoding a FAD related promoter may comprise any wild type FAD2-2C promoter sequence, or a sequence at least 95% identical thereto, or a full length complement thereof, or a functional fragment thereof. For example, in one embodiment, the wild type FAD2-2C promoter sequence can comprise the wild type "Forrest" FAD2-2C promoter sequence (SEQ ID NO: 21). In some embodiments, the polynucleotide encoding a polypeptide having FAD activity may comprise any wild type FAD2-2C genomic or coding sequence, or a sequence at least 95% identical thereto, or a full length complement thereof, or a functional fragment thereof. In other embodiments, the wild type FAD2-2C coding sequence may comprise the wild type "Forrest" FAD2-2C coding sequence (SEQ ID NO: 22), or a sequence at least 95% identical thereto, or a full-length complement thereof, or a functional fragment thereof, and may further comprise one or more mutations of the wild type "Forrest" FAD2-2C coding sequence (SEQ ID NO: 22) selected from the group consisting of: G49A, C88T, G175A, C259T, C313A, C625T, A672T, G781A, G799A, and G1114A. In still further embodiments, the polypeptide having FAD activity may comprise the wild type "Forrest" FAD2-2C amino acid sequence (SEQ ID NO: 23), or a sequence at least 95% identical thereto, or a full-length complement thereof, or a functional fragment thereof, and may further comprise one or more mutations of the wild type "Forrest" FAD2-2C amino acid sequence (SEQ ID NO: 23) selected from the group consisting of: E17K, P30S, D59N, P87S, H105N, H209Y, Q224H, V261M, V267M, and E372K.

In one embodiment, the polynucleotide encoding a FAD related promoter may comprise any wild type FAD2-2D promoter sequence, or a sequence at least 95% identical thereto, or a full length complement thereof, or a functional fragment thereof. For example, in one embodiment, the wild type FAD2-2D promoter sequence can comprise the wild type "Forrest" FAD2-2D promoter sequence (SEQ ID NO: 24). In some embodiments, the polynucleotide encoding a polypeptide having FAD activity may comprise any wild type FAD2-2D genomic or coding sequence, or a sequence at least 95% identical thereto, or a full length complement thereof, or a functional fragment thereof. In other embodiments, the wild type FAD2-2D coding sequence may comprise the wild type "Forrest" FAD2-2D coding sequence (SEQ ID NO: 25), or a sequence at least 95% identical thereto, or a full-length complement thereof, or a functional fragment thereof, and may further comprise one or more mutations of the wild type "Forrest" FAD2-2D coding sequence (SEQ ID NO: 25) selected from the group consisting of: C439T, G510A, G579A, A622T, C643T, C751T, G905A, A1020T, and G1094T. In still further embodiments, the polypeptide having FAD activity may comprise the wild type "Forrest" FAD2-2D amino acid sequence (SEQ ID NO: 26), or a sequence at least 95% identical thereto, or a full-length complement thereof, or a functional fragment thereof, and may further comprise one or more mutations of the wild type "Forrest" FAD2-2D amino acid sequence (SEQ ID NO: 26) selected from the group consisting of: H147Y, W170*, W193*, R208*, P215S, L251F, R302K, K340N, and C365F.

In one embodiment, the polynucleotide encoding a FAD related promoter may comprise any wild type FAD2-2E promoter sequence, or a sequence at least 95% identical thereto, or a full length complement thereof, or a functional fragment thereof. For example, in one embodiment, the wild type FAD2-2E promoter sequence can comprise the wild type "Forrest" FAD2-2E promoter sequence (SEQ ID NO: 27). In some embodiments, the polynucleotide encoding a polypeptide having FAD activity may comprise any wild type FAD2-2E genomic or coding sequence, or a sequence at least 95% identical thereto, or a full length complement thereof, or a functional fragment thereof. In other embodiments, the wild type FAD2-2E coding sequence may comprise the wild type "Forrest" FAD2-2E coding sequence (SEQ ID NO: 28), or a sequence at least 95% identical thereto, or a full-length complement thereof, or a functional fragment thereof, and may further comprise one or more mutations of the wild type "Forrest" FAD2-2E coding sequence (SEQ ID NO: 28) selected from the group consisting of: G61A, T166A, C167T, G328A, G329A, C334T, C350T, C397T, C502T, T595A, G605A, G626A, G628A, C706T, G721A, G751A, G754A, A803T, and C829T. In still further embodiments, the polypeptide having FAD activity may comprise the wild type "Forrest" FAD2-2E amino acid sequence (SEQ ID NO: 29), or a sequence at least 95% identical thereto, or a full-length complement thereof, or a functional fragment thereof, and may further comprise one or more mutations of the wild type "Forrest" FAD2-2E amino acid sequence (SEQ ID NO: 29) selected from the group consisting of: A21T, S56F, S56T, G110E, G110R, P112S, A117V, L133F, P168S, W199R, G202E, R209K, D210N, H236Y, E241K, G251R, E252K, E268V, and P277S.

In one embodiment, the method of increasing oleic acid content of a soybean plant may comprise transforming the soybean plant with more than one polynucleotide encoding a FAD related promoter that functions in the soybean plant, provided that each polynucleotide encoding a FAD related promoter that functions in the soybean plant is operably linked to a polynucleotide encoding a polypeptide having FAD activity.

In certain embodiments, the more than one polynucleotide encoding a FAD related promoter may be selected from the group consisting of:
(i) any wild type FAD2-2A promoter sequence, or a sequence at least 95% identical thereto, or a full length complement thereof, or a functional fragment thereof, wherein the wild type FAD2-2A promoter sequence may be the wild type "Forrest" FAD2-2A promoter sequence (SEQ ID NO: 15), wherein the polynucleotide encoding a polypeptide having FAD activity comprises the wild type "Forrest" FAD2-2A coding sequence (SEQ ID NO: 16), or a sequence at least 95% identical thereto, or a full-length complement thereof, or a functional fragment thereof, and further comprises one or more mutations of the wild type "Forrest" FAD2-2A coding sequence (SEQ ID NO: 16) selected from the group consisting of: C38A, C91T, C103T, C134T, C211T, C245T, G283A, C331T, G346A, C376T, C379T, and G410T, wherein the polypeptide having FAD activity comprises the wild type "Forrest" FAD2-2A amino acid sequence (SEQ ID NO: 17), or a sequence at least 95% identical thereto, or a full-length complement thereof, or a functional fragment thereof, and further comprises one or more mutations of the wild type "Forrest" FAD2-2A amino acid sequence (SEQ ID NO: 17) selected from the group consisting of: P13H, R31C, R35C, T45I, P71S, A82V, A95T, H111Y, V116I, R126C, R127C, and R137L;
(ii) any wild type FAD2-2B promoter sequence, or a sequence at least 95% identical thereto, or a full length complement thereof, or a functional fragment thereof, wherein the wild type FAD2-2B promoter sequence may be the wild type "Forrest" FAD2-2B promoter sequence (SEQ ID NO: 18), wherein the polynucleotide encoding a polypeptide having FAD activity comprises the wild type "Forrest" FAD2-2B coding sequence (SEQ ID NO: 19), or a sequence at least 95% identical thereto, or a full-length complement thereof, or a functional fragment thereof, and further comprises one or more mutations of the wild type "Forrest" FAD2-2B coding sequence (SEQ ID NO: 19) selected from the group consisting of: C277T, G284A, G460A, G466A, A672T, G994A, C1049T, and G1118A, wherein the polypeptide having FAD activity comprises the wild type "Forrest" FAD2-2B amino acid sequence (SEQ ID NO: 20), or a sequence at least 95% identical thereto, or a full-length complement thereof, or a functional fragment thereof, and further comprises one or more mutations of the wild type "Forrest" FAD2-2B amino acid sequence (SEQ ID NO: 20) selected from the group consisting of: Q93*, C95Y, D154N, V156I, Q224H, A332T, P350L, and S373N;
(iii) any wild type FAD2-2C promoter sequence, or a sequence at least 95% identical thereto, or a full length complement thereof, or a functional fragment thereof, wherein the wild type FAD2-2C promoter sequence may be the wild type "Forrest" FAD2-2C promoter sequence (SEQ ID NO: 21), wherein the polynucleotide encoding a polypeptide having FAD activity comprises the wild type "Forrest" FAD2-2C coding sequence (SEQ ID NO: 22), or a sequence at least 95% identical thereto, or a full-length complement thereof, or a functional fragment thereof, and further comprises one or more mutations of the wild type "Forrest" FAD2-2C coding sequence (SEQ ID NO: 22) selected from the group consisting of: G49A, C88T, G175A, C259T, C313A, C625T, A672T, G781A, G799A, and G1114A, wherein the polypeptide having FAD activity comprises the wild type "Forrest" FAD2-2C amino acid sequence (SEQ ID NO: 23), or a sequence at least 95% identical thereto, or a full-length complement thereof, or a functional fragment thereof, and further comprises one or more mutations of the wild type "Forrest" FAD2-2C amino acid sequence (SEQ ID NO: 23)

selected from the group consisting of: E17K, P30S, D59N, P87S, H105N, H209Y, Q224H, V261M, V267M, and E372K;

(iv) any wild type FAD2-2D promoter sequence, or a sequence at least 95% identical thereto, or a full length complement thereof, or a functional fragment thereof, wherein the wild type FAD2-2D promoter sequence may be the wild type "Forrest" FAD2-2D promoter sequence (SEQ ID NO: 24), wherein the polynucleotide encoding a polypeptide having FAD activity comprises the wild type "Forrest" FAD2-2D coding sequence (SEQ ID NO: 25), or a sequence at least 95% identical thereto, or a full-length complement thereof, or a functional fragment thereof, and further comprises one or more mutations of the wild type "Forrest" FAD2-2D coding sequence (SEQ ID NO: 25) selected from the group consisting of: C439T, G510A, G579A, A622T, C643T, C751T, G905A, A1020T, and G1094T, wherein the polypeptide having FAD activity comprises the wild type "Forrest" FAD2-2D amino acid sequence (SEQ ID NO: 26), or a sequence at least 95% identical thereto, or a full-length complement thereof, or a functional fragment thereof, and further comprises one or more mutations of the wild type "Forrest" FAD2-2D amino acid sequence (SEQ ID NO: 26) selected from the group consisting of: H147Y, W170*, W193*, R208*, P215S, L251F, R302K, K340N, and C365F; and (v) any wild type FAD2-2E promoter sequence, or a sequence at least 95% identical thereto, or a full length complement thereof, or a functional fragment thereof, wherein the wild type FAD2-2E promoter sequence may be the wild type "Forrest" FAD2-2E promoter sequence (SEQ ID NO: 27), wherein the polynucleotide encoding a polypeptide having FAD activity comprises the wild type "Forrest" FAD2-2E coding sequence (SEQ ID NO: 28), or a sequence at least 95% identical thereto, or a full-length complement thereof, or a functional fragment thereof, and further comprises one or more mutations of the wild type "Forrest" FAD2-2E coding sequence (SEQ ID NO: 28) selected from the group consisting of: G61A, T166A, C167T, G328A, G329A, C334T, C350T, C397T, C502T, T595A, G605A, G626A, G628A, C706T, G721A, G751A, G754A, A803T, and C829T, wherein the polypeptide having FAD activity comprises the wild type "Forrest" FAD2-2E amino acid sequence (SEQ ID NO: 29), or a sequence at least 95% identical thereto, or a full-length complement thereof, or a functional fragment thereof, and further comprises one or more mutations of the wild type "Forrest" FAD2-2E amino acid sequence (SEQ ID NO: 29) selected from the group consisting of: A21T, S56F, S56T, G110E, G110R, P112S, A117V, L133F, P168S, W199R, G202E, R209K, D210N, H236Y, E241K, G251R, E252K, E268V, and P277S.

In one embodiment, the transformed soybean plant may have increased oleic acid content compared to a control soybean plant lacking the polynucleotide encoding a polypeptide having FAD activity as described above. For example, in one embodiment, the increased oleic acid content may comprise an at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, at least about 60%, at least about 70%, at least about 80%, at least about 90%, or at least about 100% increase in oleic acid content as compared to the control soybean plant lacking the polynucleotide encoding a polypeptide having FAD activity as described above.

DNA Constructs

Another embodiment of the present invention is a DNA construct comprising a polynucleotide encoding a fatty acid desaturase (FAD) related promoter that functions in a soybean plant operably linked to a polynucleotide encoding a polypeptide having FAD activity.

In one embodiment, the polynucleotide encoding a FAD related promoter may comprise any wild type FAD promoter sequence, or a sequence at least 95% identical thereto, or a full length complement thereof, or a functional fragment thereof. For example, in one embodiment, the wild type FAD promoter sequence can be selected from the group consisting of a promoter sequence of FAD2-2A, FAD2-2B, FAD2-2C, FAD2-2D, and FAD2-2E.

In one embodiment, the polynucleotide encoding a polypeptide having FAD activity may comprise any wild type FAD genomic or coding sequence, or a sequence at least 95% identical thereto, or a full length complement thereof, or a functional fragment thereof. For example, in one embodiment, the wild type FAD genomic or coding sequence can be selected from the group consisting of a genomic or coding sequence of FAD2-2A, FAD2-2B, FAD2-2C, FAD2-2D, and FAD2-2E.

In one embodiment, the polypeptide having FAD activity may comprise any wild type FAD sequence, or a sequence at least 95% identical thereto, or a full-length complement thereof, or a functional fragment thereof. For example, in one embodiment, the wild type FAD amino acid sequence can be selected from the group consisting of an amino acid sequence of FAD2-2A, FAD2-2B, FAD2-2C, FAD2-2D, and FAD2-2E.

In one embodiment, the polynucleotide encoding a FAD related promoter may comprise any wild type FAD2-2A promoter sequence, or a sequence at least 95% identical thereto, or a full length complement thereof, or a functional fragment thereof. For example, in one embodiment, the wild type FAD2-2A promoter sequence can comprise the wild type "Forrest" FAD2-2A promoter sequence (SEQ ID NO: 15). In some embodiments, the polynucleotide encoding a polypeptide having FAD activity may comprise any wild type FAD2-2A genomic or coding sequence, or a sequence at least 95% identical thereto, or a full length complement thereof, or a functional fragment thereof. In other embodiments, the wild type FAD2-2A coding sequence may comprise the wild type "Forrest" FAD2-2A coding sequence (SEQ ID NO: 16), or a sequence at least 95% identical thereto, or a full-length complement thereof, or a functional fragment thereof, and may further comprise one or more mutations of the wild type "Forrest" FAD2-2A coding sequence (SEQ ID NO: 16) selected from the group consisting of: C38A, C91T, C103T, C134T, C211T, C245T, G283A, C331T, G346A, C376T, C379T, and G410T. In still further embodiments, the polypeptide having FAD activity may comprise the wild type "Forrest" FAD2-2A amino acid sequence (SEQ ID NO: 17), or a sequence at least 95% identical thereto, or a full-length complement thereof, or a functional fragment thereof, and may further comprise one or more mutations of the wild type "Forrest" FAD2-2A amino acid sequence (SEQ ID NO: 17) selected from the group consisting of: P13H, R31C, R35C, T45I, P71S, A82V, A95T, H111Y, V116I, R126C, R127C, and R137L.

In one embodiment, the polynucleotide encoding a FAD related promoter may comprise any wild type FAD2-2B promoter sequence, or a sequence at least 95% identical thereto, or a full length complement thereof, or a functional fragment thereof. For example, in one embodiment, the wild type FAD2-2B promoter sequence can comprise the wild type "Forrest" FAD2-2B promoter sequence (SEQ ID NO: 18). In some embodiments, the polynucleotide encoding a polypeptide having FAD activity may comprise any wild type FAD2-2B genomic or coding sequence, or a sequence at least 95% identical thereto, or a full length complement thereof, or a functional fragment thereof. In other embodiments, the wild type FAD2-2B coding sequence may comprise the wild type "Forrest" FAD2-2B coding sequence (SEQ ID NO: 19), or a sequence at least 95% identical thereto, or a full-length complement thereof, or a functional fragment thereof, and may further comprise one or more mutations of the wild type "Forrest" FAD2-2B coding sequence (SEQ ID NO: 19) selected from the group consisting of: C277T, G284A, G460A, G466A, A672T, G994A, C1049T, and G1118A. In still further embodiments, the polypeptide having FAD activity may comprise the wild type "Forrest" FAD2-2B amino acid sequence (SEQ ID NO: 20), or a sequence at least 95% identical thereto, or a full-length complement thereof, or a functional fragment thereof, and may further comprise one or more mutations of the wild type "Forrest" FAD2-2B amino acid sequence (SEQ ID NO: 20) selected from the group consisting of: Q93*, C95Y, D154N, V156I, Q224H, A332T, P350L, and S373N.

In one embodiment, the polynucleotide encoding a FAD related promoter may comprise any wild type FAD2-2C promoter sequence, or a sequence at least 95% identical thereto, or a full length complement thereof, or a functional fragment thereof. For example, in one embodiment, the wild type FAD2-2C promoter sequence can comprise the wild type "Forrest" FAD2-2C promoter sequence (SEQ ID NO: 21). In some embodiments, the polynucleotide encoding a polypeptide having FAD activity may comprise any wild type FAD2-2C genomic or coding sequence, or a sequence at least 95% identical thereto, or a full length complement thereof, or a functional fragment thereof. In other embodiments, the wild type FAD2-2C coding sequence may comprise the wild type "Forrest" FAD2-2C coding sequence (SEQ ID NO: 22), or a sequence at least 95% identical thereto, or a full-length complement thereof, or a functional fragment thereof, and may further comprise one or more mutations of the wild type "Forrest" FAD2-2C coding sequence (SEQ ID NO: 22) selected from the group consisting of: G49A, C88T, G175A, C259T, C313A, C625T, A672T, G781A, G799A, and G1114A. In still further embodiments, the polypeptide having FAD activity may comprise the wild type "Forrest" FAD2-2C amino acid sequence (SEQ ID NO: 23), or a sequence at least 95% identical thereto, or a full-length complement thereof, or a functional fragment thereof, and may further comprise one or more mutations of the wild type "Forrest" FAD2-2C amino acid sequence (SEQ ID NO: 23) selected from the group consisting of: E17K, P30S, D59N, P87S, H105N, H209Y, Q224H, V261M, V267M, and E372K.

In one embodiment, the polynucleotide encoding a FAD related promoter may comprise any wild type FAD2-2D promoter sequence, or a sequence at least 95% identical thereto, or a full length complement thereof, or a functional fragment thereof. For example, in one embodiment, the wild type FAD2-2D promoter sequence can comprise the wild type "Forrest" FAD2-2D promoter sequence (SEQ ID NO: 24). In some embodiments, the polynucleotide encoding a polypeptide having FAD activity may comprise any wild type FAD2-2D genomic or coding sequence, or a sequence at least 95% identical thereto, or a full length complement thereof, or a functional fragment thereof. In other embodiments, the wild type FAD2-2D coding sequence may comprise the wild type "Forrest" FAD2-2D coding sequence (SEQ ID NO: 25), or a sequence at least 95% identical thereto, or a full-length complement thereof, or a functional fragment thereof, and may further comprise one or more mutations of the wild type "Forrest" FAD2-2D coding sequence (SEQ ID NO: 25) selected from the group consisting of: C439T, G510A, G579A, A622T, C643T, C751T, G905A, A1020T, and G1094T. In still further embodiments, the polypeptide having FAD activity may comprise the wild type "Forrest" FAD2-2D amino acid sequence (SEQ ID NO: 26), or a sequence at least 95% identical thereto, or a full-length complement thereof, or a functional fragment thereof, and may further comprise one or more mutations of the wild type "Forrest" FAD2-2D amino acid sequence (SEQ ID NO: 26) selected from the group consisting of: H147Y, W170*, W193*, R208*, P215S, L251F, R302K, K340N, and C365F.

In one embodiment, the polynucleotide encoding a FAD related promoter may comprise any wild type FAD2-2E promoter sequence, or a sequence at least 95% identical thereto, or a full length complement thereof, or a functional fragment thereof. For example, in one embodiment, the wild type FAD2-2E promoter sequence can comprise the wild type "Forrest" FAD2-2E promoter sequence (SEQ ID NO: 27). In some embodiments, the polynucleotide encoding a polypeptide having FAD activity may comprise any wild type FAD2-2E genomic or coding sequence, or a sequence at least 95% identical thereto, or a full length complement thereof, or a functional fragment thereof. In other embodiments, the wild type FAD2-2E coding sequence may comprise the wild type "Forrest" FAD2-2E coding sequence (SEQ ID NO: 28), or a sequence at least 95% identical thereto, or a full-length complement thereof, or a functional fragment thereof, and may further comprise one or more mutations of the wild type "Forrest" FAD2-2E coding sequence (SEQ ID NO: 28) selected from the group consisting of: G61A, T166A, C167T, G328A, G329A, C334T, C350T, C397T, C502T, T595A, G605A, G626A, G628A, C706T, G721A, G751A, G754A, A803T, and C829T. In still further embodiments, the polypeptide having FAD activity may comprise the wild type "Forrest" FAD2-2E amino acid sequence (SEQ ID NO: 29), or a sequence at least 95% identical thereto, or a full-length complement thereof, or a functional fragment thereof, and may further comprise one or more mutations of the wild type "Forrest" FAD2-2E amino acid sequence (SEQ ID NO: 29) selected from the group consisting of: A21T, S56F, S56T, G110E, G110R, P112S, A117V, L133F, P168S, W199R, G202E, R209K, D210N, H236Y, E241K, G251R, E252K, E268V, and P277S.

In one embodiment, the DNA construct may comprise more than one polynucleotide encoding a FAD related promoter that functions in a soybean plant, provided that each polynucleotide encoding a FAD related promoter that functions in a soybean plant is operably linked to a polynucleotide encoding a polypeptide having FAD activity.

In some embodiments, the more than one polynucleotide encoding a FAD related promoter may be selected from the group consisting of:

(i) any wild type FAD2-2A promoter sequence, or a sequence at least 95% identical thereto, or a full length complement thereof, or a functional fragment thereof, wherein the wild type FAD2-2A promoter sequence may be the wild type "Forrest" FAD2-2A promoter sequence (SEQ ID NO: 15), wherein the polynucleotide encoding a polypeptide having FAD activity comprises the wild type "Forrest" FAD2-2A coding sequence (SEQ ID NO: 16), or a sequence at least 95% identical thereto, or a full-length complement thereof, or a functional fragment thereof, and further comprises one or more mutations of the wild type "Forrest" FAD2-2A coding sequence (SEQ ID NO: 16) selected from the group consisting of: C38A, C91T, C103T, C134T, C211T, C245T, G283A, C331T, G346A, C376T, C379T, and G410T, wherein the polypeptide having FAD activity comprises the wild type "Forrest" FAD2-2A amino acid sequence (SEQ ID NO: 17), or a sequence at least 95% identical thereto, or a full-length complement thereof, or a functional fragment thereof, and further comprises one or more mutations of the wild type "Forrest" FAD2-2A amino acid sequence (SEQ ID NO: 17) selected from the group consisting of: P13H, R31C, R35C, T45I, P71S, A82V, A95T, H111Y, V116I, R126C, R127C, and R137L;

(ii) any wild type FAD2-2B promoter sequence, or a sequence at least 95% identical thereto, or a full length complement thereof, or a functional fragment thereof, wherein the wild type FAD2-2B promoter sequence may be the wild type "Forrest" FAD2-2B promoter sequence (SEQ ID NO: 18), wherein the polynucleotide encoding a polypeptide having FAD activity comprises the wild type "Forrest" FAD2-2B coding sequence (SEQ ID NO: 19), or a sequence at least 95% identical thereto, or a full-length complement thereof, or a functional fragment thereof, and further comprises one or more mutations of the wild type "Forrest" FAD2-2B coding sequence (SEQ ID NO: 19) selected from the group consisting of: C277T, G284A, G460A, G466A, A672T, G994A, C1049T, and G1118A, wherein the polypeptide having FAD activity comprises the wild type "Forrest" FAD2-2B amino acid sequence (SEQ ID NO: 20), or a sequence at least 95% identical thereto, or a full-length complement thereof, or a functional fragment thereof, and further comprises one or more mutations of the wild type "Forrest" FAD2-2B amino acid sequence (SEQ ID NO: 20) selected from the group consisting of: Q93*, C95Y, D154N, V156I, Q224H, A332T, P350L, and S373N;

(iii) any wild type FAD2-2C promoter sequence, or a sequence at least 95% identical thereto, or a full length complement thereof, or a functional fragment thereof, wherein the wild type FAD2-2C promoter sequence may be the wild type "Forrest" FAD2-2C promoter sequence (SEQ ID NO: 21), wherein the polynucleotide encoding a polypeptide having FAD activity comprises the wild type "Forrest" FAD2-2C coding sequence (SEQ ID NO: 22), or a sequence at least 95% identical thereto, or a full-length complement thereof, or a functional fragment thereof, and further comprises one or more mutations of the wild type "Forrest" FAD2-2C coding sequence (SEQ ID NO: 22) selected from the group consisting of: G49A, C88T, G175A, C259T, C313A, C625T, A672T, G781A, G799A, and G1114A, wherein the polypeptide having FAD activity comprises the wild type "Forrest" FAD2-2C amino acid sequence (SEQ ID NO: 23), or a sequence at least 95% identical thereto, or a full-length complement thereof, or a functional fragment thereof, and further comprises one or more mutations of the wild type "Forrest" FAD2-2C amino acid sequence (SEQ ID NO: 23) selected from the group consisting of: E117K, P30S, D59N, P87S, H105N, H209Y, Q224H, V261M, V267M, and E372K;

(iv) any wild type FAD2-2D promoter sequence, or a sequence at least 95% identical thereto, or a full length complement thereof, or a functional fragment thereof, wherein the wild type FAD2-2D promoter sequence may be the wild type "Forrest" FAD2-2D promoter sequence (SEQ ID NO: 24), wherein the polynucleotide encoding a polypeptide having FAD activity comprises the wild type "Forrest" FAD2-2D coding sequence (SEQ ID NO: 25), or a sequence at least 95% identical thereto, or a full-length complement thereof, or a functional fragment thereof, and further comprises one or more mutations of the wild type "Forrest" FAD2-2D coding sequence (SEQ ID NO: 25) selected from the group consisting of: C439T, G510A, G579A, A622T, C643T, C751T, G905A, A1020T, and G1094T, wherein the polypeptide having FAD activity comprises the wild type "Forrest" FAD2-2D amino acid sequence (SEQ ID NO: 26), or a sequence at least 95% identical thereto, or a full-length complement thereof, or a functional fragment thereof, and further comprises one or more mutations of the wild type "Forrest" FAD2-2D amino acid sequence (SEQ ID NO: 26) selected from the group consisting of: H147Y, W170*, W193*, R208*, P215S, L251F, R302K, K340N, and C365F; and (v) any wild type FAD2-2E promoter sequence, or a sequence at least 95% identical thereto, or a full length complement thereof, or a functional fragment thereof, wherein the wild type FAD2-2E promoter sequence may be the wild type "Forrest" FAD2-2E promoter sequence (SEQ ID NO: 27), wherein the polynucleotide encoding a polypeptide having FAD activity comprises the wild type "Forrest" FAD2-2E coding sequence (SEQ ID NO: 28), or a sequence at least 95% identical thereto, or a full-length complement thereof, or a functional fragment thereof, and further comprises one or more mutations of the wild type "Forrest" FAD2-2E coding sequence (SEQ ID NO: 28) selected from the group consisting of: G61A, T166A, C167T, G328A, G329A, C334T, C350T, C397T, C502T, T595A, G605A, G626A, G628A, C706T, G721A, G751A, G754A, A803T, and C829T, wherein the polypeptide having FAD activity comprises the wild type "Forrest" FAD2-2E amino acid sequence (SEQ ID NO: 29), or a sequence at least 95% identical thereto, or a full-length complement thereof, or a functional fragment thereof, and further comprises one or more mutations of the wild type "Forrest" FAD2-2E amino acid sequence (SEQ ID NO: 29) selected from the group consisting of: A21T, S56F, S56T, G110E, G110R, P112S, A117V, L133F, P168S, W199R, G202E, R209K, D210N, H236Y, E241K, G251R, E252K, E268V, and P277S.

Cultivars and Additional Agronomically Desirable Traits

In addition to a soybean cultivar with the wild type "Forrest" genome as references above, other cultivars may be employed with the present invention. Cultivars compatible with the present invention include any cultivar with a corresponding FAD polypeptide sequence containing the same wild type amino acid residues as the starting amino acids listed in the above mutations. For example, a cultivar would be suitable if it contained a histidine residue at position 111 in the FAD2-2A polypeptide so that the listed mutation H111Y would make sense in the context of the wild type FAD2-2A sequence for that cultivar, and so on for each mutation described above.

Additionally, the mutations described above, along with the compositions and methods described above, may be employed with other existing technologies regarding cultivars with agronomically desirable traits, such as pest resistance and yield.

"Forrest" is a soybean cultivar that belongs to the Maturity Group V with resistance to several soybean pathogens including Soybean Cyst Nematode (SCN), Sudden Death Syndrome (SDS), and Reniform nematode. Because it's a cultivar, Forrest could be easily used for breeding purposes to introgress the high oleic acid content trait into high-yielding lines without compromising their agronomic performance while transferring its package of resistance.

Sequences and Mutations

The amino acid sequences and nucleic acid sequences described herein may contain various mutations. Mutations may include insertions, substitutions, and deletions. Insertions are written as follows: (+)(amino acid/nucleic acid sequence position number)(inserted amino acid/nucleic acid base). For example, +287A would mean an insertion of an alanine residue after position 287 in the corresponding amino acid sequence. Substitutions are written as follows: (amino acid/nucleic acid base to be replaced)(amino acid/nucleic acid sequence position number)(substituted amino acid/nucleic acid base). For example, C1082A would mean a substitution of an adenine base instead of a cytosine base at position 1082 in the corresponding nucleic acid sequence. "*" is used to indicate a mutation that results in a premature stop in an amino acid sequence. Deletions are written as follows: (amino acid/nucleic acid base to be deleted)(amino acid/nucleic acid sequence position number)(−). For example, C970− would mean a deletion of the cytosine base normally located at position 970 in the corresponding nucleic acid sequence.

The amino acid sequences and nucleic acid sequences described herein may contain mutations at various sequence positions. Sequence positions may be written a variety of ways for convenience. More specifically, sequence positions may be written from either the beginning of the sequence as a positive position number, or from the end of the sequence as a negative number. Sequence positions may be converted easily between a positive notation and a negative notation by comparing to the sequence length and either adding or subtracting the sequence length. For example, a promoter containing 10 nucleic acid bases with a mutation from cytosine to adenine at the second position from the start of the sequence may be written as C2A. Alternatively, this mutation may be written as C(−9)A, −9C/A, or in a similar fashion denoting the negative position number.

Definitions and Alternate Embodiments

The following definitions and methods are provided to better define the present invention and to guide those of ordinary skill in the art in the practice of the present invention. Unless otherwise noted, terms are to be understood according to conventional usage by those of ordinary skill in the relevant art.

The term "agronomically elite" refers to a genotype that has a culmination of many distinguishable traits such as emergence, vigor, vegetative vigor, disease resistance, seed set, standability, and threshability, which allows a producer to harvest a product of commercial significance.

An "allele" refers to one of two or more alternative forms of a genomic sequence at a given locus on a chromosome.

The term "chimeric" is understood to refer to the product of the fusion of portions of two or more different polynucleotide molecules. "Chimeric promoter" is understood to refer to a promoter produced through the manipulation of known promoters or other polynucleotide molecules. Such chimeric promoters can combine enhancer domains that can confer or modulate gene expression from one or more promoters or regulatory elements, for example, by fusing a heterologous enhancer domain from a first promoter to a second promoter with its own partial or complete regulatory elements. Thus, the design, construction, and use of chimeric promoters according to the methods disclosed herein for modulating the expression of operably linked polynucleotide sequences are encompassed by the present invention.

Novel chimeric promoters can be designed or engineered by a number of methods. For example, a chimeric promoter may be produced by fusing an enhancer domain from a first promoter to a second promoter. The resultant chimeric promoter may have novel expression properties relative to the first or second promoters. Novel chimeric promoters can be constructed such that the enhancer domain from a first promoter is fused at the 5' end, at the 3' end, or at any position internal to the second promoter.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A construct of the present invention can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule, which can play an important role in translation initiation and can also be a genetic component in an expression construct. These additional upstream and downstream regulatory nucleic acid molecules may be derived from a source that is native or heterologous with respect to the other elements present on the promoter construct.

"Expression vector", "vector", "expression construct", "vector construct", "plasmid", or "recombinant DNA construct" is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

The term "genotype" means the specific allelic makeup of an organism.

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m = 81.5°$ C.$+16.6(\log_{10}[Na^{+1}])+0.41$(fraction G/C content)$-0.63$(% formamide)$-(600/l)$. Furthermore, the $T_m$ of a DNA:DNA hybrid is decreased by 1-1.5° C. for every 1% decrease in nucleotide identity.

The term "introgressed," when used in reference to a genetic locus, refers to a genetic locus that has been introduced into a new genetic background. Introgression of a genetic locus can thus be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

The term "linked," when used in the context of nucleic acid markers and/or genomic regions, means that the markers and/or genomic regions are located on the same linkage group or chromosome.

A "marker" means a detectable characteristic that can be used to discriminate between organisms. Examples of such characteristics include, but are not limited to, genetic markers, biochemical markers, metabolites, morphological characteristics, and agronomic characteristics.

A "marker gene" refers to any transcribable nucleic acid molecule whose expression can be screened for or scored in some way.

Certain genetic markers useful in the present invention include "dominant" or "codominant" markers. "Codominant" markers reveal the presence of two or more alleles (two per diploid individual). "Dominant" markers reveal the presence of only a single allele. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominantly dimorphic, dominant and codominant markers can be equally valuable. As populations become more heterozygous and multiallelic, codominant markers often become more informative of the genotype than dominant markers.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

The term "phenotype" means the detectable characteristics of a cell or organism that can be influenced by gene expression.

The term "plant" can include plant cells, plant protoplasts, plant cells of tissue culture from which a plant can be regenerated, plant calli, plant clumps and plant cells that are intact in plants or parts of plants such as pollen, flowers, seeds, leaves, stems, and the like. Each of these terms can apply to a soybean "plant". Plant parts (e.g., soybean parts) include, but are not limited to, pollen, seeds, flowers, stems, roots, leaves, ovules, and cells.

The term "population" means a genetically heterogenous collection of organisms that share a common parental derivation.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the transcription start site, such as, in the case of a polymerase II type promoter, a TATA element. A promoter can optionally include distal enhancer or repressor elements, which can be located as much as several thousand base pairs from the start site of transcription.

A "genomic sequence" is a DNA sequence as it is found in the DNA of an organism. It can include introns.

A "coding sequence" is a DNA sequence that includes only nucleotides that encode amino acids in a particular protein. It does not include introns.

A "quantitative trait locus (QTL)" is a chromosomal location that encodes for alleles that affect the expressivity of a phenotype.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present invention, conventional compositions and methods for preparing and using constructs and host cells are well known.

The "transcription start site" or "initiation site" is the position surrounding a nucleotide that is part of the transcribed sequence, which is also defined as position+1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) can be denominated as negative.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a plant into which a heterologous nucleic acid molecule has been introduced. The nucleic acid molecule can be stably integrated into the genome as generally known in the art. Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

The terms "variety" and "cultivar" mean a group of similar plants that by their genetic pedigrees and performance can be identified from other varieties within the same species.

"Wild-type" refers to a virus or organism, or any of their components, found in nature without any known mutation.

In some embodiments, numbers expressing quantities of ingredients, properties such as molecular weight, reaction conditions, and so forth, used to describe and claim certain embodiments of the present invention are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present invention are approximations, the numerical values set forth in the specific examples are reported as precisely as practicable. The numerical values presented in some embodiments of the present invention may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

In some embodiments, the terms "a" and "an" and "the" and similar references used in the context of describing a particular embodiment (especially in the context of certain of the following claims) can be construed to cover both the singular and the plural, unless specifically noted otherwise. When used in conjunction with the word "comprising" or other open language in the claims, the words "a" and "an" denote "one or more," unless specifically noted.

In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present invention and does not pose a limitation on the scope of the present invention otherwise claimed. No language in the specification should be construed as indicating any non-claimed element essential to the practice of the present invention.

Groupings of alternative elements or embodiments of the present invention disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

Having described the present invention in detail, it will be apparent that all of the compositions and methods disclosed and claimed herein can be made and executed without undue experimentation in light of the present invention. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Furthermore, it should be appreciated that all examples in the present invention are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the present invention, and this can be considered to constitute examples of modes for its practice. However, those of skill in the art should, in light of the present invention, appreciate that many changes can be made in the specific embodiments that are disclosed and still obtain a like or similar result without departing from the spirit and scope of the present invention.

Using a novel technology; TILLING-by-Sequencing+, we functionally characterized the five members of the GmFAD2-2 subfamily. The identified mutations showed the presence of a positive impact on increasing soybean seed oleic acid content. Subcellular localization indicated that members of the two GmFAD2-2 subfamily are located in cellular compartments different from those previously reported for the traditional GmFAD2-1s, suggesting the presence of an alternative pathway to convert oleic acid to linoleic acid in soybeans without substantially altering the traditional plastidial/ER fatty acid production. The isolated soybean TILLING mutants from this study can be used in soybean breeding programs to improve seed fatty acid composition trait.

Besides the soybean fatty acid desaturase (GmFAD2-1) subfamily, the GmFAD2-2 subfamily is composed of five members, including GmFAD2-2A, GmFAD2-2B, GmFAD2-2C, GmFAD2-2D, and GmFAD2-2E. Segmental duplication of GmFAD2-1A/GmFAD2-1B, GmFAD2-2A/GmFAD2-2C, GmFAD2-2A/GmFAD2-2D, and GmFAD2-2D/GmFAD2-2C have occurred about 10.65, 27.04, 100.81, and 106.55 Mya, respectively. Using TILLING-by-Sequencing+technology, we successfully identified 12, 8, 11, 9, and 19 EMS mutants at the GmFAD2-2A, GmFAD2-2B, GmFAD2-2C, GmFAD2-2D, and GmFAD2-2E genes, respectively. Functional analyses of newly identified mutants revealed unprecedented role of the five GmFAD2-2A, GmFAD2-2B, GmFAD2-2C, GmFAD2-2D, and GmFAD2-2E members in controlling the seed oleic acid content. Most importantly, unlike GmFAD2-1 members, subcellular localization revealed that members of the GmFAD2-2 subfamily showed a cytoplasmic localization, which may suggest the presence of an alternative fatty acid desaturase pathway in soybean for converting oleic acid content without substantially altering the traditional plastidial/ER fatty acid production.

The wild type "Forrest" sequences for FAD2-2 family members are shown in Table 1.

TABLE 1

Wild Type "Forrest" Sequences for FAD2-2 Family Members

| SEQ ID NO: | Sequence Description | Sequence |
|---|---|---|
| 15 | FAD2-2A promoter | ATATTTTAAGTGATGCGTGAGTGAATGCTTCTCTCTAAAGGAA GGAAGAGAATGTAAAAAATCTATACTCACAAGAGAATAAGGA AAATAAGTTTCATTTTTAAGTTTGTCCCACATAGGACATCTTGC AGTTGGGTACGCCTATGCATTTATTTACACGAAAATGTTGTGC TGCGCTGTTAATTGGACCACAAACATGCAACGTACATGCAATC AAAATTGCTGTTCACTAGGGAGATAATTCTCGCCATAAGTTCC TGTGGCTGTGGCTGTGGCTGTGACACATTTAGTGCATATTAAA ATTTTCATTCATAAGTTTGGATTAAATTTAAATTTGCAAATTGA ATTTGTAGAAAGAACCCAAATCTTTTATATATAAAACTCAGTT TCAGGAAAAACTTTAATGCACAAACTTTGTTTTAAAAGGTAAT CAACATGTTACAAAATCGAATTAATTTTCGAATAGTTTTTAGC ACCAAACAGTATTTTTTTTTTAGAAATAACATCTTTAATGATCA AAACTTAAAGATATCTATTTTTATTATCTTTAGAGTATATTAAA TTATTTTTATTTTTAAGAAATTTTAGAGATGAGTTGTTTATTAA GATACTCAAGTCAAAACTGAAGAAATCCACCATGCTTAATTCA CAATGCTTAACTGGATTTATCCAACAACAAAAGAAAATAAAA AATTACTTTTTTCTCCTAAGAAACTCATCAAGCATCTTTCATTG GAGATGACTTAACTTTCTTTGAAAGAAAAGAGACGACAATAAT CATGGTGGTCCGGGTTTTTTAAACGCAATGTGTTTAGAAAGTG ATATATATGGCTTTTTTATAATTATTTTGTTAACTTATTTCATTA AGCTTTAGGATTATTATTATATATAAAAATTACTTTATTTCAAT ATCAATTACAATTACAATAATGCCACATTATGTTTTATGTACG ACGATGTTGTAAGTTGGTGTTGTCCAAGTACTTAATTAAATTAT TGAGTACTAGTAACCCAGTTTTTCATATACACTCTCTTATTGGT TAAAATATATTAAAAACTATAAAATCAAGTAAGAGAATTATTA AAAATTATGTGAGATCCTCTTAATTTTATAATTTTTAATAAATT TTAACCAACAAAAAACCGTGTTACACCTTTCATAACAATTTTG AATGAATTTATTTTAAAAGTATTGGTGTTAAAATTTTGATTTTA GAAGAATTAGATAAATAAATTAATGTATATTTATTATTTGGAA GCGTTTTAAAAGTGACGTTTAAAAGAGTTGATCAATTTTGTTT ACAGATCTGGATAATGTTGCATGTTTATTCTTCTCAATTGTAAA TTTTCTTTTTTGTGCACGGGGATTTATTTTTAATTTAGATAAGA CAAATTAAGCTTTCAGAACATCACCCTTGTCCAATTCATTTTAG TTTCTGATCATGGTGTAAAATCTAACTAAGTTGGTTTGGGCAA GAGAAATGGTCCCTATGCTTAAGTCATTCTAGGACGAAAATAA AAATATAACAGGGTAAAGCATATCCCTGATAGCGTGTGTCTAT |

TABLE 1-continued

Wild Type "Forrest" Sequences for FAD2-2 Family Members

| SEQ ID NO: | Sequence Description | Sequence |
|---|---|---|
| | | TGTTTTCTCATTCCTCCTCGGTCACGAAAACCAACTAATTCTTT<br>TTGCCACGATTAAATAATTAATCTGTGTGTTAATTATAATGAC<br>GAGTAGGGTTATCTTTCCCTTTATCCTCAGGAGTGTGGAAATG<br>AAAATTAATGAACTAGCTAGAAAACGATAATGAGAAGAACCT<br>CTCAGCTACTATATATTTATGAAATGTTAATTTATTCCAGACAC<br>GTGAGTATATATTATACATTATTTTTTAATGAATGCAATTTTTG<br>CTTTGAAGTGCACACACACGGTTCATTCTAATTCTGATACCTGT<br>ATGCTTTAGAATGAATAAGGTTAATTAGGTAACTAGCTATTAC<br>TGATCATAATCCTTGATTTAAGGTCAATTATAGTCTTGTTCATG<br>TGTTCATGAAAAGTGCATGGTGTTAATAAAATGCAGGTTGTGT<br>AAAG |
| 16 | FAD2-2A coding sequence | ATGGGTGACACTATGAAACGGGTGCCAATTGAAAAACCTCCAT<br>TTACTCTCAGCCAAATCAAGAAGGCTATTCCACCACACTTTTTC<br>CAGCGTTCTGTTCTGCGCTCATTCTCGTATCTCATTTATGACCT<br>TACCATAGCCTTCTGCCTCTATTACATTGCCACCAATTACTTCC<br>ACAACCTTCCTCATCCTCTCACTTTCTTGGCATGGCCAATCTAT<br>TGGGCTGTGCAAGGATTCACCCTAGCTGGTCTTTGGGTCATTG<br>CACATGACTGTGGCCACCATGCATTCAGAGATTTCCAACTTCT<br>TGATGATAACGTTGGCCTTGTTCTCCACTCTGCTCTATTAGTCC<br>CATACTTTTCATGGAAATACAGCCATCGCCGTCACCACTCCAA<br>CACAGGTTCTCTTGAGCGAGATGAAGTGTTTGTACCAAAGCAG<br>AAGTCTAGCACACATGTGGTGCATCACTTGTTCTCCACAATGC<br>CACATTATCATGCAATGGACGCTACAAAGGCAATAAAGCCCAT<br>TTTGGGAGAGTATTATCGATTTGACGAGACCCCATTTGTCAAG<br>GCAATGTGGAGAGAGGCAAGAGAGTGTATTTATGTGGAACCA<br>GATACTGAGAACAAAGGTGTATTTTGGTACAACAATAAGTTGT<br>GA |
| 17 | FAD2-2A polypeptide amino acid sequence | MGDTMKRVPIEKPPFTLSQIKKAIPPHFFQRSVLRSFSYLIYDLTIA<br>FCLYYIATNYFHNLPHPLTFLAWPIYWAVQGFTLAGLWVIAHDC<br>GHHAFRDFQLLDDNVGLVLHSALLVPYFSWKYSHRRHHSNTGSL<br>ERDEVFVPKQKSSTHVVHHLFSTMPHYHAMDATKAIKPILGEYY<br>RFDETPFVKAMWREARECIYVEPDTENKGVFWYNNKL |
| 18 | FAD2-2B promoter | ACCTGGCTGTTTAGCGCTATCTGCATATTTCCGTGACGCATCTC<br>TATCGGATCTAAGGAGGAATCTCCTTTTTCCTCCGTGTCATTTG<br>TTGTATTTATTGTTCTGTGCTAATACTTCAGAAAATGGCTGCAT<br>TGTGTTCTTCTTTGCTGTATTAAGTGTTTGTGTTGTGAATCTGG<br>AAGCGATTTTGCGTGACGTAACTTGCGTCTTCTACTATTCTCTT<br>TCAGATCTCATTCACTGTTCCTCTTTGATGTTTTTTTTGCTTAC<br>TAAGCCTATTTAATGATATTCTTTACAAATAGTTAGTGGACTAT<br>TTGGTTGGTTGGTGAGTTATGAATATTCGTATTCTCTACCACAA<br>GTTGGGTTAAAAAATCTCTGCAACTCCACGAGGATATGTTTTT<br>TATTGTTTAGAGAAAATTACTCTTTCTTCCTTCCTTTTCAAATT<br>ACACGTTTTGCATCATTTGTTTTGAAATATATACTTTATGAATA<br>TAATAAGTTATATTGTGATTATTTTTAAATTGATGAATACTTAT<br>GAATGTTTGTCAATATTTTTTCTTGCCATTAATTAATCTTGAA<br>CATGTTATTGATATCTCTGATCTATATTTTGTCCTGATTTTAGT<br>ATTTTAGAACGAAGAATAAAATTTTATATTTTTTATTATCAATT<br>TTGAGCCATCAAAATAATTTTCAAAAATTATTTTAACCATCAA<br>AATTAATTTTGTCAACCCATCCTACAAGGCGTTTAACTTAATCA<br>TTATATTTGCTTGGGTGAAGTGAGAAAACAAGGAAGAAAATA<br>TTAAAAACTAGCAGAGAAGTTAAAGATAATTTCTCCCTTATTA<br>TTTAGATAAAGAGAAATGGAAGAAAATAAAATAACACTGCC<br>TATTATCTCATTTGTTTAAAAAACAATGAAAGCATATAACTAT<br>ATAAAATACAGTACTATAACTGAGCCAAGAACATATTTTGTCG<br>TCTGAGTAACTTTTTCTTTTGCTTGTTACGCTTTCTCCGCCGATG<br>CAGAAGGAGTATATGTTTGTGTTTTATGTTTTGAAAGATTCAAT<br>CCCCGGTTTTAAAGATAAATACAGTATGTTTTATTTAAAAGAAT<br>TAGTAGTTTTTTTAATATGTTTATTATTAGGCGTGCAGACTACT<br>ACAACTAACCGCAATAATTTTTTAATATTTTCTTCACAATAAAA<br>TTGTTTTCGTTTTTTCTAACGGTTTACGACACGTAATGGGTTTT<br>GAACTTGAGAACGTGCAAATAATCTAAACTCCTTCTGGTTGAG<br>TAACGAAGTGAAGAACCAATTATAATTTGTAAATACTTGAGTA<br>AGAGTTCGTGCATAAATTGGTTTTTATCAGTTTTTTCCACAAAA<br>TTATGATTTCCTGATATTTAAAAATAAATAAATAACTATATTCC<br>GTAAGTCGTACACAGTTATATTCAGCAAATAAATTATATTTAA<br>TAATTATTATCTTAAAAGTTACTTAAGAACTTGGTAAAAATAT<br>TTTTGTTTGAAAAAGTATATGATAAAAGTTTACGATAATGTAA<br>CTCGTGCTTAGCTGTTCCTAATTTCTGTAACAAAAAAAAAGT<br>TTCTTATTTGAAATTTGTAAATTTCCGGGTCATGTTAAGAAAAT<br>CTTGTAGACGAAAAGCCGGCCTATTGCATGCACCGATCATTGA<br>TTACTAGATACGGAAAACGACTCAATTAATTTAATATGAGATG |

TABLE 1-continued

Wild Type "Forrest" Sequences for FAD2-2 Family Members

| SEQ ID NO: | Sequence Description | Sequence |
|---|---|---|
| | | CGGACCGATCACTAGAGATGCTTCGTTCAACATATTTGATATT GCCAATATTGGCCATCCCTCTCATCATTATTGTTTATTTATTTG TAACATCACATATTCTTGTGGGTCCGCTTAGGATTAGGTGTTTG TTGCAAAAAATACAAAAAAAAATCTGTGGAACAAGGATCAAC ATATATTGTTTGTTTAATTGATTGATTGATTAGTTTGCAAGCTG TATTTTATAATTTAATTTAATTCAACTTTTGTTTTTTAGTTAAAA TTGTTTTTATTTTACTTATTCTGAAAACAAATTTATTCTACGCA GTGAATCAAATGACAATTTTAAACACACAATATAGCATAATCG ACAAATCAATTTTGAGTTTCTTTATCATTTTCTTTATTTATTGAC ATATTTGCACTTTCTGCAAAGACTCTGACTCGTGGTAGATATA GGGAAGGTTATAGAAGTTAGTGTAGTGTCATATCTAGCTATTT TTGCTTATTGGAAAAAGCCTTCCCTTTGTTTACAGATCTGGATA AGGTTGCATGCTTATTTTTCTCAACTGTGAATGGTTATTTCTTT GCATTTTTGTTTTGTTTTGGTTATGGGATTAATTTTTTAATTA CGAAGAAGCTTTTAGAGCATCACCCGAATCTAATTCGTTTTGG CTTTTGTGATCTTGATGTAAATCTATACTAACTTGGTTTGGGCA AGAGAAATTGGTCCTTGCTCAAGTCCATTCTAGGACGAAAATA AAAATATAACAGGGTATAGCAGATCTCTATTCGTATGTGGGTA ACGATAGCATGTTTCTATTGTTCTCTTATTCTTCATTGGTCACG ATAACCTGCTAATTATGCCACGATTGAGATGAAAAGTAACGAA CTAGTAAACCATAGTGAGAAGAACATTTCGCTACTATTGTTGA AACGTTTACACCAGGCACTTGAGTATGATGCACTATATTTCAA TTAATGTAATTTTTCGCTTTGATGAGAAACATTCTGATTCTGTG AGTTTAGAAACTATTGCTGATAATCCTTGATTTAAGATTTCAGT CTTGTTCATGTTCATTTGAAGTGTTGGTAATAAAATGCACTGAT GTGTCATGTGCAGATTGTGTGAAG |
| 19 | FAD2-2A coding sequence | ATGGGGGCTGGTGGCCGAACTGCTGTTCCTCCTGCCAACAGGA AGTCAGAGGCTGACCCTTTGAAGCGGGTACCATTTGAAAAACC TCAGTTTAGTCTCAGCCAGATTAAGAAGGCCATTCCACCTCAC TGTTTCCAGCGCTCTGTTCTCCGCTCATTCTCCTATGTTGTTTAT GACCTCACCATAGCCTTCGCCTCTATTCTTCCCACCCATTA CTTCCACCTCCTTCCCGGTCCTCTCTCTTTCGTGGCATGGCCAA TCTATTGGGCTGTCCAGGGTTGCATCCTTACTGGTGTTTGGGTC ATTGCCCATGAGTGTGGTCACCATGCATTCAGTGACTACCAGC TGCTTGATGATATTGTTGGCCTTATCCTCCACTCCGCTCTCCTA GTCCCGTACTTTTCATGGAAATACAGCCATCGCCGTCACCACT CCAACACAGGTTCTCTTGAGCGAGATGAAGTATTTGTGCCAAA GCAGAAGTCCAGTATCATGTGGTACTCTAAATACCTTAACAAT CCACCAGGCAGAGTCCTCACTCTTGCCGTCACCCTCACGCTTG GTTGGCCCTTGTACTTGGCTTTTAATGTTTCTGGAAGGCCTTAT GATAGATTTGCTTGCCACTATGACCCTTATGGTCCCATTTACTC TGACCGAGAACGACTTCAAATATATATATCAGATGCAGGAGTA CTTGCAGTATGCTATGGCCTTTTCTGTCTTGCCATGGCAAAAGG GCTTGCCTGGGTGGTGTGTGTTTATGGAGTTCCATTGCTTGTGG TCAATGGATTTTTGGTGTTGATTACATTTTTGCAGCACACTCAC CCTGCATTGCCACACTACACTTCCTCTGAGTGGGACTGGTTGA GAGGAGCTTTAGCAACAGTGGATAGAGATTATGGAATCCTGA ACAAGGTCTTCCATAATATTACAGACACTCATGTAGCTCATCA CTTGTTCTCCACAATGCCACATTATCATGCAATGGAGGCGACA AAGGCAATAAAGCCCATCTTGGGAGAGTATTATCGGTTTGATG GGACTCCATTTGTCAAGGCAATGTGGAGAGAGGCAAGAGAGT GTATTTATGTGGAGCCAGATCAAAGTACTCAGAGCAAAGGTGT ATTTTGGTACAACAATAAGTTGTGA |
| 20 | FAD2-2B polypeptide amino acid sequence | MGAGGRTAVPPANRKSEADPLKRVPFEKPQFSLSQIKKAIPPHCF QRSVLRSFSYVVYDLTIAFCLYYVATHYFHLLPGPLSFVAWPIYW AVQGCILTGVWVIAHECGHHAFSDYQLLDDIVGLILHSALLVPYF SWKYSHRRHHSNTGSLERDEVFVPKQKSSIMWYSKYLNNPPGRV LTLAVTLTLGWPLYLAFNVSGRPYDRFACHYDPYGPIYSDRERLQ IYISDAGVLAVCYGLFCLAMAKGLAWVVCVYGVPLLVVNGFLV LITFLQHTHPALPHYTSSEWDWLRGALATVDRDYGILNKVFHNIT DTHVAHHLFSTMPHYHAMEATKAIKPILGEYYRFDGTPFVKAM WREARECIYVEPDQSTQSKGVFWYNNKL |
| 21 | FAD2-2C promoter | ATTTGCCAAACAACGTGTCAAAATATACCCCGTGGGTCCCACC TCAATTGGACGGAAGGCGCACTAGTGCCACTGCTAATCGCTCG CTTTTAAATACCGCCTCTCTGCGTTCCCCTAATCTTTGCCCCCC TCTCTCTCACCCTCCTCTTCACACATTTTCTGTGCGCTCTAACA AACATTCTCGTTCACACTTTCAGGTACTTTTCTCTCCTTATCTCT TTATCTTTATTCTTTTCCTACTTTATTGCTTAAACCAATGCTATCT ATGCTTCAATCTCGCCTTCTTATTTTCCACTTCCCTTTTCTCGCT TGATCTAACCGTTTTCGCCCTCCGCGCTTCGATTGACTGAGTAC ATCTACGATTCTCTGTTCTTTCATTTCATAGATTTCGTCTGATTT |

TABLE 1-continued

Wild Type "Forrest" Sequences for FAD2-2 Family Members

| SEQ ID NO: | Sequence Description | Sequence |
|---|---|---|
| | | TGGCTAACTTGGTTTCTGTTGCGGCCGATTCTTACATATACTGA |
| | | TTGTTTAGCATAAATGAACTTGCTTGTTTAGCACTATCTGCATA |
| | | TTTTCGTCACGCATCTCTTTCGGATCTAAGGATGAATCTCCTAT |
| | | TTCCTCCGTATTATTTCTCGTATCTCTTGTTCTGTGCTAATGCTC |
| | | CAGAAAATGGCAGCATTGTCTTCTTCTTTGCTGTTATAAGTGTT |
| | | TGTGTTGTGAATCTGGAAGCGATTTTGCGTGAGGTAACTTGCG |
| | | ACTTCAACTATTATCTTTCAGATCTCGTTAATTTATTAGCTGCT |
| | | ATTAATTTGTGTGTGCAGTGTCAAACTGAAGCACACGACTGCT |
| | | TAGAAGTTAGAATTTGACTGACTGTTCCTCTTTGATTTTTTTCT |
| | | TTCTTTTCTTTGCTTACTCGGCCTATTTAATGATCTTTATAAATA |
| | | GATTAGTGGACCACTTGGTTAGTTGGTGAGTTATGAATATTCG |
| | | AATTTTCTACCACAAGTTGGGTTAAAAAAATCTCTGCAACTAC |
| | | ACGAGGATTTTTTATTTTATTTAGAGGAAACTATTCTGTCATCC |
| | | TTTTTCCGATTACACTTTTCTATCAGTTGTTTTGAAATATACAC |
| | | CTTAGGAATATAATATTACCCCTTTCGGTCTTAATATAAATATA |
| | | TTTTAATTATTTATATTTTATTTAATGAAATTATTTTTAAAATAC |
| | | TTTCATTTAATAGAATTTTTAATAAAGTTAAAGACTTTTATTGT |
| | | GTAGAGTTTAACGAAGTTAATTAGTTTTCTTAGTAAATGTAAA |
| | | ATATGCCTTTTTTGTTGTTTATAATGGAGATTGGAAAAAATATA |
| | | CTTTAATTTTTTTCAAGTGATGAATAATTATGGATGTTTTGTCA |
| | | ATATTTTTGTCTTGCTATACAACTTTCAGTCTTGCCATTAAATA |
| | | ATTTTGAATGTGTTATTGATATCTCTGAACAATATTTAGAGAAC |
| | | GAACAATAAAATTTTATATATTTTTATTATAATTTCTTTTTATT |
| | | ACCTTTTTATTATCAATTTTGAAATTTGGTTTAATATCTGTGTTT |
| | | CATTTTTGAGGTCTCAAATTTGATATAAGGAGGTTCAAAATGC |
| | | GTTGCTAGCCATTTTAAAGATTAGCAGGAGAGGAAATGTTTCT |
| | | GGACTTAAATTTAAAATATGCTTATTTGTTTTTCAAGAGAGAG |
| | | AGATCAATATTTATATAATACACTTGAATTAATATACACCATT |
| | | GTTGCAAAAAAAAAAAATATTAGTTGATTGTGTGACAATATT |
| | | TTATATTAAATATAATTAGTTAATTTAGTTCAAGTTGAGTTACA |
| | | TTTTTACATACCATTCTTAGCCGCCACTTTTTTATATTTATTTGT |
| | | AGGAATAACTTTTCATCTGTATCAATTTTCCCCGTCTAATAATA |
| | | AGGGTTTGACTTTTTCTTATAATAGAGTTTTTTTTTTTTGCTTT |
| | | AAGTTATTGTAAAATAATTATTTTATTTTTTTTGCCTTTGTAAA |
| | | TTATGTATATTTAATGTTTTAATAGGAAAAAAATGTTATCAAA |
| | | AGCACTAAAAGACTAAAATTAAACAACCATAATTTGCAAAGA |
| | | TGAAAATAAAAAAATAATTTTGTAAAGATAAAAAATGAAATA |
| | | AAATAGTTAAATTATAGGAATTTAAAAGCTATTTAAATCAACA |
| | | AAAGTTAAAGTTTCTGTAAAAAAAAAGTTCAATTTTTTTTTAT |
| | | TATTGAAAAAGTTAAAGCTAATGAGCGTTCGATTTGGGTTAGT |
| | | ATGTAGTATTTATTATTTTCAAGATTTTGGATTTTATTGTCGAT |
| | | GTTTCTGATTTGAATATAATTATTTTCCATTCAACTTGTGATTTT |
| | | ATAAGAAAAAAAAAGGTACAGAAAAAATCAAGCGCTTTTTTT |
| | | ATTTCAATTAGTGGAGGTTTCACTGAAATGGGTAAAGAATCTA |
| | | TTTTGCAATCACAATTATTACCGGTATTCAACTGCAACAAGGA |
| | | ACAAAATTCCTTTCGTAAATATACGGAGAGGAATCTATTTTGA |
| | | CTTGTTGAATTTATGGTAAAGTAGAATTTAGAATTTAATTATG |
| | | AGTTGAAGTAATTTTGAATAATTTATATGTTAAATATAAAATTT |
| | | TGTACTAAGTTTTATTCATAACTTTGATTCTATAATACAAACAT |
| | | ACATAAGTTCAAAAATAATTTTAATTAAAATTAATTTTATCAA |
| | | TTTTTATTCAAACACGAGTCTAATTTGCTTGATGAATTAAGAA |
| | | AATAAGGAAGAAAATATTAAAAACTAGGAGAGAAGTTAAAGA |
| | | GAATTTCATCTTTATTATTCTCAGTTGTTTCAAAAATAATGAAA |
| | | GGATAGCTATATAATACTGTAACTGAGCCAAGAACATATTTGC |
| | | CGTCCGAGTAACCTTTTCTTTTCTTGTTCCGTTTTCTCCGCCGAT |
| | | GAAGAGAGGGAAGGGAATGTATCTTTGTATTTATGTTTTCAAA |
| | | GAGTTCGTGCATAAAATTGGTTTAATCAAATTTTTCATAAGATT |
| | | ATTATTTATGATTTTTAAAATAAATTAGTAACTATATTCCGT |
| | | AAGTCGTACACAGTTATATGTAGTAAGTAAATTATATTTTAAT |
| | | AATTATTATCTTAAAATTTTCTTAAGAACTTGGTTAAAATATTT |
| | | TTGTTTGAAAAAGTTTATGATAACTTTTTTTTGTTGAAAAAAAG |
| | | TTTACGATTATCTAACTCGTACTTAGATTATTTCTAATTGGGAT |
| | | TTATTGAAGGGTTTTTAAGTAAAGAAATTGTTTCTTATGGTTT |
| | | CTTTTTTATTGGACAAATTTACGTAGCAAAGAGTGTTTCTTAAA |
| | | AACAAGACATGTATCCTTTGAAAAAAAAACTATTTCTTTGAAA |
| | | TAAAAAATAATATTTATCTGGCACATAATAATGTTAAAATTAA |
| | | ATCATAATTAGGTAAAAATAAAATAAATATAAAGTATGAGTT |
| | | TGTTAAGTTTTTTATAATTTTTTATTATTAAAGTAAAATTATGT |
| | | ATGATTTTTTATAATGATATGATATTTTAGGGATCACAAAAA |
| | | ATAATGTGGTGAATACAAAAGTAACTCAAAAAATTCATTTAGT |
| | | AAATTTTCATTGGAGATGCTATTATTATGCTTTCTGATTGCTTT |
| | | GTCCAAAAAATAAAGAATGTTTTTTTATTTGAAATTGAAAAT |
| | | TTCTGGGTCATGTTAAGATCTTGTAGACGGTAACGTCGGCCTA |
| | | AAGTTGTGTGAGGGGTGTTGCATGCACCGATCATTAATTACTC |

TABLE 1-continued

Wild Type "Forrest" Sequences for FAD2-2 Family Members

| SEQ ID NO: | Sequence Description | Sequence |
|---|---|---|
| | | GATATGGAAAACGACTGAAATAATTTAATTTGATGTTGCTAAT ATTGGCCATCCCTCTCATCATTATTGTTTTTTTATTTGTAACATG ACATATTCTTGTGGGTCCGCTACGGATTGGGTGTTTGTTGCCAA AAAATACAAAATATCTGTGGAACAAGGATAAACAGTCTTGTTT GTTTAATTGATTGATTGATGAGTTTGCAAGCTATATTTTTAATT TATTTTAATTAAACTTTTGTGTTTTAGTTCTACAATTTTATTCAT CTTGATTTTTTTTTTACTTGGCAAAATCATGATTTTTTAATTTTT ACTTATGTTGAAAACAAATTTATTGCTAAAAAAACATTTATTC TTTTTTTAGAGGAAAAACAAATTTGTGATATGTAGTGAATCAA ATGAAAATTTTAAACATAATATAGAATACTCTACAAATCAATT TTGAGTTTCTTTATCATTTTATTTATTTATTGACATACTTCTACT TTCTGCAAAGACCCTGACTCGTGGGAGATATAGGGAAGGTTAT GGAAGTTAGTGTATTGTCATATCTAGCTATCTTTGCTAATTGAA AAAGCCTTCCCTTTGTTTACAGATCTGGATAAGGTTGCATGTTT ATTCTTTTCAACTGTGAATGGTTCTTTGCATCTTTTTTAGTATAT GAGATTAATGTTTTAATTAGGAAGAAGCTTTTAGAACATCACC CGAATCCAATTCGTTTGGTTTCTGTGATCTTGATGTAAATCTA TACTAATTTGGTTTGGGCAGGAGAAAATGTTCTTTGCTCAAGT CCTCTAGGACGAAAATATAAATATAACAGGGTATATCAGATCT CTATTCTTCTGTGGGTAATGATAGCATGTTTCTGTTGTTTTCTT ATTCTTCATTGGTCATGATAACCTGCTAATTCTATTTGCCACGA TTGAGATGAAAAGGTAATGAACTAGTAAACAATAATGAGAAG AATATGTCGCTACTATTGTTGAAACGGTTACGCCAGGCACTTG AGTATGATGCACTATTTTAATTAATGCATTTTTTTTTGCTTTGA TGAGAACGCACATTGTTCATTCTGATTCGGTGAGTTTAGAAAC TATTGCTGATAATCCTTGATTTAAGATTTTAGTCTTGTTCATGT TCATTAAAAGTGTTGTAAAAAAATGCACTGATATGTCATGTGC AGATTGTGTGAAG |
| 22 | FAD2-2C coding sequence | ATGGGGGCGGGTGGCCGAACTGATGTTCCTCCTGCCAACAGGA AGTCAGAGGTTGACCCTTTGAAGCGGGTGCCATTTGAAAAACC TCCATTTAGTCTCAGCCAAATCAAGAAGGTCATTCCACCTCAC TGTTTCCAGCGTTCTGTTTTCCGCTCATTCTCCTATGTTGTTTAC GACCTCACCATAGCCTTCTGCCTCTATTATGTTGCCACCCATTA CTTCCACCTCCTTCCCAGCCCTCTCTCTTTCTTGGCATGGCCAA TCTACTGGGCTGTCCAAGGTTGCATCCTTACTGGAGTTTGGGTC ATTGCCCATGAGTGTGGCCACCATGCATTCAGTGACTACCAGT TGCTTGATGATATTGTTGGCCTTGTCCTCCACTCCGGTCTCCTA GTCCCATACTTTTCATGGAAATACAGCCATCGCCGTCACCACT CCAACACTGGTTCTCTTGAGCGGGATGAAGTATTTGTGCCAAA GCAGAAGTCCTGTATCAAGTGGTACTCTAAATACCTTAACAAT CCTCCAGGCAGAGTCCTCACTCTTGCTGTCACCCTCACACTTGG TTGGCCCTTGTACTTGGCTTTAAATGTTTCTGGAAGGCCTTATG ATAGATTTGCTTGCCACTATGACCCATATGGTCCCATTTACTCT GATCGTGAACGACTTCAAATATATATATCAGATGCAGGAGTAC TTGCAGTATGCTATGGCCTTTTCCGTCTTGCCATGGCAAAAGG ACTTGCCTGGTGGTGTGTGTTTATGGAGTTCCATTGCTAGTGG TCAATGGATTTTTGGTGTTGATTACATTCTTGCAGCATACTCAC CCTGCATTGCCACATTACACTTCCTCTGAGTGGGACTGGTTGA GAGGAGCTTTAGCAACAGTGGATAGAGATTATGGAATCCTGA ACAAGGTCTTCCATAATATTACAGACACTCATGTAGCACATCA CTTGTTCTCCACAATGCCACATTATCATGCAATGGAGGCTACA AAGGCAATAAAACCCATTTTGGGAGAGTATTATCGGTTTGATG AGACTCCATTTGTCAAGGCAATGTGGAGAGAGGCAAGAGAGT GTATTTATGTGGAGCCAGATCAAAGTACCGAGAGCAAAGGTG TATTTTGGTACAACAATAAGTTGTGA |
| 23 | FAD2-2C polypeptide amino acid sequence | MGAGGRTDVPPANRKSEVDPLKRVPFEKPPFSLSQIKKVIPPHCFQ RSVFRSFSYVVYDLTIAFCLYYVATHYFHLLPSPLSFLAWPIYWA VQGCILTGVWVIAHECGHHAFSDYQLLDDIVGLVLHSGLLVPYFS WKYSHRRHHSNTGSLERDEVFVPKQKSCIKWYSKYLNNPPGRVL TLAVTLTLGWPLYLALNVSGRPYDRFACHYDPYGPIYSDRERLQI YISDAGVLAVCYGLFRLAMAKGLAWVVCVYGVPLLVVNGFLVL ITFLQHTHPALPHYTSSEWDWLRGALATVDRDYGILNKVFHNITD THVAHHLFSTMPHYHAMEATKAIKPILGEYYRFDETPFVKAMWR EARECIYVEPDQSTESKGVFWYNNKL |
| 24 | FAD2-2D promoter | AAAGGCTGCGAGAAAATAACAGGAACGAACGATGATATTATCG GCAAAGAAAGAGAGAAAAATGTCCTCATCAGCAAAAATAATA ATAATAATAATAAATAAAAGAATATGATGGGTAACCCTTC ACTCGAGGGAAACCTTCATTTCGTGGAGAAGTAATATAGCA TAAATACTCTTTATCTTCCCTCATCTCCTTACAAATTCTTCGTCT GCATCTTCTCTCCTTCAGATACAGAGGGAGAAAGATACAAAAC CTTTTCACTCGTCCTTCTTCTTCAGGTTTTTACCCCTAACTTATG |

TABLE 1-continued

Wild Type "Forrest" Sequences for FAD2-2 Family Members

SEQ
ID  Sequence
NO: Description Sequence

```
CTTCATTTCTTTTCTTTTTTCTTTTTATTTTTATTTGCCTTCTATGT
TTCTTCTTTTATATATGTTTTTGTTTGTTGTGATTAATGCTTATAT
ATTGCCAATAGATATAATCACGAGGTTTAATTTCCAGCTGAGTC
TTATTTTCACGATTGCATCTTTGCTAGATCTAAATCATCTAATAA
TTGCCCCTTTTTCTGTCGTTCATGTACCTTCTAGATGTTTAACGT
TGATTTACCTTCTTGGTGCTTGTTTTAAAGTTTATTTGGTTCAAT
GTGGTTTTACTCTGAAATCGAATTGTGACTACAACTATAGTTAC
GTGCATCAACCATATTTTATTCAAAGACGGAGTGCATCATACAT
GTTCTTTTTGTTAACGTTTAGAACTTTTCTTGGATCCAAGGATGA
ACATCTTTTTCTGCTTTTCATGATTAATTTTTCGTATTTGTTGTTA
TGTAATGGGGATCTCGTGACAGTGTTACGCTTTCTCGTGAGTTC
AATTTCATCTTATAGCTACCAATGAATACGATCATCGTATGACG
TCGTAGGGTTTTTAAGCCGATAAAAAAAACGTTAGGGTTTTTAA
TTTTAAAATATTATTAATATTATTTTTTGTTAAATTAATATATAT
TTTATCTTTTATTCCAATTTTTCCTATATTTGACTTAATATTTAAT
TTTTTATACTGCATAATTTTCTAAAGAAACAAGAGTTCAAGGTT
AACAAATTCTTTCTCTAATTGATAAAAGTCTGTTCATAATAATA
AATTTACCTTTGCTTTATTTCTTGTGCTTTTCAATTTCTTAGTGG
AAGATCTTTTTTTTTTAATGGATAAAATGATCATTTGTGGTTAA
TTATTTATTTGATATGGGTGGCTCTTATTGCACGGCTGCTATGCA
AGGATTCATTTCAACAGCAAAAAGAGCAATTATAAAATTAAGA
GAAGAGTTAACAGTTCTTTAATGTAGTAATTTTATTAATATATTT
TTTAGTTAAAATTTATGTTGTGAGTTTTATTAATTTGAAGATGAA
ATGGGGAAGGAAACTCACATATTTCATGAAACTCACGTAATTT
GCATAAGAAAAGTGTATTTGAATTTTTTAAAACATGTTGCTAAC
TTTTCTCATTAAAAAATATGATTTCCAAGCTGCCCACACCATGC
ATAATTTCCATGTGATTATACTTTGTCAAATTATTTTAATGCGCA
TTTAATTATCTATGTTGTAAACTTCGTTGAAATGGACTTGCAAG
TAATTCCCTAGATAGTAGTTTTAATTTTCCACGGCTCCATTTTGT
TCACAATTGAGTGTAGACTGTAGTTGTATTCTATTGTTTTGTTTG
TTAGGTTTGCACTGTGCAAGCTACTTAACTATTTGTTTATGTTGA
CTGATTACCATCTTCCGCATACATTTGACACGTTCATAGAATAG
ACATATTCTTGTAGACAAAAATTAATTATCTTTTCAAACTCCAC
CAAATCTTATATTGGAACGGAATGTGAAAGGATTGTAAAACGT
GCGTCGTAAAAATTAGAATCCGAAAAGTATGTGTTAGCATACC
AAACTCTTATATTGATTCTTTAAAAGAAAATAAAAGAGTGGGTC
CAAAATTGCGAATACGTGTTCTTTTATTAAAATATGATTTTAAG
AATGACGCATCTTTATTGTCAACTACAGTGTATGATAACGCTTT
TTTGCCTATATATAGGCCATTTTGAATTTTATACGATTCTACAAT
AGAAAAGTTTTTAATTTACATACGCTTTAGTGCTTGTGTAACTG
AACAAACTAGCCTTATACTATACATGCGCTGATATTTACGTAAT
TACTATGGTAATTGTTGGAGATGGAGGAATATTAATCTTTGACT
TATTGGAGTTGGCCTACTGGTGGAGTTAGAAGTACGTAGATGTA
TGAGGACTCAACTCAGCAAAAACAAATGTATGAGGACTTGATA
TAATTATTGCTGTCGTTACAAAAAAAAATTAAGAGAAATGTTA
AGAATACAAATACAATTTCTAACACATTATTTTATGAGTTTCAC
ATGGTATTCAAATGACTACATATGTCAATTTTAACTCCAGAGAT
TATTAACTAAGATAACTAATTTTTCTTATGTTTGACAACACCAC
ATAAGGAACCACATCATATAGTACTCATATTAGTACTATAAAGC
ACTCATGAATTCATTTTCTTTTTTATCATGAATATCATACACTTA
AAGATATGCAAGATTTCAATTTTCATCTTCGACAAGCCAACATT
AGATTTGAAGTTAGCGTCGATTTAGATGCTAACTACAACAATAA
AAAAATTAAGAAAAACATGTTATTAGCTTACATGACAATGATG
TAATAATGATAATGTGATATTCTATCTGTCACGTCATCGTTTAA
TAGATAAATATTAACGATAGGTGCCAAAGCAAAAAAAACTGAA
AACATGAGATAGAAAAATCAAATTTTTTATAAGTAACAATCTA
AAAAAGAGATATATCTTAGGTAAGAAAAACATATTTAAGTCTT
TTTAATATATTTTAACTGATTAAAGAGTGAGTATTTAAAGTAGT
ACATTAAAGATTCCGCTCCTGCCTAATTAGACATAACCTATTTC
ATGTTAGTTTTTGAAGTTACTGCTCATTCTATAAGGTCACCTATT
ATTACTTGCGTGCATGGAATGCTAGAGACATTTTTTTTATATTCT
CTAACACTCTTGGATTGACTACTCTTGGATTGACTAAAAATTTA
TTGAAAATTGTCAATTTTGGTGGGTCTTAATTCTAAATTAAGAG
AGAATCATTATATAAAAAGTGAAATTTATTAAAATTTATTATTT
TAATAAATTTTATTCAATCATAGACATAATATAATATTAGAAAG
AGTTTCCCTAGTACTTCTCCATTACCTATGTTTAATCAGATAAAT
TATATTTGAGATGTTCATGAGGATGTTAAAAAATCATATTCACT
AGCTGTGATAGTGATGTGGTCAAAATAATTAATATAAATAGAA
GATAAGATCTTATTTGATGAGTTAGTTTTGCAATTAAGTCACAT
CATAATCCAAATTCCAATACTAATCAACAAACTTTTCTATTCAT
GTTTTAGGTTGCGCGATAAA
```

TABLE 1-continued

Wild Type "Forrest" Sequences for FAD2-2 Family Members

| SEQ ID NO: | Sequence Description | Sequence |
|---|---|---|
| 25 | FAD2-2D coding sequence | ATGGGAGGTGGTGGTCGAAGCTCAGCTACTCTCAAGCATCAAA ACTCAATTGAAAACCATTCAAAGAAGAAGCGTGTCCCACATGC AAAGCCACCCTTCACTCTAAGCCAACTGAAGAAGGCAATTTCA CCACATTGCTTCCACCGTTCAACATTCCGTTCATTCTCCTACGT CCTCTATGACCTAACCATAGCCTCATGCCTCTTCTATGCCGCAG TAAATTACATCCCTACCCTTCCCCATGAAAACCTCTCCCTCCTA GCATGGCCTCTCTATTGGTTCATCCAAGGTTCCATCCTAACCGG GGTTTGGGTCATCGCACACGAATGCGGCCACCACGCCTTTAGC GATCACCAATGGCTCGATGACCTTGTTGGCCTAATCCTCCACT CACTTCTCCTAGTGCCCTATTTTTCATGGAAATATAGCCACCGC CGCCACCACTCGAACACAGGATCACTCGAACGTGATGAAGTGT TTGTGCCAAAAACAAAGTCTAGTATGGGTTGGTATTCTAAATA CCTTAACAACTCGCCAGGGAGGGTTCTCACACTTGCTATAACC CTAACCCTAGGTTGGCCTCTTTATTTAGCTTTCAATGTTTCGGG TAGGTCTTATGAGAGATTTGCATGTCACTATGACCCTTATGGC CCCATTTACTCAAACCGTGAAAGGCTTCAGATTTATGTATCCG ATGCTGGGATTCTTGCGGTGTGTTTTGGTCTCTACAAGGCTGTC TTGGCAAAAGGGCTTGTTTGGGTTGTTTGTGTTTATGGGGTGCC TTTGTTGGTGGTTAATGGGTTCTTGGTGTTGATCACTTTCTTGC AACACACTCACCCTGCGGTTCCTCACTATGATTCCTCCGAGTG GGATTGGTTGAGAGGTGCTTTGGCCACTGTGGATAGAGATTAT GGGATTTTGAATAAGGTTTTGCATAACATCACTGACACACACG TGGCACATCACTTGTTTTCCACAATGCCGCATTATCATGCAATG GAGGCTACTAAGGCTATAAAACCAATTTTGGGAGAGTATTATC ACTTTGATGAGACTCCTATTTATAAGGCAATGTGGAGAGAGGC AAAGGAGTGCATGTATGTTGAGCCTGATAAAGGGTCTAATGG GAAAGGTGTTTATTGGTACAATAATAAGTTGTAAACATTAGAG CTATTGAGTATTGGTTGAGACTCGAGAGTTTAGAGTTTAGGTT TGTTATGTACGAATCTCTAATGTTCCTTATGGGTCTTATAAAAT AATTTCATAATCAGTGGTAGAAAAGGAGAATGTAATGAGTGT ATGCCTATGTTGTTATGCATATGGTGGGTTGAAATCAGTTTATG GCTTTCACTTAATGGTTGGGAAGCT |
| 26 | FAD2-2D polypeptide amino acid sequence | MGGGGRSSATLKHQNSIENHSKKKRVPHAKPPFTLSQLKKAISPH CFHRSTFRSFSYVLYDLTIASCLFYAAVNYIPTLPHENLSLLAWPL YWFIQGSILTGVWVIAHECGHHAFSDHQWLDDLVGLILHSLLLVP YFSWKYSHRRHHSNTGSLERDEVFVPKTKSSMGWYSKYLNNSPG RVLTLAITLTLGWPLYLAFNVSGRSYERFACHYDPYGPIYSNRER LQIYVSDAGILAVCFGLYKAVLAKGLVWVCVYGVPLLVVNGFL VLITFLQHTHPAVPHYDSSEWDWLRGALATVDRDYGILNKVLHN ITDTHVAHHLFSTMPHYHAMEATKAIKPILGEYYHFDETPIYKAM WREAKECMYVEPDKGSNGKGVYWYNNKL |
| 27 | FAD2-2E promoter | CCTTAAACCCAATGGTTGATAGAGATTTTTCTCCAACATCTCTG TTGATAACTAATTAGCTTGTGATCTTTCTTATCTACTAATACAA ACTACACTAATGGTTCTCACGCATCCTCAACTCATGGCCAAAT AAACCCTCGTAGTCACAATTCCTCTACTTCTACTGACCCTCCAA ACAACAACACTCAATGGGGTAATGTCTCTCACTCAGTCCCTGC ATGCCAGTATTGTGGTCGTTGTGACCACACTGCCAAAACATGT TACAAGCTGCATGGTATTGGGACCCCTCTGATCATCATCTCTA CTAAGCAAATATGTCACAACATGATAACAGTTCTGATCCCAAT TGGTTGCTTGATTTGTGATCTTGGAAATTTATCCGTCTCTTTTTT CAACACTCTGGCTCCACCTCTATACTTTGGCATGGTATATTTTT GGTAGCACTAGAAATCTCACTTCTCCAACTTGCAAATCAGCCT TAAATAATACATACTGTTGGTGTATCATTTTTTAAGATTCCCTAT CATGGAATTGGTGGATCGTACGTCTACTTGATTTTAGGTCTCTC AATTCCTAGTCAAAATTAGTCTCAATCATTATGCTTTAAAAAT GATGATTTTGACACTTGGGAGATAACAATATTTCTTAAAGTTTT GATTCTCAAGTTTGTATATATGAAATAGTGTGTTGGGAGAAGT AAACTCTTAAAATAAATTTTTATATTTTAGAGATGATTCTCTCA TTCTTATGAAGGAGATATACTAGAAAAAAATGATTTTTATTTTT TTATTTTTTATTATGAAACTTAAGAATTAAGATACCAGGATGA GGGACAAAAGTCATTAATTATTAAAAAAAAAATACAAGAATC AAGATTATTATTTTTAAAATATAAAAAAAACTAATTTTGATAT ATAAAGAAATCCAGGGGATATAATACACATTCTATCCAAATAT TTTGTTAAACCCCAGGGGCACAATGTTTCGTCTTTCCTCAACAG TTATAAATTGCTAATGATATTATTTGTCTTGAATTGGTTCCTGT GGCTAGCATATCTCTGCAACTTGTGCAACCATTTGGTAATTCA ATTAAGAATATATAATATACTTTAAATTTACTAGGATGCATAA AAAACCCTGTGACTTGTCTGACCAAGACTTGCCAAATTTTTTA TCATGCATTACAAAAACCAGCCATTTGTTTTTATTTTTTGGATT TCTATTCTTTCCAAATGAAGGCCTAACAGATAAATTGCATGTC TAATTTCCCCTTGTTATTAGAGAAATAAGAAATTATAAGCTTTT |

TABLE 1-continued

Wild Type "Forrest" Sequences for FAD2-2 Family Members

| SEQ ID NO: | Sequence Description | Sequence |
|---|---|---|
| | | GCTTTGACTTTTGAACATATTTTACACTCTTTGCAGGTTGCTTT TTATCTTGGAAGACCAGAGGAGTTCAAAATAACAGTGTCGCGG TAAGTAATTGCTCGTACATTTCCTTGGTAATTAGGTCTCTTATT GCGTATTGTTGCCATCATTTTTGAGGCCTTGTCTGGCTTGCATC ACAATTGAAAGAAATTAGTTTGATGGTTAAAATGGTATACCTT TTGTCTTCATTATTACTCGAATTACATTTAGAAAGACCTATTAA TAATTACTTATTTGAGTTTATCATATCACATAAATACTTATTTA AACGTCTGGGAGAGTATTGTACGAAAGTAACATAAGAATTGA CTTAAAAGTTAAATACTTTTGGTTGAATATGTTTGTCATTTGAT ATAGAAGAGAGAAAGAAAATATCTGTCAATTAAACAATTTATT AGTAATATTTTTTTGTAGCATTCCATTTTTATTTTTTTTTTGGA ATTGTTTGCACAATGTTTCGTCTTTCCCCAACAGTTATAAATTG CTAATGATATTATTTGTCTTGAATTGGTTTGGAATGTTTAAATG TGCACCCTAAGTTTGAAATGTGATTCATTTGCGACCTCACCAT AGCCTTCTACCTCTATTATGTTGCCACCCATTACTTCCACCTCC TTCCCAGCCCTCTCTCTTTCTTGGCATGGCAATCTACTAG |
| 28 | FAD2-2E coding sequence | GCTGTCCAAGGTTGCATCCTTACTGGAGTTTGGGTCATTGCCC ATGAGTGTGGCCACCATGCATTCAGTGACTACCAGTTGCTTGA TGATATTTTTGGCCTTGTCCTCCACTCCGGTCTCCTAGTCCCAT ACTTTTCATGGAAATACAGCCATCGCCGTCACCACTCCAACAC TGGTTCTCTTGAGCGAGATGAAGTATTTGTGCCAAAGCAGAAG TCCTGTATCAAGTGGTACTCTAAATACCTTAACAATCCTCCAG GCAGAGTCCTCACTCTTGCTGTCACCCTCACACTTGGTTGGCCC TTGTACTTGGCTTTAAATGTTTCTGGAAGGCCTTATGATAGATT TGCTTACCACTATGACCCATATGGTCCCATTTACTCTGATCGTG AACGACTTCAAATATATATATCAGATGCAGGAGTACTTGCAGT ATGCTATGGCCTTTTCCGTCTTGCCATGGCAAAAGGACTTGCCT GGGTGGTGTGTGTTTATGGAGTTCCATTGCTAGTGGTCAATGG GTTTTCGGTGTTGATTACATTCTTGCAGCATACTCAACCTGCAT TGCCACATTACACTTCCTCTGAGTGGGACTGGTTGAGAGGAGC TTTAGCAACAGTGGATAGAGATTATGGAATCCTGAACAAGGTC TTCCACAATATTACAGACACTCATGTAGCACATCACTTGTTCTC CACAATGCCACATTATCATGCAATGGAGGCTACAAAGGCAAT AAAACCCATTTTGGGAGAGTATTATCGGTTTGATGAGACTCCA TTTGTCAAGGCAATGTGGAGAGAGGCAAGAGAGTGTATTTATG TGGAGCCAGATCAAAGTACCGAGAGCAAAGGTGTATTTTGGT ACAACAATAAGTTGTGA |
| 29 | FAD2-2E polypeptide amino acid sequence | AVQGCILTGVWVIAHECGHHAFSDYQLLDDIFGLVLHSGLLVPYF SWKYSHRRHHSNTGSLERDEVFVPKQKSCIKWYSKYLNNPPGRV LTLAVTLTLGWPLYLALNVSGRPYDRFAYHYDPYGPIYSDRERL QIYISDAGVLAVCYGLFRLAMAKGLAWVVCVYGVPLLVVNGFS VLITFLQHTQPALPHYTSSEWDWLRGALATVDRDYGILNKVFHNI TDTHVAHHLFSTMPHYHAMEATKAIKPILGEYYRFDETPFVKAM WREARECIYVEPDQSTESKGVFWYNNKL |

Example 1. Development of an EMS Mutagenized Forrest Population

The soybean cv. "Forrest" seed was used to develop an EMS mutagenized population (at 0.6% EMS), and planted to harvest 4032 M2 families and then advanced to the M3 generation at the Horticulture Research Center at Southern Illinois University Carbondale, IL, USA.

Example 2. FAD2 Sequences and Phylogenetic Analysis

GmFAD2 sequences used in the phylogenetic analyses were retrieved from different databases including UniProt, NCBI, Soybase (W82.a2.v1), and Phytozome (v12.1). Sequences were identified by querying sequences from the seven members belonging to the two GmFAD2 subfamilies against sequences from these databases using tblastn default parameters. Sequences from monocots, eudictos, and basal angiosperm with 90% identity/similarity and above were selected, in addition to other GmFAD2 homologs from plant primitive species including, algae, moss, and a lycophyte. The retrieved GmFAD2 sequences belong to sets of plants (48 in total) with fully sequenced genomes representing key positions in the angiosperm phylogenetic tree. Sequences were carefully inspected and corrected for annotation errors before use. Multiple sequence alignments of the retrieved GmFAD2s were performed using the MEGA4 software package and the ClustalW sequence alignment tools. An unrooted phylogenetic tree was calculated with the neighbor-joining method. Next, tree topology robustness was tested through bootstrap analysis of 1,000 replicates.

Example 3. Chromosomal Distribution and Synteny Analysis

The locations of the two fatty acid desaturase GmFAD2-1 members and the five GmFAD2-2 members in soybean and their corresponding chromosomes were obtained from the soybean genome annotation a2.v1 assembly (Williams 82 reference genome) available on the soybean database (SoyBase.org). Non-synonymous (Ka) versus synonymous substitution (Ks) rates were calculated based on their values retrieved from the Plant Genome Duplication Database (PGDD). Based on the Ks values and the rate of $6.1 \times 10^{-9}$ substitutions/site/year, the divergence time (T) was estimated using the following formula: $Ks/(2 \times 6.1 \times 10^{-9}) \times 10^{-6}$ Mya.

Example 4. Library Preparation, Probe Design and TILLING-by-SEQUENCING+

Genomic DNA samples from 42 "96-well plates" were pooled using a bi-dimensional scheme. Forty-four probes were constructed to amplify the whole gene region of GmFAD2-1A with up to 99.6% coverage, 77 probes were constructed to amplify the whole gene region of GmFAD2-1B with up to 98.4% coverage, 18 probes were constructed to amplify the whole gene region of GmFAD2-2A with up to 99.7% coverage, 58 probes were constructed to amplify the whole gene region of GmFAD2-2B with up to 98.8% coverage, 47 probes were constructed to amplify the whole gene region of GmFAD2-2C with up to 99.8% coverage, 37 probes were constructed to amplify the whole gene region of GmFAD2-2D with up to 98.9% coverage, and the GmFAD2-2E gene was covered by 20 probes with up to 99.8% coverage (FIG. 1). Probe synthesis, DNA library preparation, capture enrichment (using magnetic beads), and next generation sequencing (Illumina HiSeqX 2×150 bp) were carried out by Rapid Genomics LLC. (Gainesville, Florida).

Example 5. RNA-Seq Library Preparation and Analysis

Four plant soybean tissues were used for RNA-seq including seed, leaf, root, flower and pods. Total RNA of each sample was extracted from 100 mg of frozen grounded samples using RNeasy QIAGEN KIT (Cat. No./ID: 74004). Total RNA was treated with DNase I (Invitrogen, Carlsbad, CA, USA). RNA-seq libraries preparation and sequencing were performed at Novogene INC. using Illumina NovaSeq 6000. The four libraries were multiplexed and sequenced in two different lanes generating 20 million raw pair end reads per sample (150 bp). Quality assessment of sequenced reads was performed using fastqc, version 0.11.9. After removing the low-quality reads and adapters with trimmomatic, version V0.39, the remaining high-quality reads were mapped to the soybean reference genome Wm82.a2.v1 using STAR, version v2.7.9. Uniquely mapped reads were counted using Python package HTseq v0.13.5. Read count normalization and differential gene expression analysis were conducted using the Deseq2 package v1.30.1 integrated in the Omics-Box platform from BioBam (Valencia, Spain).

Example 6. Variant Calling for Mutation Detection

The FASTQ raw reads were subjected to quality control using FastQC v0.11.9, trimming, and filtering of low-quality reads was performed using Trimmomatic V0.39. BWA v0.7.17 was used to map clean reads to the Williams 82 reference genome. SAM tools v1.10 were used to filter and sort the bam files to serve as an input for variant calling using Freebayes and CRISP v1.18.0 The VCF files were filtered by VCF tools v0.1.16 and visualized in IGV v 2.9.2.

Example 7. Mutation Density Evaluation

The mutation density is estimated using the formula as the total number of mutations divided by the total number of base pairs (amplicon size×individuals screened).

Example 8. Analysis of Seed Fatty Acids

For EMS mutant lines, a five-seed sample taken from each mutant line was placed in an envelope and manually crushed with a hammer. A fatty acid extraction procedure was then carried out. Five major fatty acid contents were measured from selected according to the two-step methylation procedure.

Example 9. Confirmation of the Mutants by SANGER Sequencing

The specific primers (FIG. 2, SEQ ID NOs: 1-14) were designed to amplify the 7 fatty acid desaturases using the extracted DNAs as the templates with 38 cycles of PCR amplification at 94° C. for 30 s, 51° C. for 30 s, and 72° C. for 1 min. The PCR products were purified. The purified PCR fragments were sequenced by GENEWIZ, LLC.

Example 10. Homology Modeling of GmFAD2-2 Proteins and Mutational Analysis

Homology modeling of putative GmFAD2-2A, GmFAD2-2B, GmFAD2-2C, GmFAD2-2D, and GmFAD2-2E protein structures was retrieved from bar.utoronto.ca database. The PDB template used to model these structures was 4zyo and the confidence value was 99.2. The 3D molecule data used in this study come from Kelley, L. A.; Mezulis, S.; Yates, C. M.; Wass, M. N.; Sternberg, M. J. E., The Phyre2 web portal for protein modeling, prediction and analysis. Nature Protocols 2015, 10, (6), 845-858, Pfam domain data come from Finn, R. D.; Bateman, A.; Clements, J.; Coggill, P.; Eberhardt, R. Y.; Eddy, S. R.; Heger, A.; Hetherington, K.; Holm, L.; Mistry, J.; Sonnhammer, E. L.; Tate, J.; Punta, M., Pfam: the protein families database. Nucleic Acids Res 2014, 42, (Database issue), D222-30, and CDD feature hits come from Marchler-Bauer, A.; Derbyshire, M. K.; Gonzales, N. R.; Lu, S.; Chitsaz, F.; Geer, L. Y.; Geer, R. C.; He, J.; Gwadz, M.; Hurwitz, D. I.; Lanczycki, C. J.; Lu, F.; Marchler, G. H.; Song, J. S.; Thanki, N.; Wang, Z.; Yamashita, R. A.; Zhang, D.; Zheng, C.; Bryant, S. H., CDD: NCBI's conserved domain database. Nucleic Acids Res 2015, 43, (Database issue), D222-6. Homology modeling shows an amino acid modeling rate of 43.98%, 77.28%, 78.32%, 78.75%, and 92.07% for GmFAD2-2A, GmFAD2-2B, GmFAD2-2C, GmFAD2-2D, and GmFAD2-2E proteins, respectively. Mutation mapping and visualizations were performed using the UCSF Chimera package.

Example 11. GmFAD2-1 and GmFAD202 Subcellular Localization and Cloning

The GmFAD2-1A, GmFAD2-1B, GmFAD2-2A, GmFAD2-2B, GmFAD2-2C, GmFAD2-2D, and GmFAD2-2E coding sequences were amplified from "Forrest" cDNA using gene specific forward and reverse primers containing EcoRI and SalI restriction enzyme sites, respectively. The amplified PCR products were fused to the N-terminus of the yellow fluorescent protein (YFP) reporter gene in the pSAT6-EYFP-N1 vector. The fusion constructs were then verified by sequencing. Three micrograms of DNA for each plasmid were bombarded into onion epidermal cells. The pSAT6-EYFP-N1 empty vector was used as a cytoplasmic control. Onion epidermal peels were incubated at 26° C. in the dark for at least 20 hours. The subcellular localization of the fused proteins was visualized using the EVOS® FL Auto Cell Imaging System (Life Technologies). The subcellular localization experiment was repeated twice.

Example 12. Analysis of Putative Cis-Elements at the GmFAD2-1 and GmFAD2-2 Promoters Putative cis-elements in the upstream region (−2Kb upstream) of all 7 GmFAD2-1 and GmFAD2-2 gene members were searched using the programs PLACE, Plant PAN 2.0 and MatInspector. Additional filtering was carried out based on motif score and redundant repeated motifs. Next, significant motifs were searched manually using PLACE for the putative role in plant development.

Example 13. Statistical Analysis

All presented results were performed using JMP Pro 14 using the Student's t-test for comparisons of means.

Example 14. FAD2 Duplication within the Soybean Genome

Figure 3B:
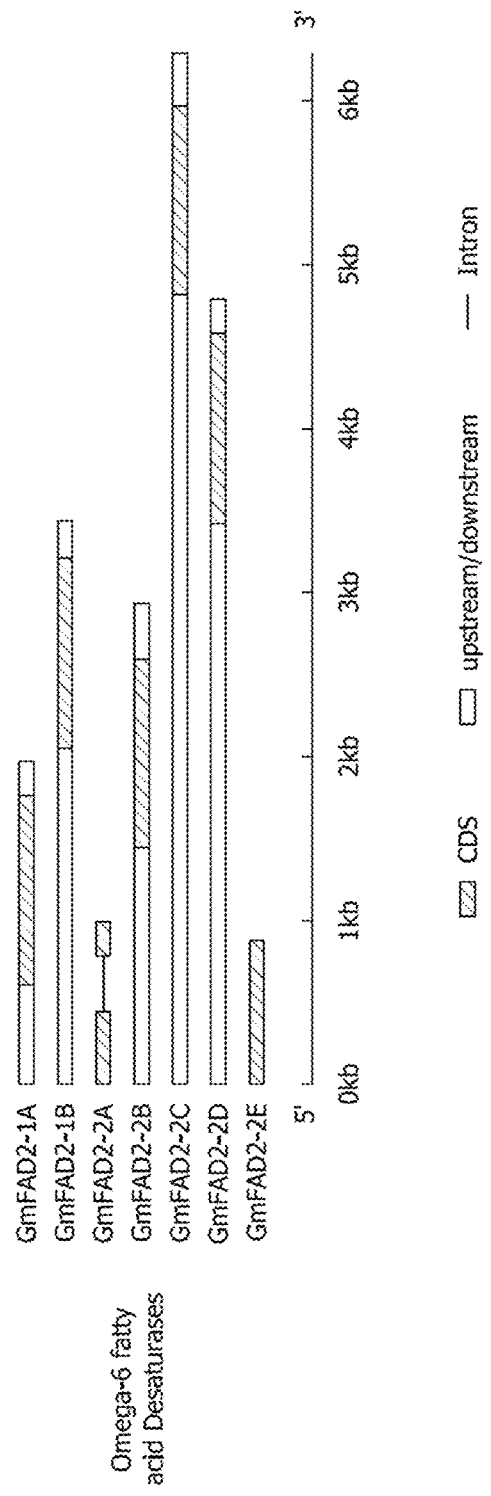

In soybeans, two GmFAD2 subfamilies were previously reported. Two members constitute the GmFAD2-1 subfamily and five members belong to the GmFAD2-2 subfamily. GmFAD2-1A and GmFAD2-1B are located on chromosomes Chrs.10 and 20, respectively. GmFAD2-2A and GmFAD2-2B are located in Tandem in Chr.19, whereas GmFAD2-2C, GmFAD2-2D, and GmFAD2-2E are located in Chr.03, 09, and 15, respectively (See FIG. 3A and FIG. 3B). The Four independent segmental duplicated blocks containing the genomic pairs GmFAD2-2A/GmFAD2-2C, GmFAD2-2A/GmFAD2-2D, GmFAD2-2D/GmFAD2-2C, and GmFAD2-1A/GmFAD2-1B were previously identified in ±100 kb duplicated regions centered around the GmFAD2 genes. However, GmFAD2-2B was not found to be a result of a segmental duplication. Synteny analysis from the current study suggests that GmFAD2-2B may be the result of a tandem duplication involving GmFAD2-2A.

The calculated ratios of non-synonymous to synonymous substitutions (Ka/Ks) of the four GmFAD2-2A/GmFAD2-2C (Ka/Ks=0.18), GmFAD2-2A/GmFAD2-2D (Ka/Ks=0.12), GmFAD2-2D/GmFAD2-2C (Ka/Ks=0.1), and GmFAD2-1A/GmFAD2-1B (Ka/Ks=0.23) gene-pairs (chromosomal duplications) were less than 1, suggesting that their evolution may follow a purifying natural selection that could act on their coding sequences. The duplication time of the five GmFAD2 members was estimated to match the recent (GmFAD2-1A/GmFAD2-1B and GmFAD2-2A/GmFAD2-2C), and old (GmFAD2-2A/GmFAD2-2D and GmFAD2-2D/GmFAD2-2C) duplication events. The segmental duplication of GmFAD2-1A/GmFAD2-1B and GmFAD2-2A/GmFAD2-2C was calculated to have occurred about 10.65 and 27.04 Mya, while the segmental duplications of GmFAD2-2A/GmFAD2-2D and GmFAD2-2D/GmFAD2-2C may have occurred 100.81 and 106.55 Mya. These data suggest that the calculated duplication time of GmFAD2-1A/GmFAD2-1B and GmFAD2-2A/GmFAD2-2C was close to the suggested recent duplication event (~13 mya). The calculated duplication time of GmFAD2-1A/GmFAD2-1B and GmFAD2-2A/GmFAD2-2C may belong to the old duplication event (~59 mya), which is consistent with the obtained soybean GmFAD2 intragenome syntenic relationships calculated earlier using the Plant Genome Duplication Database.

Example 15. Evolution of the GmFAD2 Gene Family

Figure 4:
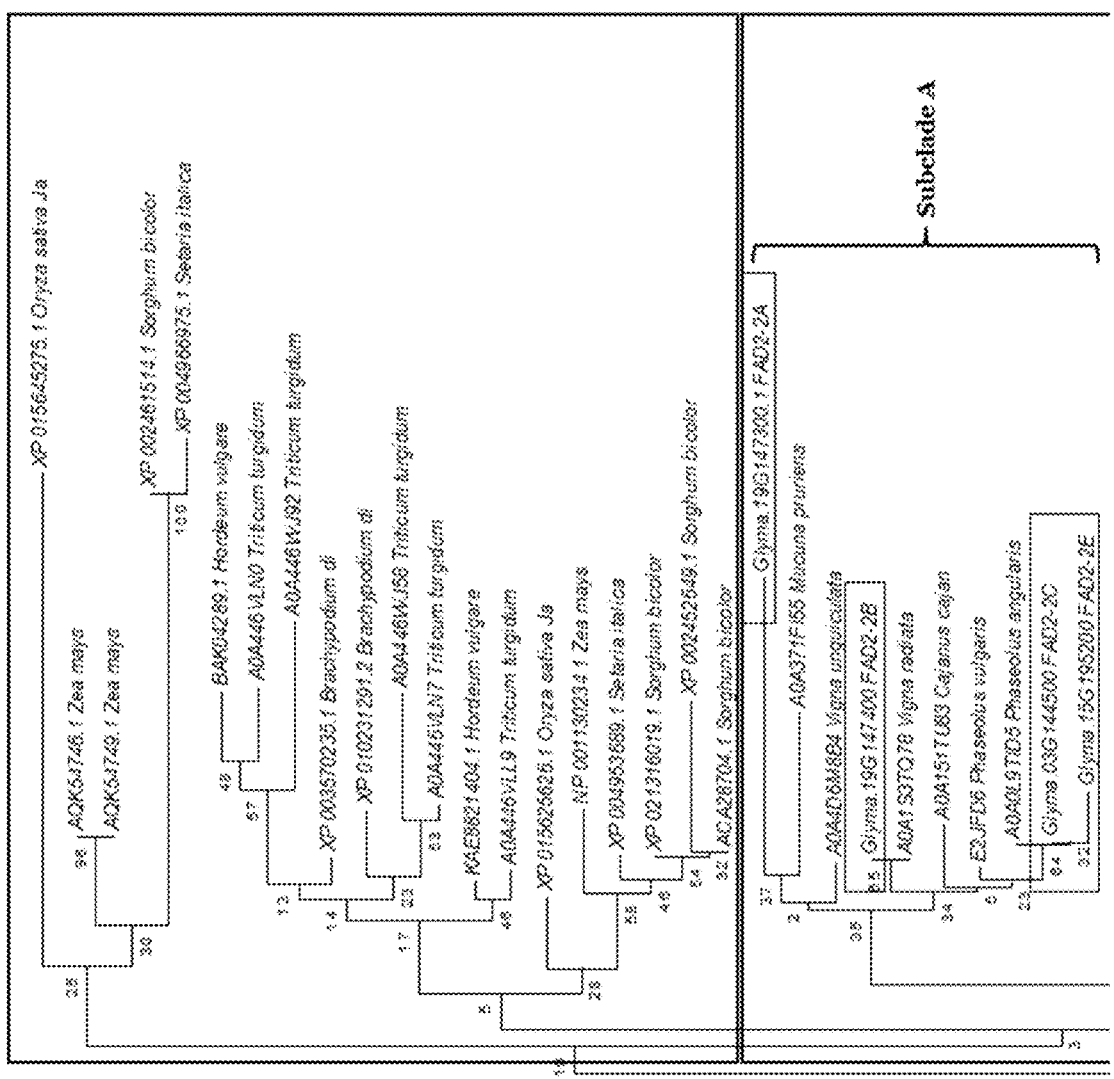
FIG. 4 is a diagram illustrating the phylogenetic tree of the fatty acid desaturase-2 from 48 sequenced plant species. FAD2 proteins identified in five model plants; C. reinhardtii (algae; green box), P. patens (moss), S. moellendorfii (lycophyte), O. sativa (monocot), and M. truncatula (eudicot leguminous), in addition to G. max (soybean) and other monocots and eudicots FAD2s were included in the analysis. The phylogenetic tree was generated using MEGA4 software package and the ClustalW algorithm, and calculated using the neighbor-joining method. The tree bootstrap values are indicated at the nodes (n=1000).
Figure 4:
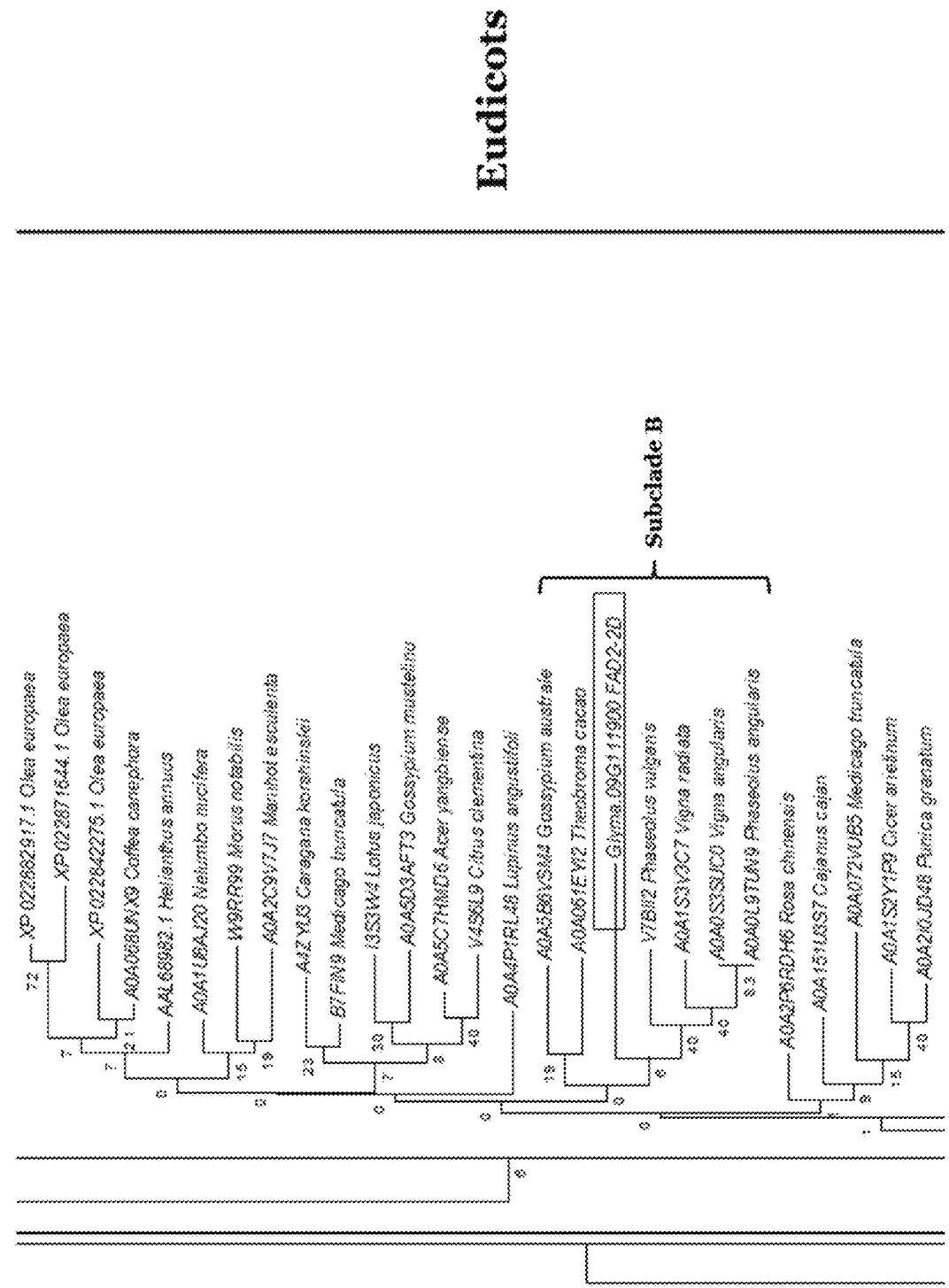
Figure 4:
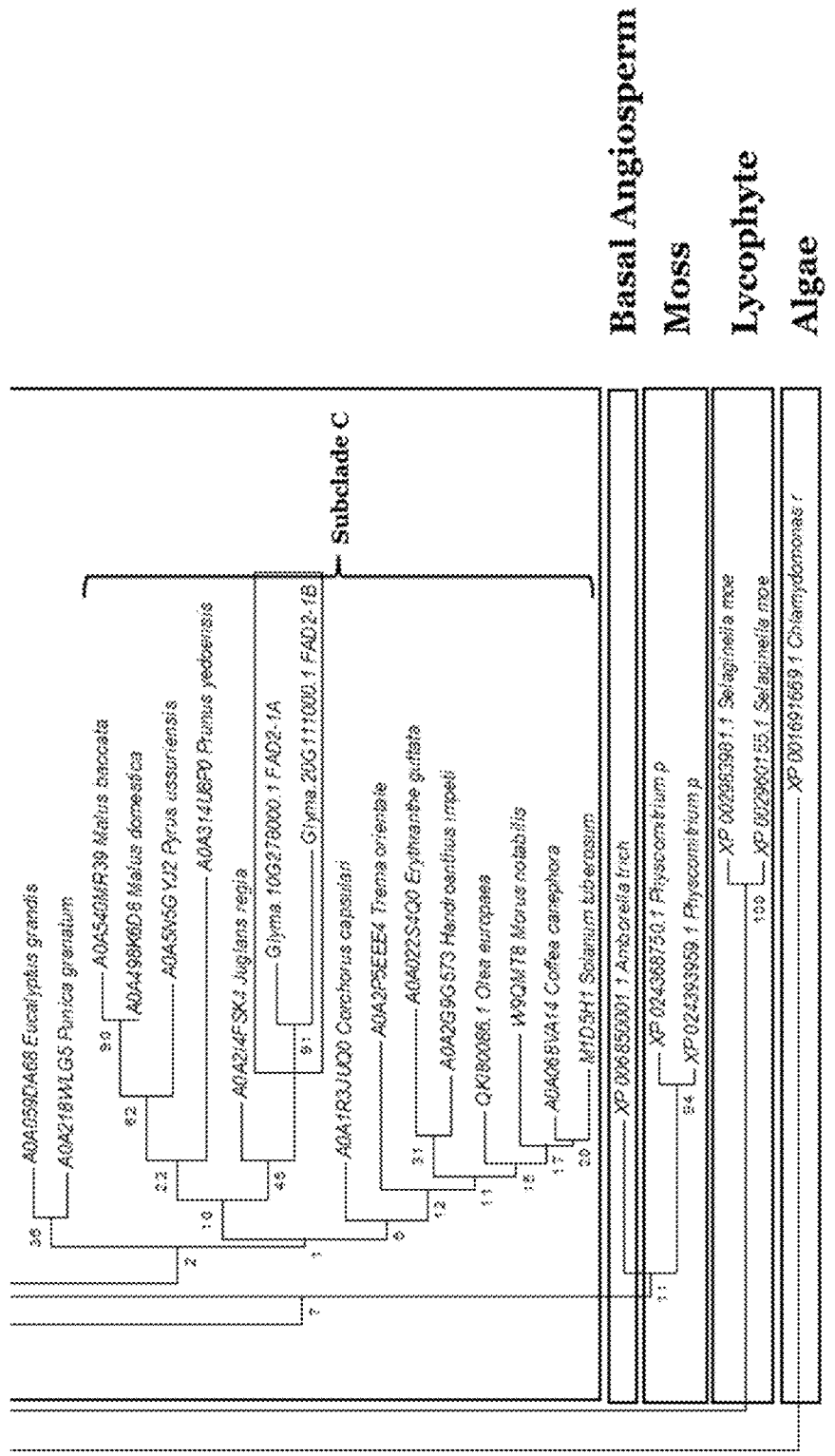

To understand the evolutionary relationships within the GmFAD2 gene family, the seven GmFAD2 protein members were aligned with orthologous protein sequences from 48 plant species, 7 monocots, 37 eudicots, and the most primitive plants including a basal angiosperm (*Amborella trichopoda*), a lycophyte (*Selaginella moellendorff*), a moss (*Physcomitrella patens*), and a chlorophyte (*Chlamydomonas reinhardtii*) (FIG. 4).

Phylogenetic analysis separately grouped FAD2s from monocot, eudicot, a basal angiosperm, and the two primitive land species (mosses and lycophytes). The analysis shows that the ancestral FAD2 from the chlorophytic algae was outgrouped. These results demonstrate clearly that the fatty acid desaturase-2 followed the typical path of evolution, from aquatic to land plant species, being essential for plant survival.

Within the eudicot clade, the analysis revealed the presence of three different subclades containing the seven FAD2 members. While the two GmFAD2-1A and GmFAD2-1B were found in the subclade (C) containing FAD2s from different tree species (Apple, Crab apple, Chinese pear, and English walnut), the other five GmFAD2-2 members were imbedded in two other different subclades containing FAD2s from several other leguminous. GmFAD2-2A, GmFAD2-2B, GmFAD2-2C, and GmFAD2-2E were grouped together in the subclade (A) and phylogenetically close to FAD2 leguminous including velvet bean, cowpea, mung bean, pigeon pea, common bean, and red mung beans (FIG. 4). The GmFAD2-2D member, was separately grouped in another subclade (B) containing other FAD2s from cacao tree, an endemic woody shrub, and FAD2 from other three leguminous (red mung bean, common bean, and mung bean).

Example 16. Expression Analysis of GmFAD2 Gene Family

Figure 5A:
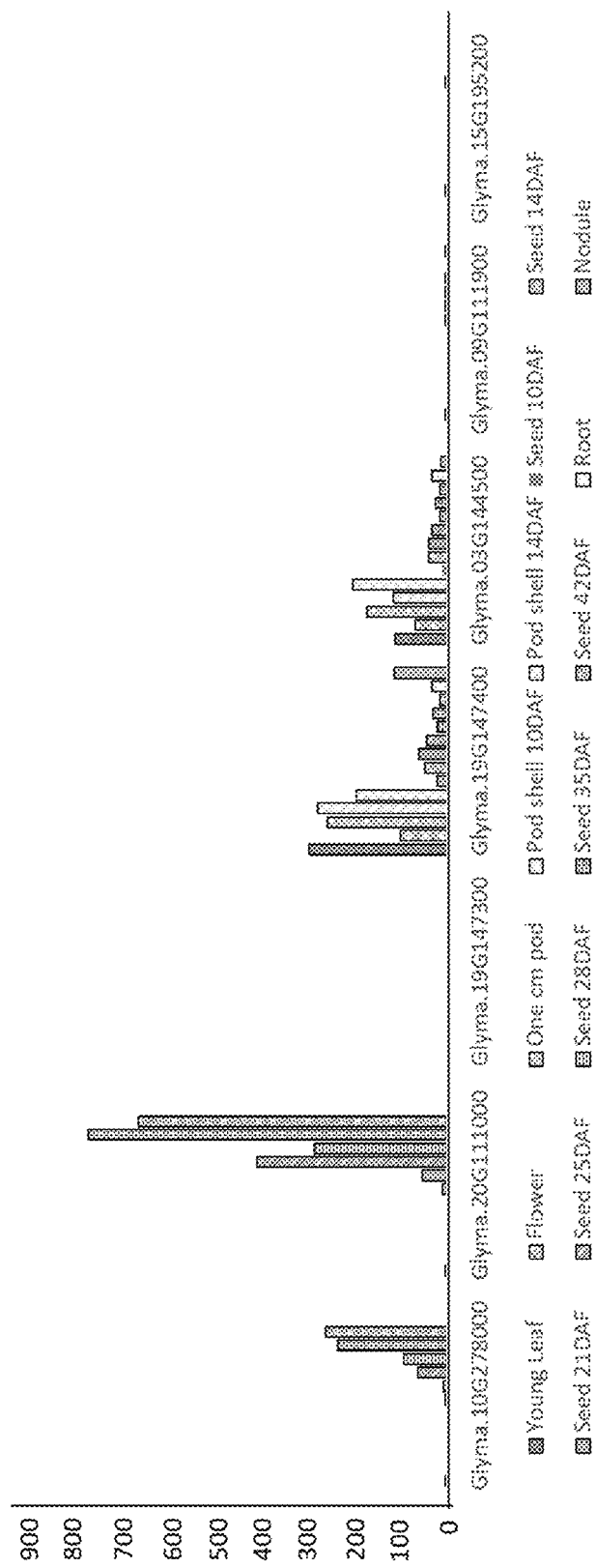
FIGS. 5A and 5B show a series of bar graphs showing the expression pattern of soybean GmFAD2-1 and GmFAD2-2 gene members.
Figure 5B:
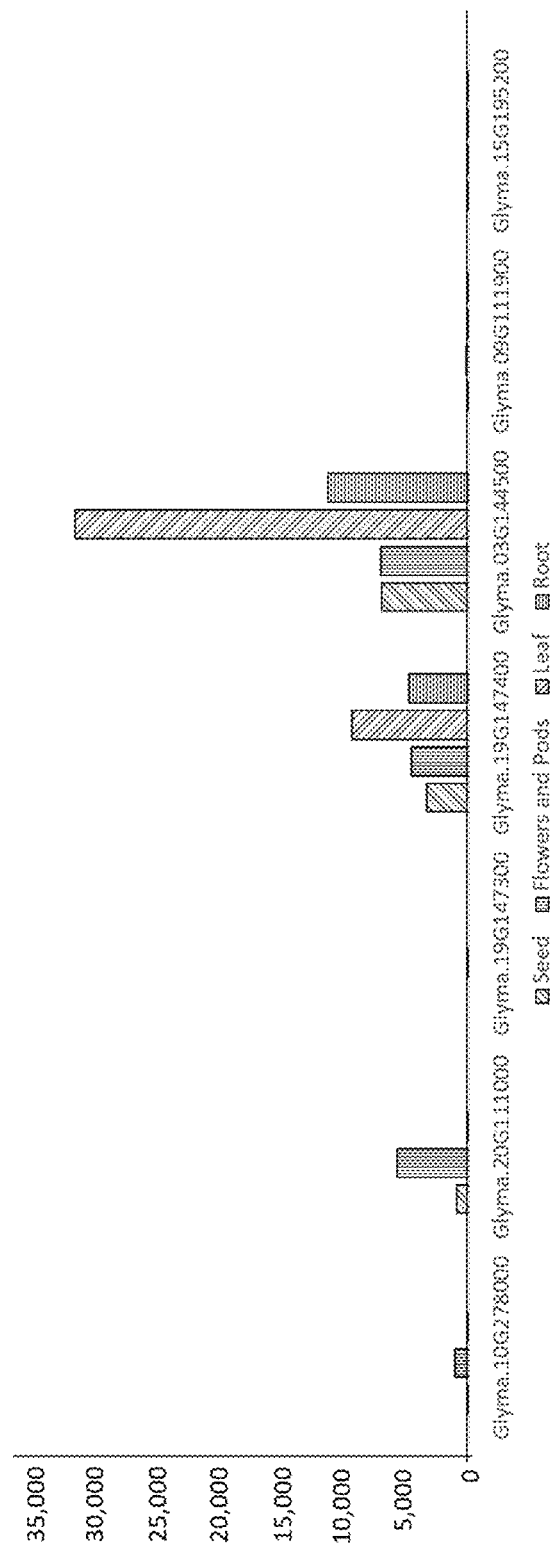
Figure 6A:
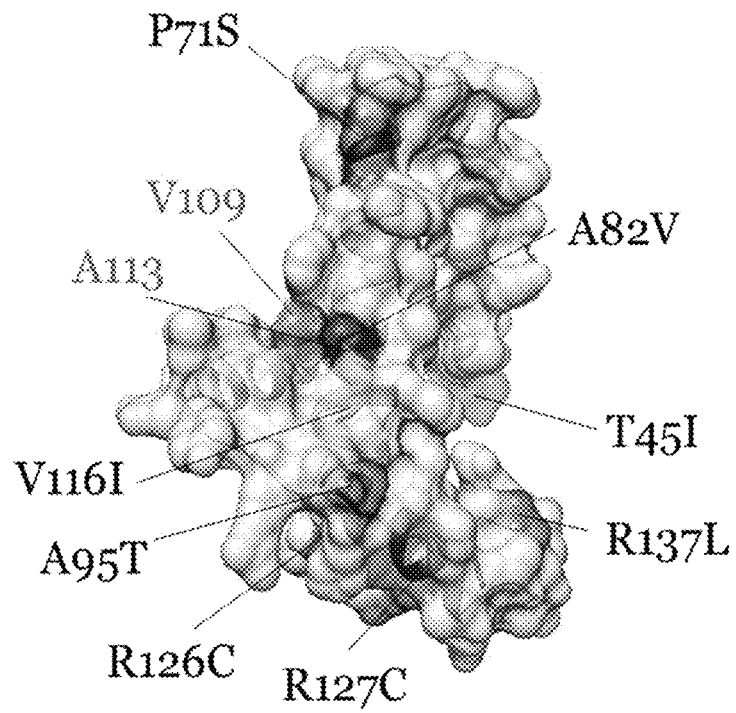
FIG. 6A through FIG. 6E are a series of 3D drawings illustrating the homology modeling of the five GmFAD2-2 proteins and corresponding identified EMS mutations. Mutated residues on the five GmFAD2-2 proteins identified by Tilling-by-Sequencing$^+$ were mapped on the five GmFAD2-2 protein homology models. Homology modeling of the GmFAD2-2A (FIG. 6A), GmFAD2-2B (FIG. 6B), GmFAD2-2C (FIG. 6C), GmFAD2-2D (FIG. 6D), and GmFAD2-2E (FIG. 6E) predicted proteins. The identified mutations and corresponding amino acid changes are shown on blue. Putative di-iron binding sites residues and substrate-binding pocket are shown in green.
Figure 6B:
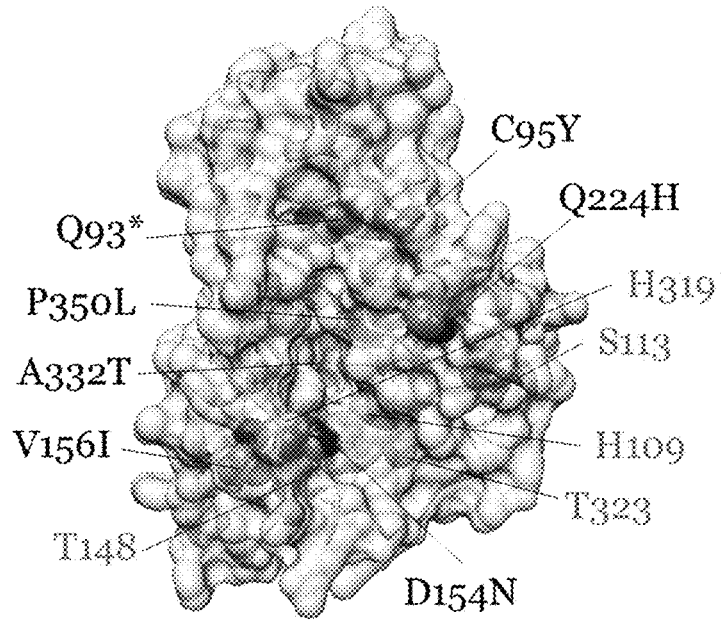
Figure 6C:
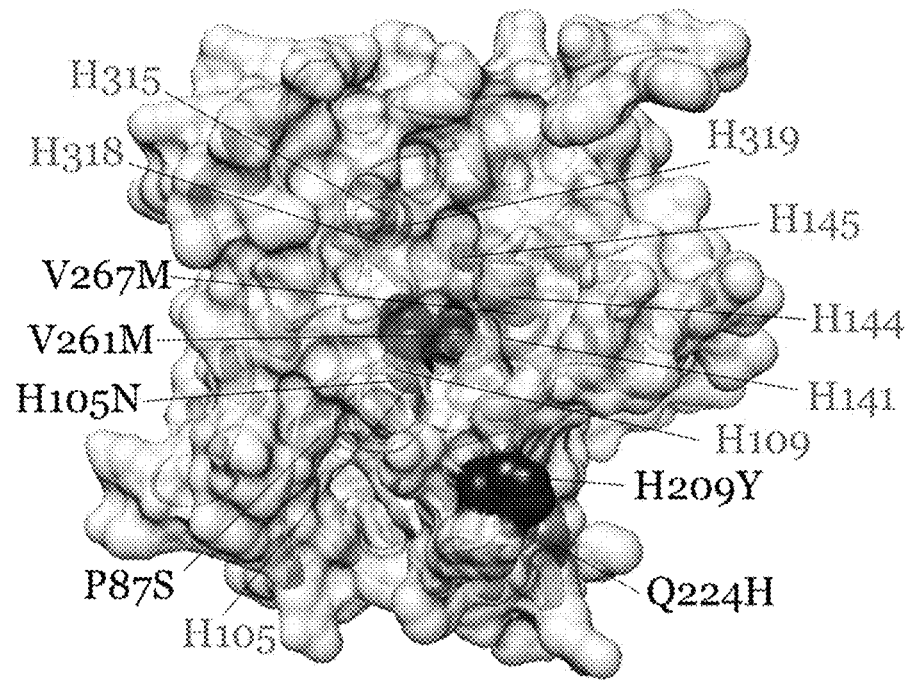
Figure 6D:
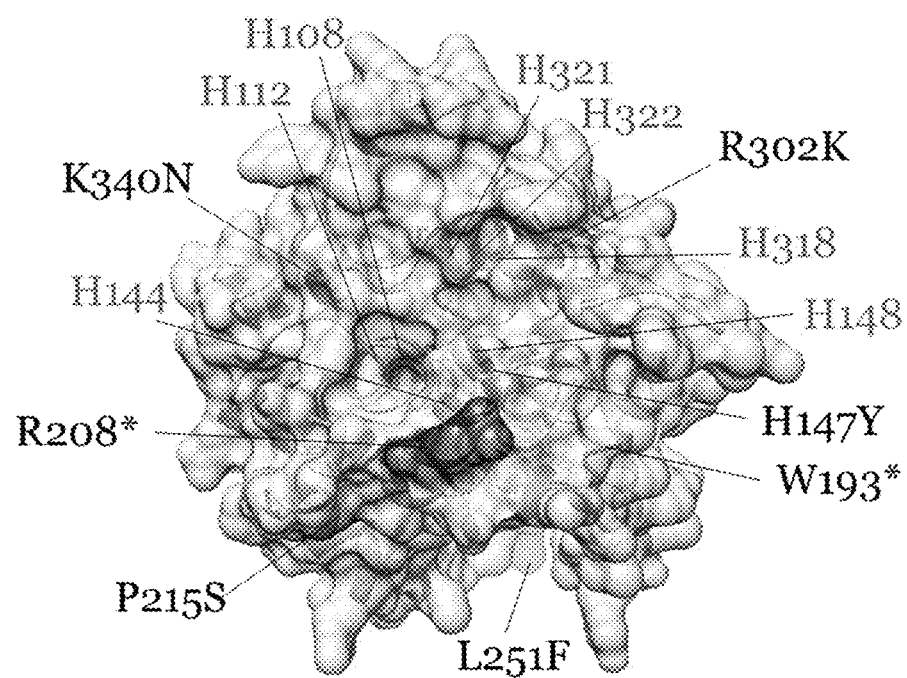
Figure 6E:
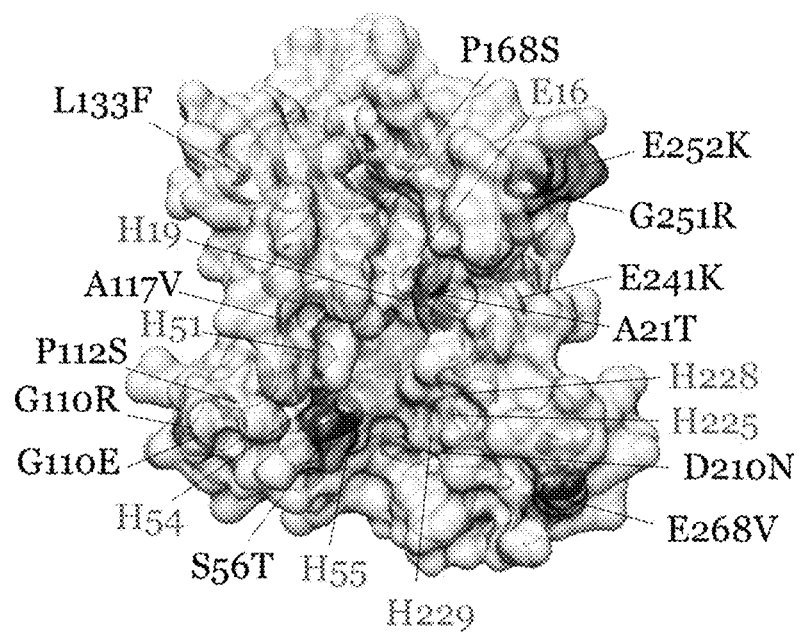

First, publicly available RNA-seq data of developing Williams 82 soybean seeds were examined. The expression pattern of all seven GrnFAD2 gene family members in the soybean reference genome Williams 82 was carried out in different tissues in order to investigate their specific evolutionary path. The two traditional GmFAD2-1A and GmFAF2-1B members showed the highest gene expression in seeds (at 35-42 DAF) (FIG. 5). When comparing members of the GmFAD2-2 gene family, both GmFAD2-2B and GmFAD2-2C transcripts were highly expressed in pod shell (at 10-14 DAF). GmFAD2-2A, GmFAD2-2D, and GmFAD2-2E showed the lowest expression.

To gain more insight into the expression of the seven GmFAD2 members in soybean cv. Forrest (MG V), which was used as a background to develop the mutagenized soybean population in this study, RNA-Seq analysis was carried out to check the expression levels of the GmFAD2 members. RNA-Seq analysis showed that GmFAD2-2B and GmFAD2-2C transcripts were highly expressed than the traditional GmFAD2-1 members in root and leaves (FIG. 5). In seeds, flower, and pods, GmFAD2-2B and GmFAD2-2C together with GmFAD2-1B transcripts were more abundant than GmFAD2-1A. GmFAD2-2A, GmFAD2-2D, and GmFAD2-2E showed the lowest expression like in Williams 82 cultivar.

Example 17. TILLING by Target Capture Sequencing

To identify novel allelic variation within the GmFAD2 gene family, a population of 4,032 EMS mutagenized soybeans was developed using the "Forrest" cultivar. Next, Tilling-by-Sequencing+ was used to identify several mutants from GmFAD2-2A, GmFAD2-2B, GmFAD2-2C, GmFAD2-2D, and GmFAD2-2E. Using this reverse genetic approach, we successfully identified twelve GmFAD2-2A, nine GmFAD2-2B, twelve GmFAD2-2C, nine GmFAD2-2D, and nineteen GmFAD2-2E missense mutants (See FIG. 6A through FIG. 6E).

Example 18. Mutation Density of the "Forrest" EMS Mutagenized Population

The first soybean TILLING mutagenized populations were produced with a mutation density corresponding to ~1/140 kb and ~1/550 kb using EMS or N-nitroso-N-methylurea (NMU), respectively. TILLING-by-Sequencing+ analysis of the seven fatty acid desaturase genes resulted in the identification of 441 SNP mutations and 16 InDels (FIG. 7). About 74% of mutations were the typical EMS mutations (G to A and C to T), while the other type of mutations account for about 26% of the total mutations. The mutation density is estimated to be ~1/155 kb, ~1/154 kb, ~1/128 kb, ~1/138, ~1/102, ~1/121, and ~1/67 kb for the GmFAD2-1A, GmFAD2-1B, GmFAD2-2A, GmFAD2-2B, GmFAD2-2C, GmFAD2-2D, and GmFAD2-2E genes, respectively. Within the coding regions, 50% to 70% of missense mutations, 1% to 8% of nonsense mutations, and 22% to 26% of silent mutations were obtained (See FIG. 3A and FIG. 3B).

Example 19. All Five GmFAD2-2s are Involved in High Oleic Acid Content

The identified EMS mutants were mapped on the five GmFAD2-2 protein models (See FIG. 6A through FIG. 6E). The results showed that most of the mutations were mapped on key protein domains including the catalytic activity of the enzyme (di-iron center), homodimer interface, and/or substrate binding, suggesting that the isolated mutations may have a negative impact on protein activity and/or dimerization.

Most importantly, all isolated missense and nonsense Gmfad2-2a, Gmfad2-2b, Gmfad2-2c, Gmfad2-2d, and Gmfad2-2e mutants showed a significant increase in their seed oleic acid content when compared to the wild-type "Forrest" (FIG. 8). Mutations on GmFAD2-2A, GmFAD2-2B, GmFAD2-2C, GmFAD2-2D, and GmFAD2-2E resulted in an oleic acid increase with up to 31.9%, 28.1%, 29.6%, 32.7, and 35.7%, respectively. Our results showed that GmFAD2-2A, GmFAD2-2B, GmFAD2-2C, GmFAD2-2D, and GmFAD2-2E play an unprecedented role in unsaturated fatty acid biosynthesis in soybeans, suggesting that members of the GmFAD2-2 subfamily may have been subfunctionalized in soybeans during the two whole genome duplication events.

Figure 9:
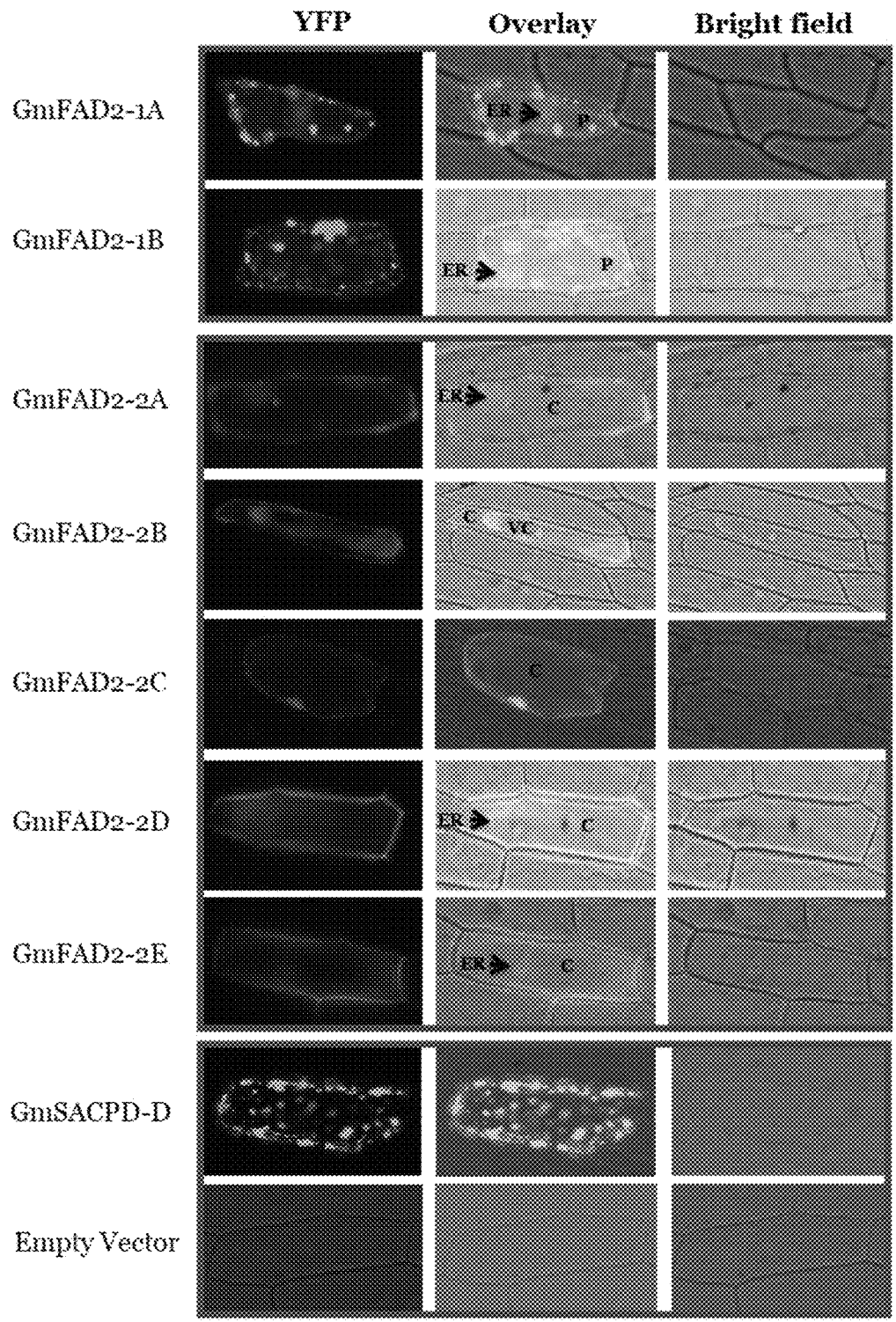
FIG. 9 is a series of pictures showing the subcellular localization of soybean GmFAD2-1 and GmFAD2-2 proteins. The GmFAD2 coding sequences from all 7 members were fused to eYFP and delivered into onion epidermal cells using biolistic bombardment. GmFAD2-1A and GmFAD2-1B showed an endoplasmic reticulum (ER) and chloroplastic (P) localization pattern. GmFAD2-2A, GmFAD2-2D, and GmFAD2-2E showed a reticulum endoplasmic and cytosol (C) localization. GmFAD2-2C signal was found in the cytosol only. GmFAD2-2B shows a vacuole (VC) and cytoplasmic localization. The chloroplast-targeted GmSACPD-D was used as positive controls. Bar=100 µM.

Example 20. Subcellular Localization of GmFAD2-1 and GmFAD2-2 Subfamily Members Although FAD2 genes were involved in converting oleic acid into linoleic acid, several subcellular localization patents of the FAD2 genes have been reported in different plant species. It has been shown that the fatty acid desaturase-2 from other plant species like *Arabidopsis thaliana*, *Artemisia sphaerocephala*, cucumber, and spinach are located in the endoplasmic reticulum. Several studies have predicted the endoplasmic reticulum localization of the GmFAD2-1A and GmFAD2-1B proteins. However, up to date, no study has shown the subcellular localization of the two GmFAD2-1 and/or the five GmFAD2-2 subfamily members in soybean. In order to gain more insight into the function of the fatty acid desaturases-2 in soybeans, their subcellular localization was examined using YFP fusion in onion epidermal cells using biolistic bombardment. Onion epidermal cells expressing GmFAD2-1s:YFP fusion confirmed their localization in the endoplasmic reticulum, but also showed an interesting expression pattern in the chloroplasts (FIG. 9). The accumulation of GmFAD2-1A and GmFAD2-1B in the endoplasmic reticulum and chloroplast is consistent with the role of this class of proteins in fatty acid desaturation reported earlier. GmFAD2-2s:YFP fusion showed a distinct pattern localization from GmFAD2-1s:YFP (FIG. 9). While GmFAD2-2C signal was found only in the cytosol, GmFAD2-2B signal was located mainly in the vacuole, in addition to the cytosol. The other three members, GmFAD2-2A, GmFAD2-2D, and GmFAD2-2E showed a reticulum endoplasmic localization in addition to the presence of a cytosolic signal.

Figure 10A:
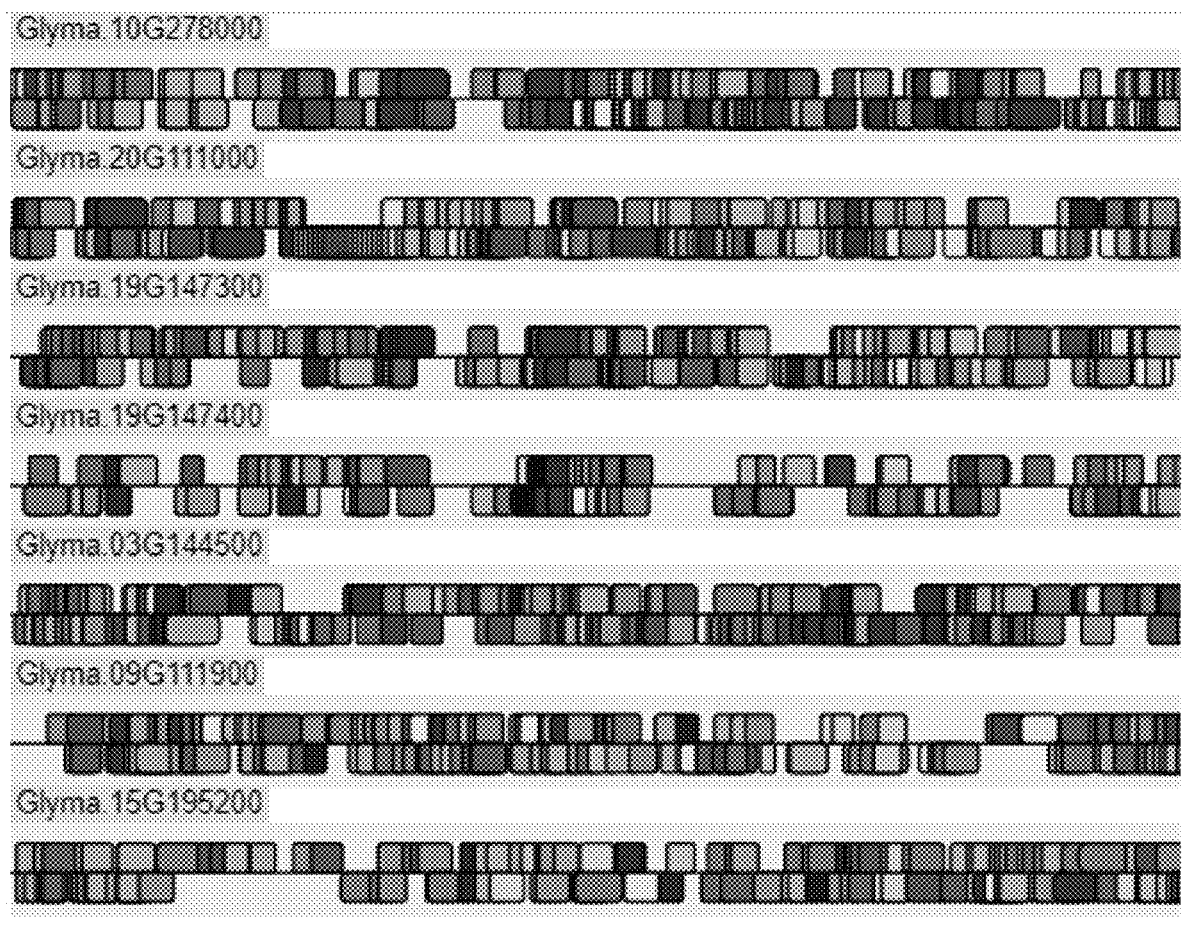
FIG. 10A and FIG. 10B are a series of diagrams illustrating the analysis of putative cis-elements in the promoter region of the GmFAD2-1 and GmFAD2-2 gene members.
Figure 10A:
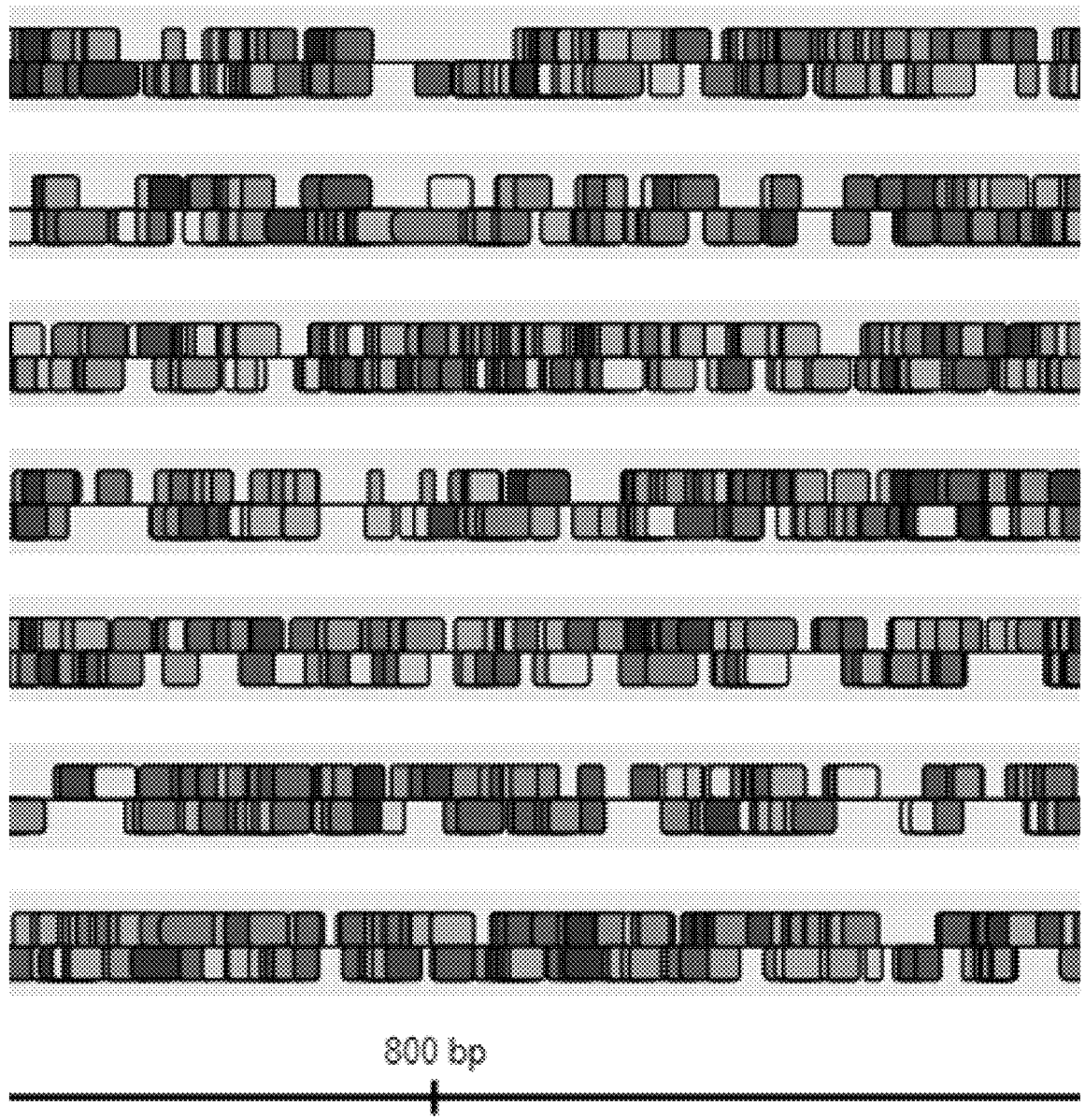
Figure 10A:
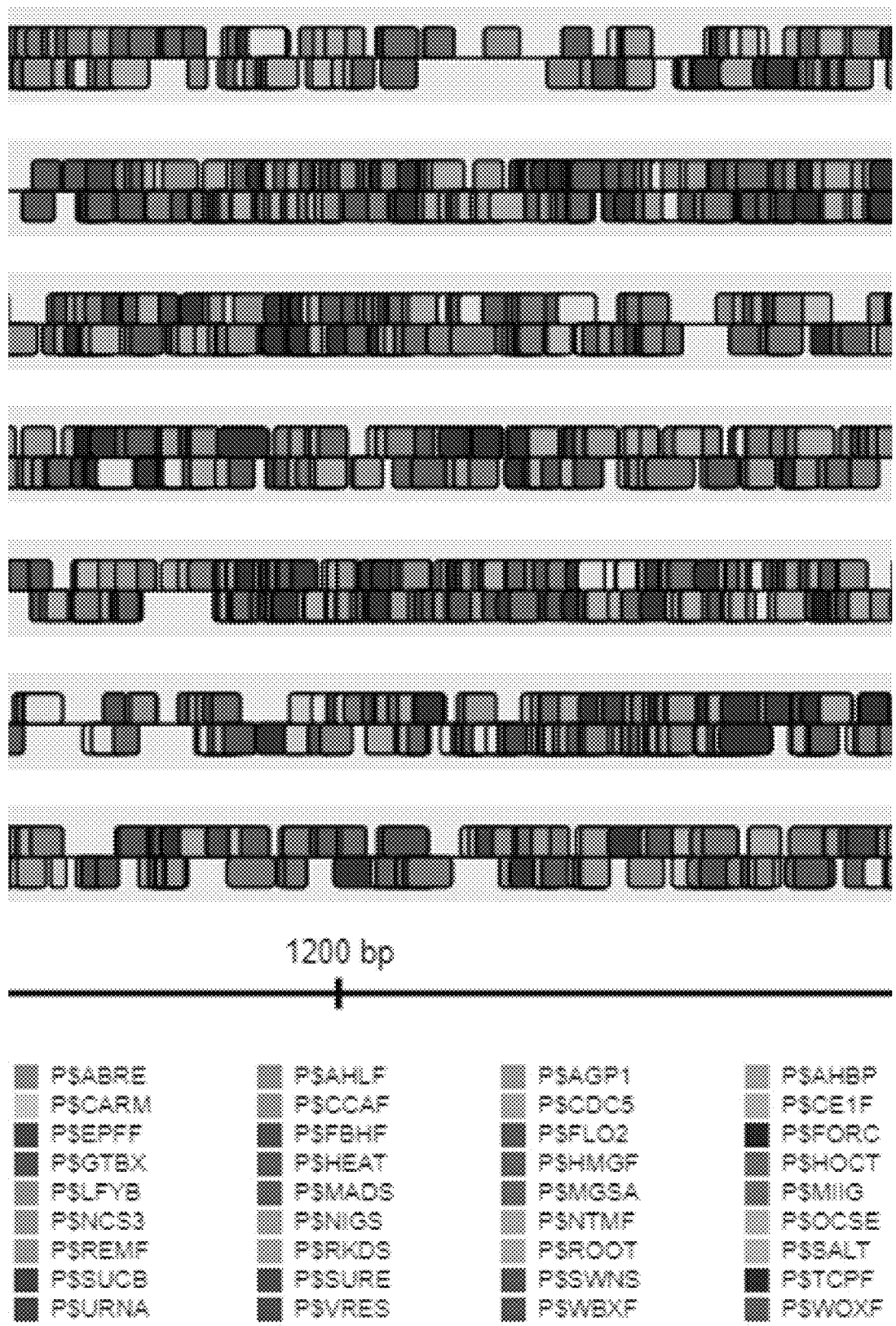
Figure 10A:
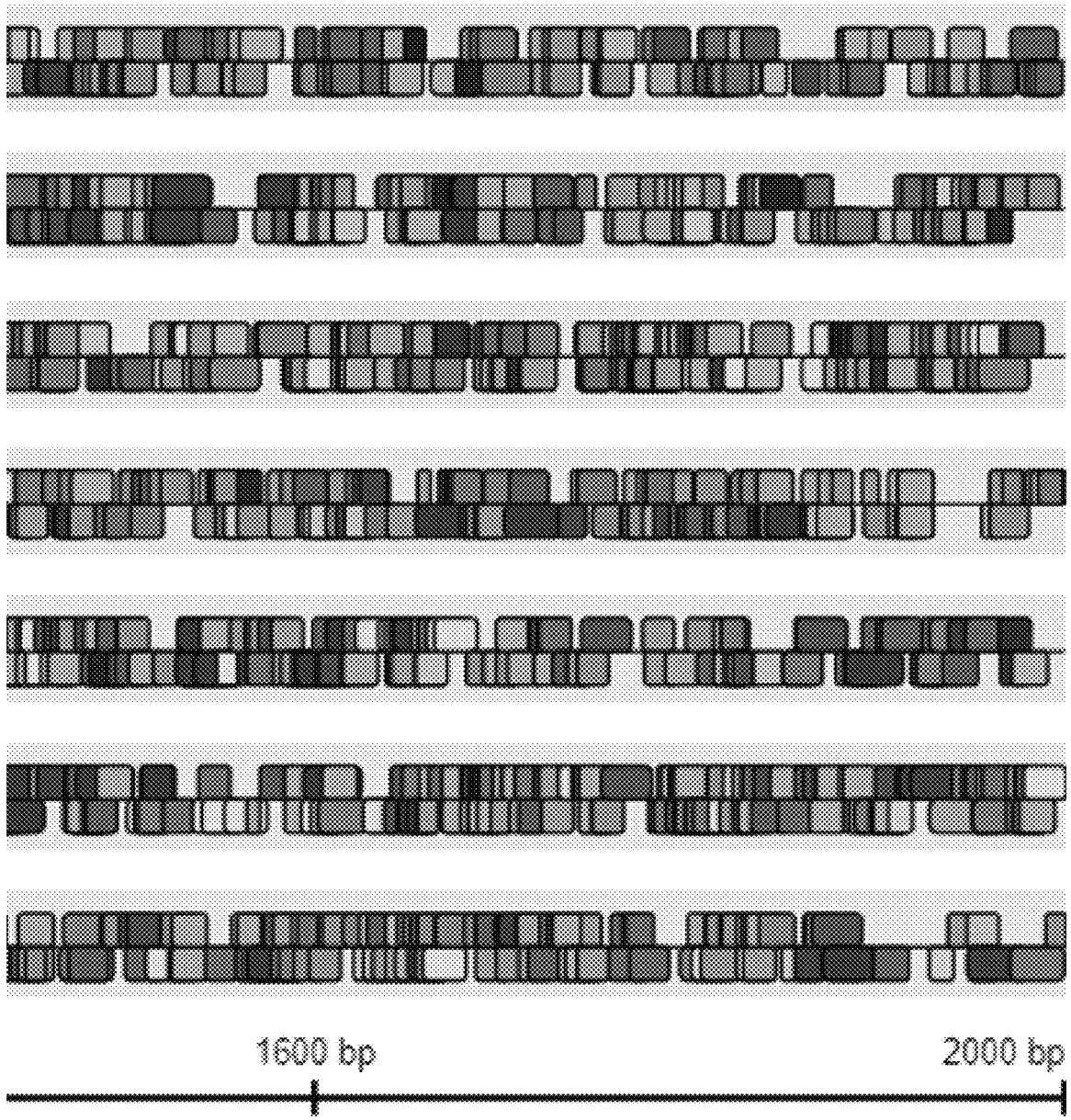
Figure 10B:
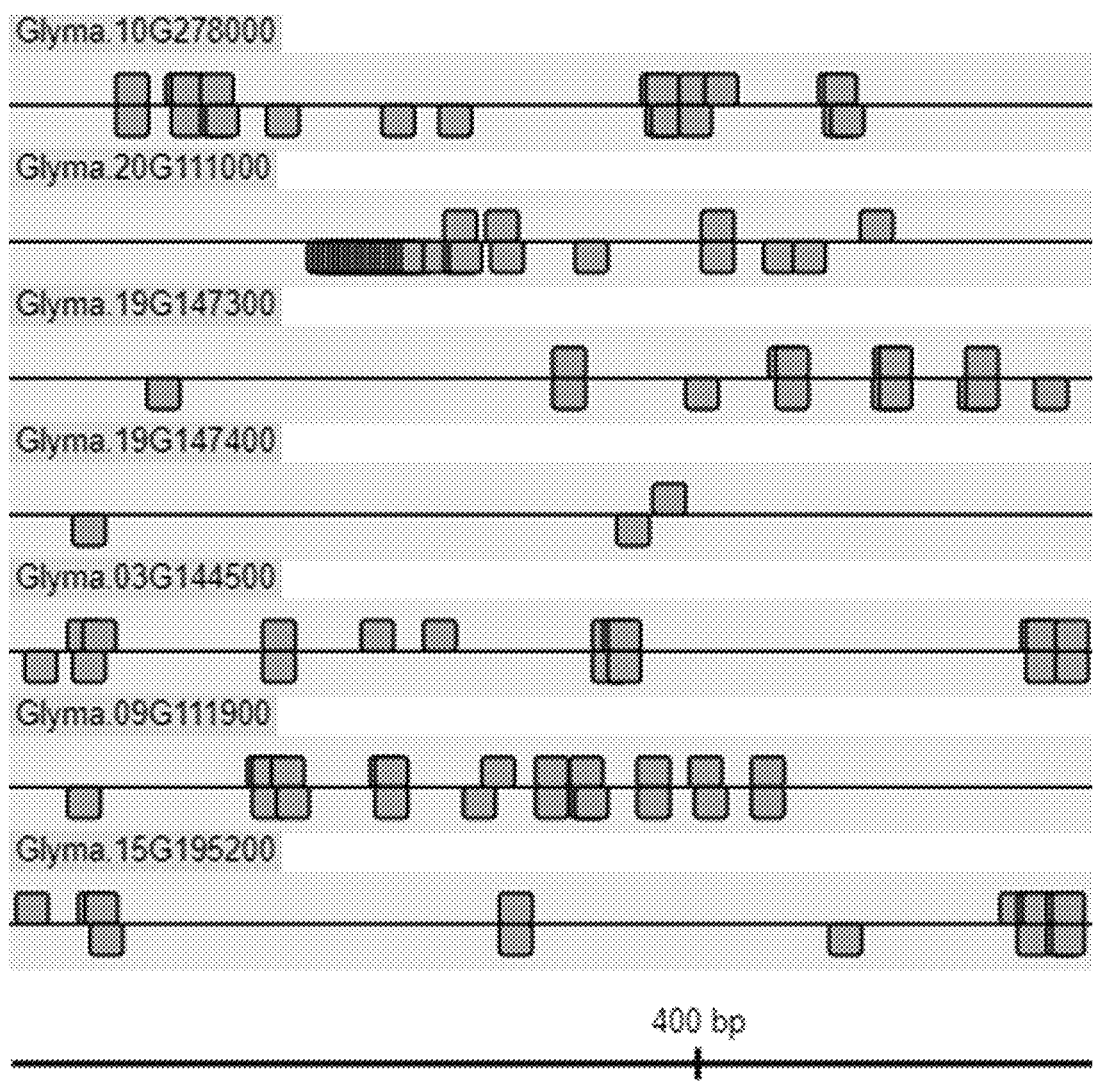
Figure 10B:
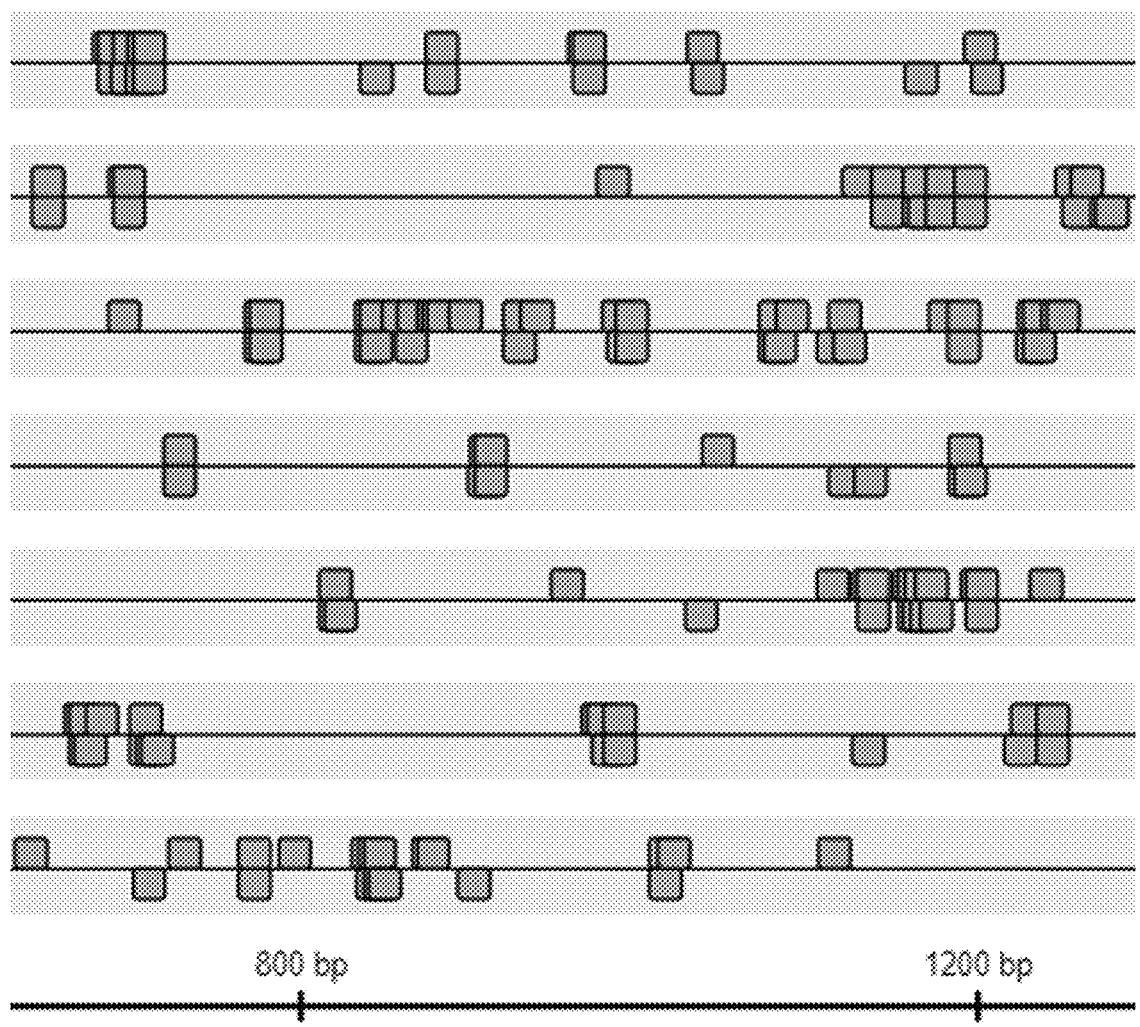
Figure 10B:
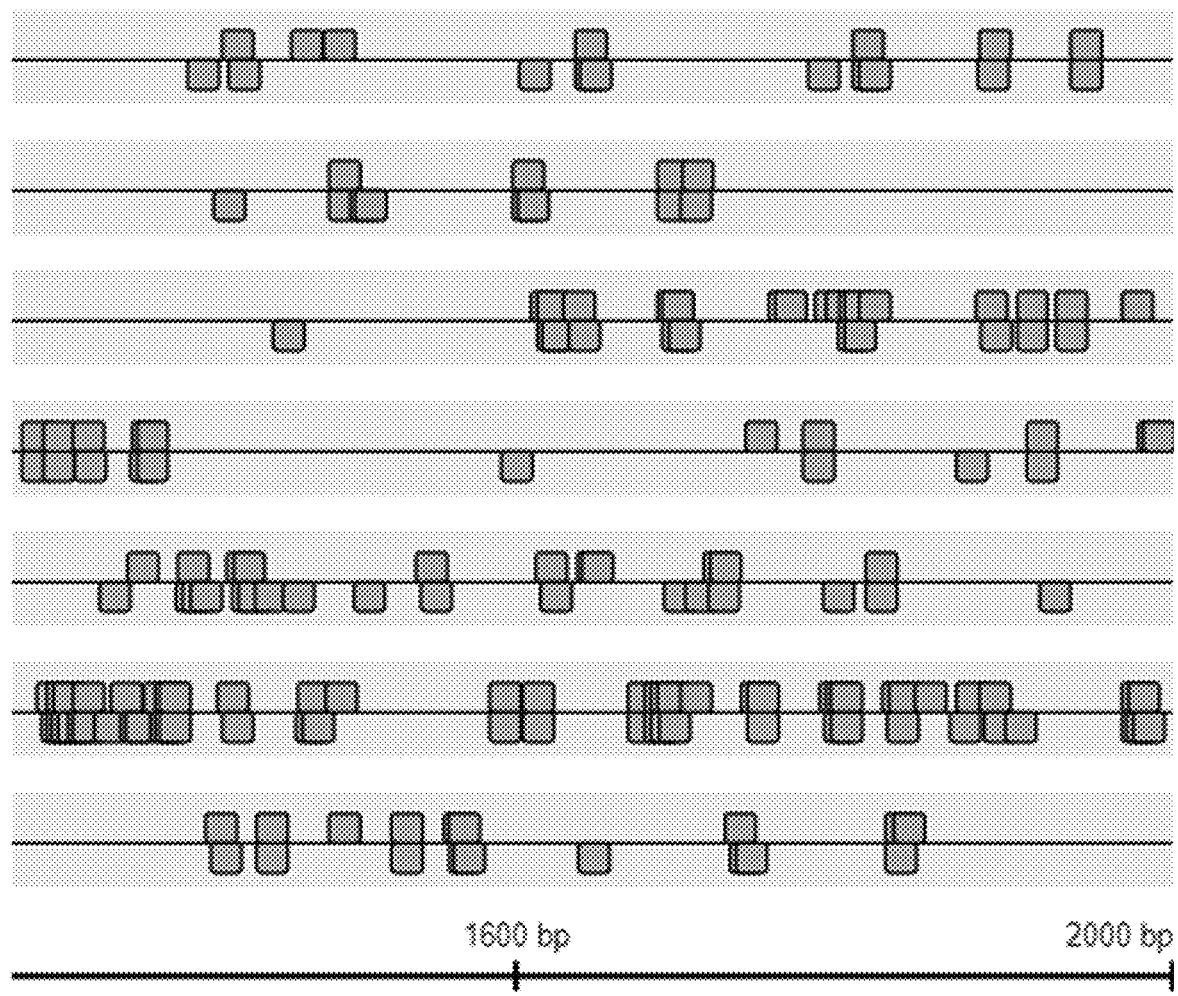

Example 21. Analysis of Putative Cis-Elements in the Ptomoter Region of GmFAD2-1 and GmFAD2-2 Gene Members The analysis of putative cis-elements in the promoter region (-2Kb upstream) of the translation start codon of GmFAD2-1 and GmFAD2-2 gene members showed an enrichment of a cis-binding motifs for the *Arabidopsis* homeobox protein domain (See FIG. 10A and FIG. 10B). The frequency of this cis-element was significantly higher (459) when compared to the other cis-elements that are present in the GmFAD2s promoter region (2.65 to 459 times higher). The promoter analysis shows that GmFAD2-1A, GmFAD2-1B, GmFAD2-2A, GmFAD2-2B, GmFAD2-2C, GmFAD2-2D, and GmFAD2-2E promoters contain 59, 64, 81, 34, 67, 102, and 52 *Arabidopsis* homeobox protein binding elements, respectively. An extremely high presence of the *Arabidopsis* homeobox protein binding element was also observed in GmFAD2-1A and GmFAD2-1B promoter regions (81 and 102, respectively). These data may suggest an involvement of *Arabidopsis* homeobox protein in the oleic acid biosynthesis. This is coherent with a previous study showing the involvement of a homeodomain transcription factor in lipid metabolism. In fact, overexpression of the epidermis-specific homeodomain-leucine zipper IV transcription factor Outer Cell Layer1 in maize identifies target genes involved in lipid metabolism and cuticle biosynthesis.

Figure 11:
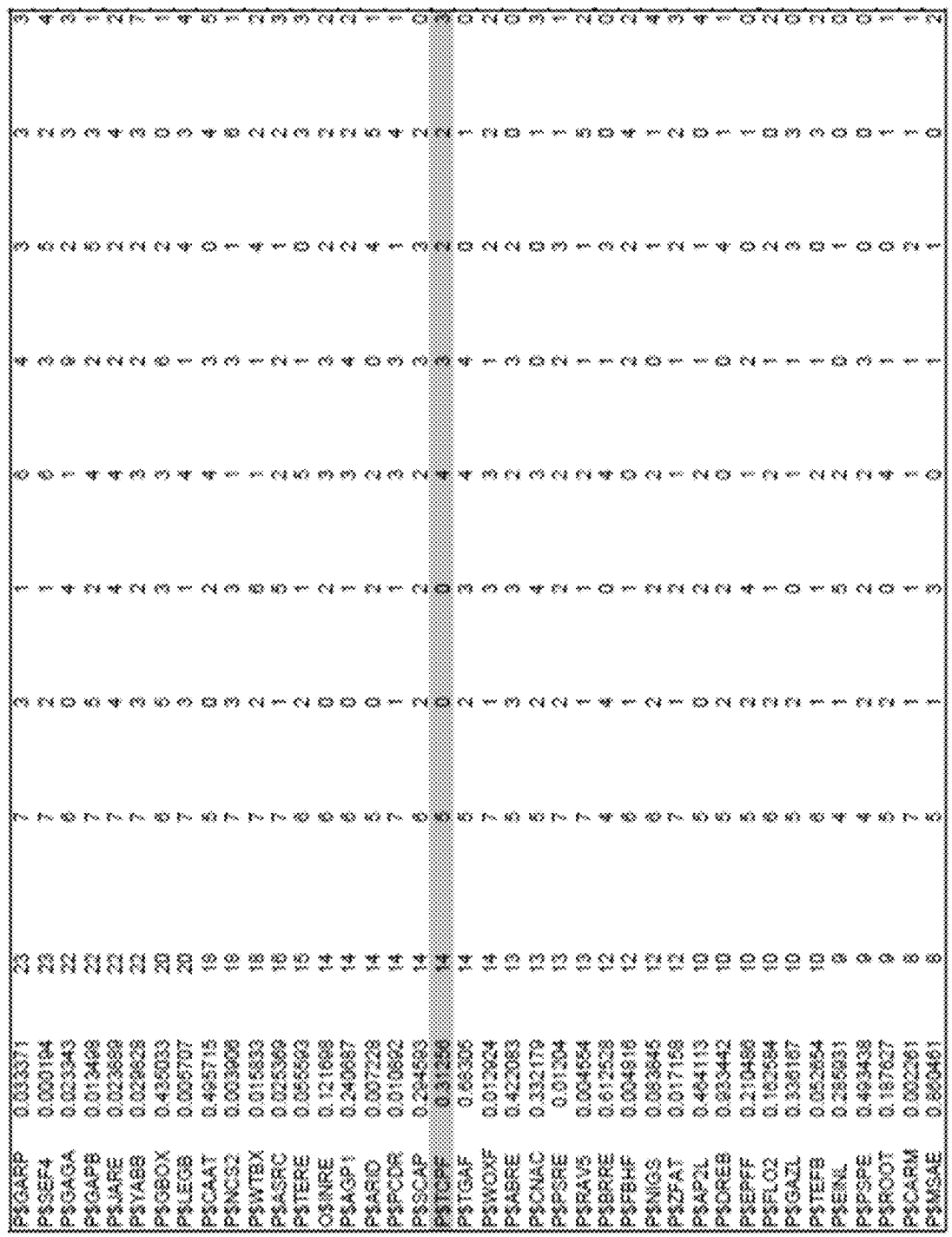
FIG. 11 is a table showing the summary of the identified cis-elements at the promoter region (−2 Kb upstream) of the translation start codon of GmFAD2-1 and GmFAD2-2 gene members showing an enrichment of the Arabidopsis homeobox protein domain within the seven GmFAD2 members.
Figure 11:
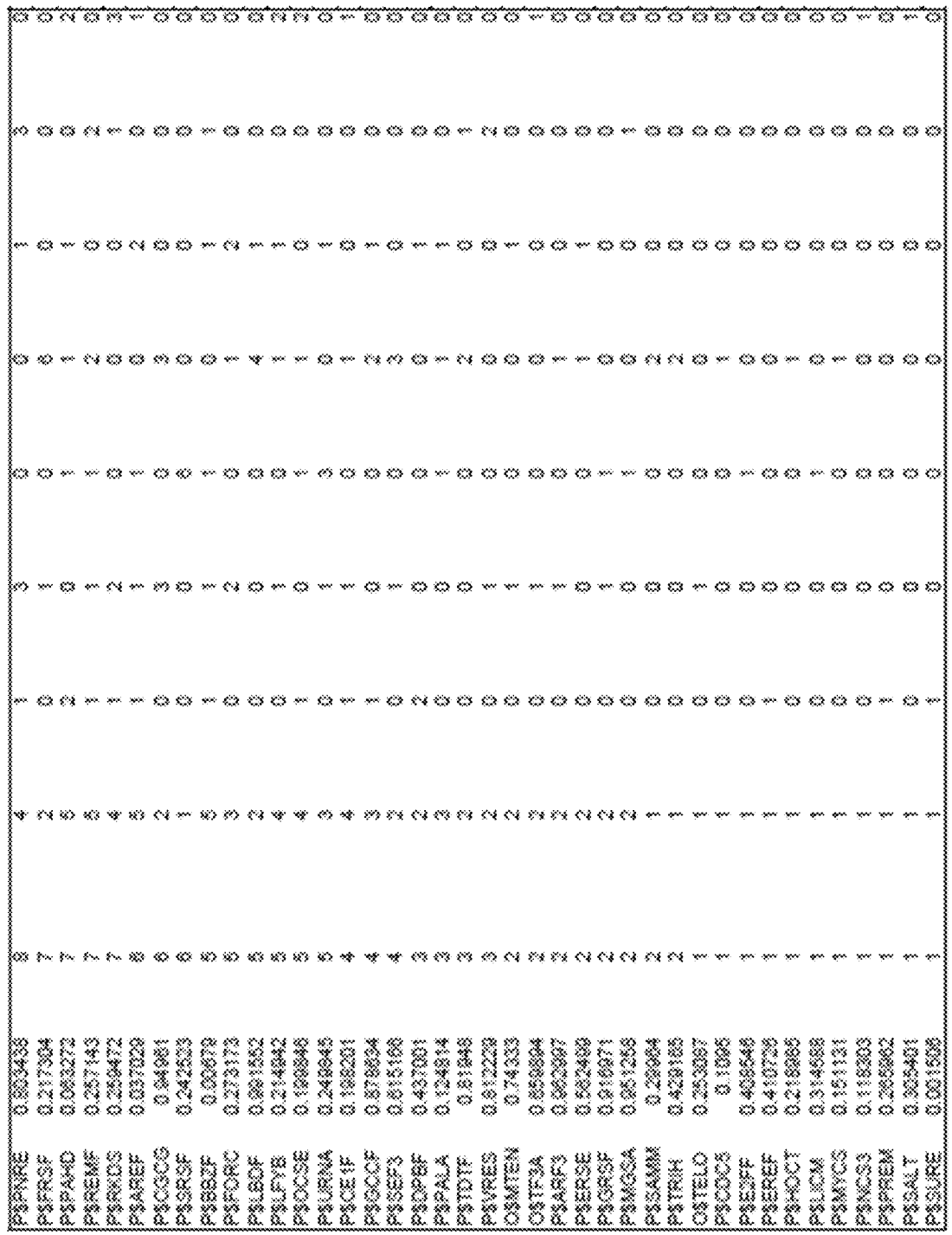

Additionally, the promoter analysis revealed the absence of the DNA-binding proteins with the plant specific TCP-domain in the GmFAD2-1 subfamily that was shared only between the five members of the GmFAD2-2 subfamily (FIG. 11). The presence of this cis-element within the GmFAD2-2 subfamily only may be linked to specific mode of regulation taking into consideration the subcellular localization pattern that was different from the GmFAD2-1 subfamily.

Figure 12:
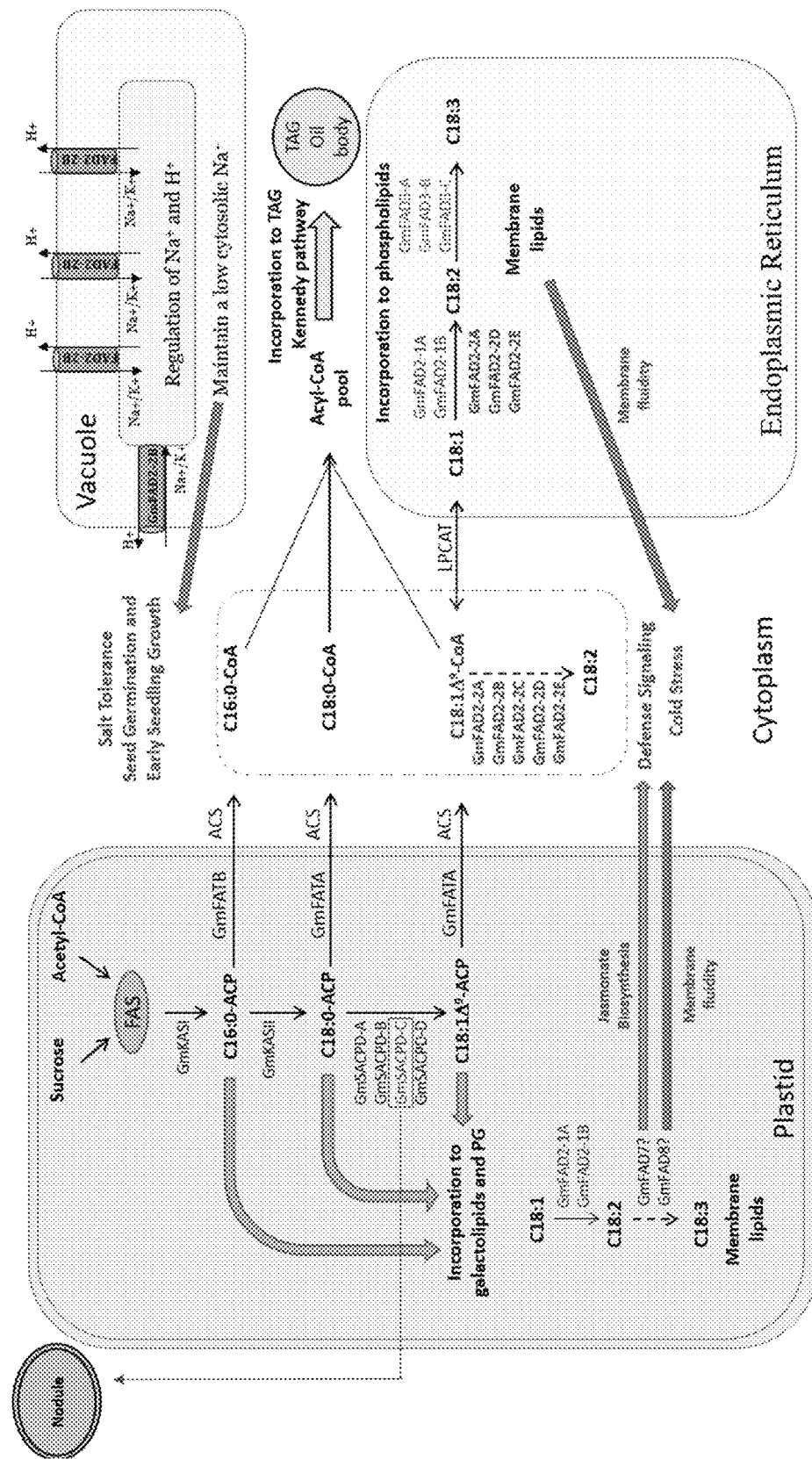
FIG. 12 is a diagram deciphering the soybean seed fatty acid biosynthesis pathway. The seven GmFAD2-1 and GmFAD2-2 members are responsible for converting oleic acid (C18:0-ACP) to linoleic acid (C18:1Δ$^9$-ACP) in the plastid (GmFAD2-1A and GmFAD2-1B), ER (GmFAD2-1A, GmFAD2-1B, GmFAD2-2A, GmFAD2-2D, and GmFAD2-2E), and cytoplasm (GmFAD2-2A, GmFAD2-2B, GmFAD2-2C, GmFAD2-2D, and GmFAD2-2E). GmFAD2-2B is located in the vacuole and are likely to play a role during seed germination and early seed growth by maintaining low cytosolic Na$^+$ as described in Arabidopsis. In bold are the five newly identified Fatty acid desaturases involved in the unsaturated fatty acid biosynthesis. GmFAD2-2A, GmFAD2-2B, GmFAD2-2C, GmFAD2-2D, and GmFAD2-2E members present a good alternative for converting oleic acid content without substantially altering the traditional plastidial/ER fatty acid production pathway in soybean. The flux of fatty acids between the plastid and the ER occurs among different plant species. A portion of C16:0-ACP, C18:0-ACP, and C18:1-ACP pool can be incorporated into phosphatidylglycerol (PG) and galactolipids in the plastid. A portion of the acyl-CoA moieties can be incorporated into triacylglycerol (TAG, the major lipid fraction in plant seed oils) biosynthesis in the seed via the Kennedy pathway. GmFAD3 genes are differentially expressed during seed development or cold temperature exposure. The GmFAD7/8 promote C18:3 biosynthesis in the plastid, acting as precursors for the biosynthesis of Jasmonate and are expected to be involved in defense responses and biotic stress signaling. GmSACPD-C is the nodule specific isoforms as shown earlier.

Example 22. Involvement of the Five GmFAD2-2 Members in the Unsaturated Fatty Acid Pathway Several studies have investigated the role and function of the FAD2 genes in several plant species. FAD2s were well studied and known for their roles in unsaturated fatty acid biosynthesis by converting oleic acid to linoleic acid. Traditionally, fatty acids are synthesized in plastid/endoplasmic reticulum. In soybeans, members of the GmFAD2-1 subfamily have been reported to increase seed oleic acid. The endoplasmic reticulum subcellular localization of the traditional GmFAD2-1A and GmFAD2-1B subfamily members is consistent with the subcellular localization reported earlier in other plant species including shrub and Arabidopsis. In cucumber, while the retention signal of some fatty acid desaturases like CsFAD2 and CsFAD3 was found to target the endoplasmic reticulum, other fatty acid desaturases like CsFAD4, CsFAD5, CsFAD6, CsFAD7 and three CsFAB2s contained a predicted chloroplast signal peptide. This is consistent with the chloroplastic localization of the GmFAD2-1A and GmFAD2-1B proteins shown in this study. EMS induced and spontaneous occurring mutations at the GmFAD2-1A and GmAD2-1B genes were widely used in the soybean breeding programs to increase seed oleic acid content up to 85% after combining the two alleles to generate double GmFAD2-1A/GmFAD2-1B mutants. However, very little is known about the role of the other members of the GmFAD2-2 subfamily. Using TILLING-by-Sequencing$^+$, we successfully identified several mutations within the five members of the GmFAD2-2 subfamily and showed for the first time their involvement in increasing seed oleic acid content (FIG. 12). Interestingly, in addition to their subcellular cytoplasmic localization, GmFAD2-2A, GmFAD2-2D, and GmFAD2-2E members have shown an endoplasmic reticulum localization, while GmFAD2-2B showed a clear vacuole localization (FIG. 12). Although fatty acids were shown to be synthesized in Plastid/endoplasmic reticulum (ER), it has been reported that this synthesis can also happen directly from malonyl-CoA in the cytoplasm without substantially altering plastidial/ER fatty acid production, known as "denovo pathway". Therefore, the presence of such pathway in soybean involving members of the GmFAD2-2 subfamily may have a positive impact on developing soybean lines with increased fatty acid and/or high very long chain polyunsaturated fatty acids that present several benefits for human health (FIG. 12).

Moreover, the accumulation of GmFAD2-2B in the cytosol and vacuole may suggest another role in controlling fatty acid desaturation at the plasma membrane and controlling ion exchange activity impacting the fluidization of membrane lipids, being essential for abiotic stress tolerance and early seedling growth (FIG. 12). In fact, the Arabidopsis fatty acid desaturase AtFAD2 was shown to play an essential role in plant resistance to salt stress by controlling the $Na^+/H^+$ exchange activity. The Arabidopsis AtFAD2 mediates a high-level of vacuolar and plasma membrane fatty acid desaturation. Plants maintaining a high $Na^+/H^+$ ratio in the cytosol show a high tolerance to soil salinity, a major abiotic stress that results in considerable crop yield losses worldwide. Additionally, it is also essential for the proper function of membrane attached $Na^+/H^+$ exchangers to maintain a low cytosolic $Na^+$ concentration for salt tolerance during seed germination and early seedling growth in Arabidopsis. The observed differences on subcellular localization may suggest that the GmFAD2-2B member underwent a process of neofunctionalization within the soybean genome, unlike the rest of the GmFAD2-2 members. Our subcellular localization data of the two GmFAD2 subfamily members is congruent with the evolution pattern shown earlier, which suggests that their evolution pattern may dictate their subcellular localization.

Up to date, soybean geneticists and breeders have heavily used induced mutations (EMS and fast neutron), natural variations and/or genetic engineering approaches to increase oleic acid content up to 85%. TALEN and CRISPR technologies were recently used to create targeted mutations based on GmFAD2-1A/GmFAD2-1B genes. The available high oleic acid soybeans based on GmFAD2-1A/GmFAD2-1B alleles (plastidial/ER fatty acid production) present affected germination in cold soil. Loss of function of the GmFAD2-1A and GmFAD2-1B may affect the incorporation of fatty acids into phospholipids in the Endoplasmic Reticulum impacting membrane lipids and membrane fluidity; therefore, affecting cold stress tolerance and fatty acid stability of these lines. Thus, the discovery of new fatty acid desaturases impacting positively the seed oleic acid content without disturbing the plastid/ER pathway and subsequent incorporation to phospholipids is extremely beneficial to develop alternate strategy to improve seed oleic acid in soybean and their commercialization (FIG. 12).

Example 23. Sub-Functionalization of GmFAD2-2 Gene Family During Whole Genome Duplication The soybean genome has been diversified due to the presence of two different large-scale duplication events (~13 and 59 million years ago), resulting in a paleopolyploid genome where three quarter of the genes are present in multiple copies, impacting the development of important agronomic traits. As a consequence of these two duplication events, the two GmFAD2-1 and GmFAD2-2 subfamilies resulted in seven GmFAD2 members that derived from three independent syntenic duplicated genomic regions and one tandem duplication. These data may suggest the existence of a common FAD2 ancestor. The identification of a single FAD2 gene in *C. reinhardtii* in addition to the evolutionary conservation of the FAD2 proteins among soybeans from phylogenetically separated species further support this feature. Additionally, the fact that all five members of the GmFAD2-2 subfamily are involved in the unsaturated fatty acid biosynthesis, similar to the GmFAD2-1 subfamily, points to the presence of a subfunctionalization event of the GmFAD2 gene family, which may be most probably the result of successive duplications of an ancestral FAD2, leading to the enhancement of soybean oil biosynthesis. Like the GmFAD2-1 subfamily, stacking more GmFAD2-2 members is expected to provide additive effect leading to increasing the seed oleic acid content in soybean without the alteration of the plastidial/ER fatty acid production. The presence of subfunctionalization event has been reported earlier in soybeans. Two members of the Soluble NSF attachment proteins, the GmSNAP18 and GmSNAP11, have subfunctionalized to play a role in resistance to soybean cyst nematode, in addition to the four members of the Stearoyl-acyl carrier protein desaturases, which have been subfunctionalized to play a role in the fatty acid unsaturation by converting seed stearic acid to seed oleic acid. Furthermore, the observed substantial changes in GmFAD2 gene expression may be most probably due to gene duplication and selection pressure imposed by environmental conditions. This may explain functional differences of the oleic acid and linoleic acid contents observed within the two GmFAD2 gene subfamilies. Although the current study showed the potential of using members of the GmFAD2-2 gene subfamily to develop soybean lines with increased seed oleic acid content, their specific role in the cytoplasm/plasma membrane needs to be further investigated.

The invention claimed is:

1. A transgenic soybean plant with increased oleic acid content transformed with a polynucleotide encoding a fatty acid desaturase (FAD) related promoter that functions in the soybean plant operably linked to a polynucleotide encoding a polypeptide having FAD activity,
wherein the polypeptide having FAD activity comprises a sequence at least 95% identical to wild type "Forrest" FAD2-2E amino acid sequence (SEQ ID NO: 29) and further comprises one or more mutations selected from the group consisting of A21T, S56F, S56T, G110E, G110R, P112S, A117V, L133F, P168S, W199R, G202E, R209K, D210N, H236Y, E241K, G251R, E252K, E268V, and P277S, and
wherein the FAD related promoter comprises a sequence selected from the group consisting of wild type "Forrest" FAD2-2A (SEQ ID NO: 15), wild type "Forrest" FAD2-2B (SEQ ID NO: 18), wild type "Forrest" FAD2-2C (SEQ ID NO: 21), wild type "Forrest" FAD2-2D (SEQ ID NO: 24), and wild type "Forrest" FAD2-2E (SEQ ID NO: 27) nucleotide sequence.

2. The plant of claim 1, wherein the increased oleic acid content represents an at least about 1% increase in oleic acid content as compared to a control soybean plant lacking the polynucleotide encoding a polypeptide having FAD activity.

3. The plant of claim 1, wherein the plant has been transformed with two or more polynucleotides, each encoding a FAD related promoter that functions in the soybean plant, provided that each polynucleotide encoding a FAD related promoter that functions in the soybean plant is operably linked to a polynucleotide encoding a polypeptide having FAD activity,
wherein at least one polypeptide having FAD activity comprises a sequence at least 95% identical to a nucleotide sequence selected from the group consisting of wild type "Forrest" FAD2-2A (SEQ ID NO: 17), wild type "Forrest" FAD2-2B (SEQ ID NO: 20), wild type "Forrest" FAD2-2C (SEQ ID NO: 23), wild type "Forrest" FAD2-2D (SEQ ID NO: 26), and wild type "Forrest" FAD2-2E amino acid sequence (SEQ ID NO: 29), and
wherein at least one FAD related promoter comprises a sequence selected from the group consisting of wild type "Forrest" FAD2-2A (SEQ ID NO: 15), wild type "Forrest" FAD2-2B (SEQ ID NO: 18), wild type "Forrest" FAD2-2C (SEQ ID NO: 21), wild type "Forrest" FAD2-2D (SEQ ID NO: 24), and wild type "Forrest" FAD2-2E (SEQ ID NO: 27) nucleotide sequence.

4. A method of increasing the oleic acid content of a soybean plant, the method comprising:
transforming the soybean plant with a polynucleotide encoding a fatty acid desaturase (FAD) related promoter that functions in the soybean plant operably linked to a polynucleotide encoding a polypeptide having FAD activity,
wherein the polypeptide having FAD activity comprises a sequence at least 95% identical to wild type "Forrest" FAD2-2E amino acid sequence (SEQ ID NO: 29) and further comprises one or more mutations selected from the group consisting of A21T, S56F, S56T, G110E, G110R, P112S, A117V, L133F, P168S, W199R, G202E, R209K, D210N, H236Y, E241K, G251R, E252K, E268V, and P277S, and
wherein the FAD related promoter comprises a sequence selected from the group consisting of wild type "Forrest" FAD2-2A (SEQ ID NO: 15), wild type "Forrest" FAD2-2B (SEQ ID NO: 18), wild type "Forrest" FAD2-2C (SEQ ID NO: 21), wild type "Forrest" FAD2-2D (SEQ ID NO: 24), and wild type "Forrest" FAD2-2E (SEQ ID NO: 27) nucleotide sequence.

5. The method of claim 4, wherein the increased oleic acid content represents an at least about 1% increase in oleic acid content as compared to a control soybean plant that is not transformed with a polynucleotide encoding a polypeptide having FAD activity.

* * * * *

SEQUENCE LISTING

<160> NUMBER OF SEQ ID NOS: 29

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
cacattcagc aaaacaactg a                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
tgtactaata catgacaaaa c                                              21

<210> SEQ ID NO 3
<211> LENGTH: 22
<212> TYPE: DNA
<213> ORGANISM: Artificial Sequence
<220> FEATURE:
<223> OTHER INFORMATION: Synthetic

<400> SEQUENCE: 3
gtattagaca ttcagcaaca ac                                             22

<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
ttaagtgata agtgacaaaa c                                              21

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
gttcatgaaa agtgcatggt                                                20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
attcatccta aaccgtcaca                                                20

<210> SEQ ID NO 7
<211> LENGTH: 20
<212> TYPE: DNA
<213> ORGANISM: Artificial Sequence

```
<220> FEATURE:
<223> OTHER INFORMATION: Synthetic

<400> SEQUENCE: 7
tcgctttgat gagaaacatt                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
acaaaggaaa gttcaaacca                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
gttcattctg attcggtgag                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
cccaataagc aaccatgata                                               20

<210> SEQ ID NO 11
<211> LENGTH: 23
<212> TYPE: DNA
<213> ORGANISM: Artificial Sequence
<220> FEATURE:
<223> OTHER INFORMATION: Synthetic

<400> SEQUENCE: 11
ttgatgagtt agttttgcaa tta                                           23

<210> SEQ ID NO 12
<211> LENGTH: 22
<212> TYPE: DNA
<213> ORGANISM: Artificial Sequence
<220> FEATURE:
<223> OTHER INFORMATION: Synthetic

<400> SEQUENCE: 12
tttataagac ccataaggaa ca                                            22

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
tcaccatagc cttctacctc                                               20
```

<210> SEQ ID NO 14
<211> LENGTH: 21
<212> TYPE: DNA
<213> ORGANISM: Artificial Sequence
<220> FEATURE:
<223> OTHER INFORMATION: Synthetic

<400> SEQUENCE: 14

```
agcaaccatg ctactaaaca g                                              21
```

<210> SEQ ID NO 15
<211> LENGTH: 2000
<212> TYPE: DNA
<213> ORGANISM: Glycine max

<400> SEQUENCE: 15

```
atattttaag tgatgcgtga gtgaatgctt ctctctaaag gaaggaagag aatgtaaaaa      60
atctatactc acaagagaat aaggaaaata agtttcattt ttaagtttgt cccacatagg     120
acatcttgca gttgggtacg cctatgcatt tatttacacg aaaatgttgt gctgcgctgt     180
taattggacc acaaacatgc aacgtacatg caatcaaaat tgctgttcac tagggagata     240
attctcgcca taagttcctg tggctgtggc tgtggctgtg acacatttag tgcatattaa     300
aattttcatt cataagtttg gattaaattt aaatttgcaa attgaatttg tagaaagaac     360
ccaaatcttt tatatataaa actcagtttc aggaaaaact ttaatgcaca aactttgttt     420
taaaaggtaa tcaacatgtt acaaaatcga attaattttc gaatagtttt tagcaccaaa     480
cagtattttt ttttagaaa taacatcttt aatgatcaaa acttaaagat atctatttt      540
attatcttta gagtatatta aattattttt attttaaga aattttagag atgagttgtt     600
tattaagata ctcaagtcaa aactgaagaa atccaccatg cttaattcac aatgcttaac     660
tggatttatc caacaacaaa agaaaataaa aaattacttt tttctcctaa gaaactcatc     720
aagcatcttt cattggagat gacttaactt tctttgaaag aaaagagacg acaataatca     780
tggtggtccg ggttttttaa acgcaatgtg tttagaaagt gatatatatg gcttttttat     840
aattattttg ttaacttatt tcattaagct ttaggattat tattatatat aaaaattact     900
ttatttcaat atcaattaca attacaataa tgccacatta tgttttatgt acgacgatgt     960
tgtaagttgg tgttgtccaa gtacttaatt aaattattga gtactagtaa cccagttttt    1020
catatacact ctcttattgg ttaaaatata ttaaaaacta taaaatcaag taagagaatt    1080
attaaaaatt atgtgagatc ctcttaattt tataatttt aataaatttt aaccaacaaa    1140
aaaccgtgtt acacctttca taacaatttt gaatgaattt attttaaaag tattggtgtt    1200
aaaattttga ttttagaaga attagataaa taaattaatg tatatttatt atttggaagc    1260
gttttaaaag tgacgtttaa aagagttgat caattttgtt tacagatctg ataatgttg     1320
catgtttatt cttctcaatt gtaaattttc ttttttgtgc acggggattt attttttaatt    1380
tagataagac aaattaagct ttcagaacat caccttgtc caattcattt tagtttctga     1440
tcatggtgta aaatctaact aagttggttt gggcaagaga aatggtccct atgcttaagt    1500
cattctagga cgaaaataaa aatataacag ggtaaagcat atccctgata gcgtgtgtct    1560
attgttttct cattcctcct cggtcacgaa aaccaactaa ttcttttgc cacgattaaa     1620
taattaatct gtgtgttaat tataatgacg agtagggtta tctttcccctt tatcctcagg   1680
agtgtggaaa tgaaaattaa tgaactagct agaaaacgat aatgagaaga acctctcagc    1740
tactatatat ttatgaaatg ttaatttatt ccagacacgt gagtatatat tatacattat    1800
``` ttttaatga atgcaattt tgctttgaag tgcacacaca cggttcattc taattctgat    1860
acctgtatgc tttagaatga ataaggttaa ttaggtaact agctattact gatcataatc    1920
cttgatttaa ggtcaattat agtcttgttc atgtgttcat gaaaagtgca tggtgttaat    1980
aaaatgcagg ttgtgtaaag    2000

<210> SEQ ID NO 16
<211> LENGTH: 651
<212> TYPE: DNA
<213> ORGANISM: Glycine max
<220> FEATURE:
<221> NAME/KEY: mutation
<222> LOCATION: (38)..(38)
<223> OTHER INFORMATION: Sequence can be mutated from C to A.
<220> FEATURE:
<221> NAME/KEY: mutation
<222> LOCATION: (91)..(91)
<223> OTHER INFORMATION: Sequence can be mutated from C to T.
<220> FEATURE:
<221> NAME/KEY: mutation
<222> LOCATION: (103)..(103)
<223> OTHER INFORMATION: Sequence can be mutated from C to T.
<220> FEATURE:
<221> NAME/KEY: mutation
<222> LOCATION: (134)..(134)
<223> OTHER INFORMATION: Sequence can be mutated from C to T.
<220> FEATURE:
<221> NAME/KEY: mutation
<222> LOCATION: (211)..(211)
<223> OTHER INFORMATION: Sequence can be mutated from C to T.
<220> FEATURE:
<221> NAME/KEY: mutation
<222> LOCATION: (245)..(245)
<223> OTHER INFORMATION: Sequence can be mutated from C to T.
<220> FEATURE:
<221> NAME/KEY: mutation
<222> LOCATION: (283)..(283)
<223> OTHER INFORMATION: Sequence can be mutated from G to A.
<220> FEATURE:
<221> NAME/KEY: mutation
<222> LOCATION: (331)..(331)
<223> OTHER INFORMATION: Sequence can be mutated from C to T.
<220> FEATURE:
<221> NAME/KEY: mutation
<222> LOCATION: (346)..(346)
<223> OTHER INFORMATION: Sequence can be mutated from G to A.
<220> FEATURE:
<221> NAME/KEY: mutation
<222> LOCATION: (376)..(376)
<223> OTHER INFORMATION: Sequence can be mutated from C to T.
<220> FEATURE:
<221> NAME/KEY: mutation
<222> LOCATION: (379)..(379)
<223> OTHER INFORMATION: Sequence can be mutated from C to T.
<220> FEATURE:
<221> NAME/KEY: mutation
<222> LOCATION: (410)..(410)
<223> OTHER INFORMATION: Sequence can be mutated from G to T.

<400> SEQUENCE: 16
atgggtgaca ctatgaaacg ggtgccaatt gaaaaacctc catttactct cagccaaatc     60
aagaaggcta ttccaccaca cttttttccag cgttctgttc tgcgctcatt ctcgtatctc    120
atttatgacc ttaccatagc cttctgcctc tattacattg ccaccaatta cttccacaac    180
cttcctcatc ctctcacttt cttggcatgg ccaatctatt gggctgtgca aggattcacc    240
ctagctggtc tttgggtcat tgcacatgac tgtggccacc atgcattcag agatttccaa    300
cttcttgatg ataacgttgg ccttgttctc cactctgctc tattagtccc atactttttca    360 tggaaataca gccatcgccg tcaccactcc aacacaggtt ctcttgagcg agatgaagtg    420

|  |  |
|---|---|
| tttgtaccaa agcagaagtc tagcacacat gtggtgcatc acttgttctc cacaatgcca | 480 |
| cattatcatg caatggacgc tacaaaggca ataaagccca ttttgggaga gtattatcga | 540 |
| tttgacgaga ccccatttgt caaggcaatg tggagagagg caagagagtg tatttatgtg | 600 |
| gaaccagata ctgagaacaa aggtgtattt tggtacaaca ataagttgtg a | 651 |

```
<210> SEQ ID NO 17
<211> LENGTH: 216
<212> TYPE: PRT
<213> ORGANISM: Glycine max
<220> FEATURE:
<221> NAME/KEY: mutagen
<222> LOCATION: (13)..(13)
<223> OTHER INFORMATION: Sequence can be mutated from Pro to His.
<220> FEATURE:
<221> NAME/KEY: mutagen
<222> LOCATION: (31)..(31)
<223> OTHER INFORMATION: Sequence can be mutated from Arg to Cys.
<220> FEATURE:
<221> NAME/KEY: mutagen
<222> LOCATION: (35)..(35)
<223> OTHER INFORMATION: Sequence can be mutated from Arg to Cys.
<220> FEATURE:
<221> NAME/KEY: mutagen
<222> LOCATION: (45)..(45)
<223> OTHER INFORMATION: Sequence can be mutated from Thr to Ile.
<220> FEATURE:
<221> NAME/KEY: mutagen
<222> LOCATION: (71)..(71)
<223> OTHER INFORMATION: Sequence can be mutated from Pro to Ser.
<220> FEATURE:
<221> NAME/KEY: mutagen
<222> LOCATION: (82)..(82)
<223> OTHER INFORMATION: Sequence can be mutated from Ala to Val.
<220> FEATURE:
<221> NAME/KEY: mutagen
<222> LOCATION: (95)..(95)
<223> OTHER INFORMATION: Sequence can be mutated from Ala to Thr.
<220> FEATURE:
<221> NAME/KEY: mutagen
<222> LOCATION: (111)..(111)
<223> OTHER INFORMATION: Sequence can be mutated from His to Tyr.
<220> FEATURE:
<221> NAME/KEY: mutagen
<222> LOCATION: (116)..(116)
<223> OTHER INFORMATION: Sequence can be mutated from Val to Ile.
<220> FEATURE:
<221> NAME/KEY: mutagen
<222> LOCATION: (126)..(126)
<223> OTHER INFORMATION: Sequence can be mutated from Arg to Cys.
<220> FEATURE:
<221> NAME/KEY: mutagen
<222> LOCATION: (127)..(127)
<223> OTHER INFORMATION: Sequence can be mutated from Arg to Cys.
<220> FEATURE:
<221> NAME/KEY: mutagen
<222> LOCATION: (137)..(137)
<223> OTHER INFORMATION: Sequence can be mutated from Arg to Leu.

<400> SEQUENCE: 17

Met Gly Asp Thr Met Lys Arg Val Pro Ile Glu Lys Pro Pro Phe Thr
1               5                   10                  15

Leu Ser Gln Ile Lys Lys Ala Ile Pro Pro His Phe Phe Gln Arg Ser
            20                  25                  30

Val Leu Arg Ser Phe Ser Tyr Leu Ile Tyr Asp Leu Thr Ile Ala Phe
        35                  40                  45

Cys Leu Tyr Tyr Ile Ala Thr Asn Tyr Phe His Asn Leu Pro His Pro
    50                  55                  60

Leu Thr Phe Leu Ala Trp Pro Ile Tyr Trp Ala Val Gln Gly Phe Thr
65                  70                  75                  80
```

```
Leu Ala Gly Leu Trp Val Ile Ala His Asp Cys Gly His His Ala Phe
             85                  90                  95

Arg Asp Phe Gln Leu Leu Asp Asp Asn Val Gly Leu Val Leu His Ser
        100                 105                 110

Ala Leu Leu Val Pro Tyr Phe Ser Trp Lys Tyr Ser His Arg Arg His
        115                 120                 125

His Ser Asn Thr Gly Ser Leu Glu Arg Asp Glu Val Phe Val Pro Lys
    130                 135                 140

Gln Lys Ser Ser Thr His Val Val His His Leu Phe Ser Thr Met Pro
145                 150                 155                 160

His Tyr His Ala Met Asp Ala Thr Lys Ala Ile Lys Pro Ile Leu Gly
                165                 170                 175

Glu Tyr Tyr Arg Phe Asp Glu Thr Pro Phe Val Lys Ala Met Trp Arg
            180                 185                 190

Glu Ala Arg Glu Cys Ile Tyr Val Glu Pro Asp Thr Glu Asn Lys Gly
        195                 200                 205

Val Phe Trp Tyr Asn Asn Lys Leu
    210                 215

<210> SEQ ID NO 18
<211> LENGTH: 2815
<212> TYPE: DNA
<213> ORGANISM: Glycine max

<400> SEQUENCE: 18
acctggctgt ttagcgctat ctgcatattt ccgtgacgca tctctatcgg atctaaggag      60
gaatctcctt tttcctccgt gtcatttgtt gtatttattg ttctgtgcta atacttcaga    120
aaatggctgc attgtgttct tctttgctgt attaagtgtt tgtgttgtga atctggaagc    180
gattttgcgt gacgtaactt gcgtcttcta ctattctctt tcagatctca ttcactgttc    240
ctctttgatg tttttttttg cttactaagc ctatttaatg atattcttta caaatagtta    300
gtggactatt tggttggttg gtgagttatg aatattcgta ttctctacca caagttgggt    360
taaaaaatct ctgcaactcc acgaggatat gttttttatt gtttagagaa aattactctt    420
tcttccttcc ttttcaaatt acacgttttg catcatttgt tttgaaatat atactttatg    480
aatataataa gttatattgt gattattttt aaattgatga atacttatga atgtttgtca    540 atatttttt cttgccatta attaatcttg aacatgttat tgatatctct gatctatatt    600
ttgtcctgat tttagtattt tagaacgaag aataaaattt tatattttt attatcaatt     660 ttgagccatc aaataatttt tcaaaaatta ttttaaccat caaaattaat tttgtcaacc    720
catcctacaa ggcgtttaac ttaatcatta tatttgcttg ggtgaagtga aaaacaagg     780 aagaaaatat taaaaactag cagagaagtt aaagataatt tctcccttat tatttagata    840
aagagaaaat ggaagaaaat aaaataacac tgcctattat ctcatttgtt taaaaaacaa    900
tgaaagcata taactatata aaatacagta ctataactga gccaagaaca tattttgtcg    960
tctgagtaac tttttctttt gcttgttacg ctttctccgc cgatgcagaa ggagtatatg   1020
tttgtgtttt atgttttgaa agattcaatc cccggtttta aagataatac agtatgtttt   1080
atttaaaaga attagtagtt ttttaatat gtttattatt aggcgtgcag actactacaa    1140
ctaaccgcaa taatttttta atattttctt cacaataaaa ttgttttcgt ttttctaac    1200 ggtttacgac acgtaatggg ttttgaactt gagaacgtgc aaataatcta aactccttct   1260
ggttgagtaa cgaagtgaag aaccaattat aatttgtaaa tacttgagta agagttcgtg   1320
```

```
cataaattgg ttttttatcag ttttttccac aaaattatga tttcctgata tttaaaaata   1380
aataaataac tatattccgt aagtcgtaca cagttatatt cagcaaataa attatattta   1440
ataattatta tcttaaaagt tacttaagaa cttggtaaaa atatttttgt ttgaaaaagt   1500
atatgataaa agtttacgat aatgtaactc gtgcttagct gttcctaatt tctgtaacaa   1560
aaaaaaaagt ttcttatttg aaatttgtaa atttccgggt catgttaaga aaatcttgta   1620
gacgaaaagc cggcctattg catgcaccga tcattgatta ctagatacgg aaaacgactc   1680
aattaattta atatgagatg cggaccgatc actagagatg cttcgttcaa catatttgat   1740
attgccaata ttggccatcc ctctcatcat tattgtttat ttatttgtaa catcacatat   1800
tcttgtgggt ccgcttagga ttaggtgttt gttgcaaaaa atacaaaaaa aaatctgtgg   1860
aacaaggatc aacatatatt gtttgtttaa ttgattgatt gattagtttg caagctgtat   1920
tttataattt aatttaattc aacttttgtt ttttagttaa aattgttttt attttactta   1980
ttctgaaaac aaatttattc tacgcagtga atcaaatgac aattttaaac acacaatata   2040
gcataatcga caaatcaatt ttgagtttct ttatcatttt ctttatttat tgacatattt   2100
gcactttctg caaagactct gactcgtggt agatataggg aaggttatag aagttagtgt   2160
agtgtcatat ctagctattt ttgcttattg gaaaaagcct tcccttttgtt tacagatctg   2220 gataaggttg catgcttatt tttctcaact gtgaatggtt atttctttgc attttttgtt   2280
ttgtttttgg ttatgggatt aattttttaa ttacgaagaa gcttttagag catcacccga   2340
atctaattcg ttttggcttt tgtgatcttg atgtaaatct atactaactt ggtttgggca   2400
agagaaattg gtccttgctc aagtccattc taggacgaaa ataaaaatat aacagggtat   2460
agcagatctc tattcgtatg tgggtaacga tagcatgttt ctattgttct cttattcttc   2520
attggtcacg ataacctgct aattatgcca cgattgagat gaaaagtaac gaactagtaa   2580
accatagtga aagaacatt tcgctactat tgttgaaacg tttacaccag gcacttgagt   2640
atgatgcact atatttcaat taatgtaatt tttcgctttg atgagaaaca ttctgattct   2700
gtgagtttag aaactattgc tgataatcct tgatttaaga tttcagtctt gttcatgttc   2760
atttgaagtg ttggtaataa aatgcactga tgtgtcatgt gcagattgtg tgaag        2815
```

<210> SEQ ID NO 19
<211> LENGTH: 1152
<212> TYPE: DNA
<213> ORGANISM: Glycine max
<220> FEATURE:
<221> NAME/KEY: mutation
<222> LOCATION: (277)..(277)
<223> OTHER INFORMATION: Sequence can be mutated from C to T.
<220> FEATURE:
<221> NAME/KEY: mutation
<222> LOCATION: (284)..(284)
<223> OTHER INFORMATION: Sequence can be mutated from G to A.
<220> FEATURE:
<221> NAME/KEY: mutation
<222> LOCATION: (460)..(460)
<223> OTHER INFORMATION: Sequence can be mutated from G to A.
<220> FEATURE:
<221> NAME/KEY: mutation
<222> LOCATION: (466)..(466)
<223> OTHER INFORMATION: Sequence can be mutated from G to A.
<220> FEATURE:
<221> NAME/KEY: mutation
<222> LOCATION: (672)..(672)
<223> OTHER INFORMATION: Sequence can be mutated from A to T.
<220> FEATURE:
<221> NAME/KEY: mutation
<222> LOCATION: (994)..(994)
<223> OTHER INFORMATION: Sequence can be mutated from G to A.

```
<220> FEATURE:
<221> NAME/KEY: mutation
<222> LOCATION: (1049)..(1049)
<223> OTHER INFORMATION: Sequence can be mutated from C to T.
<220> FEATURE:
<221> NAME/KEY: mutation
<222> LOCATION: (1118)..(1118)
<223> OTHER INFORMATION: Sequence can be mutated from G to A.

<400> SEQUENCE: 19
```

| | | | | |
|---|---|---|---|---|
| atggggctg | gtggccgaac | tgctgttcct | cctgccaaca | ggaagtcaga | ggctgaccct | 60 |
| ttgaagcggg | taccatttga | aaaacctcag | tttagtctca | gccagattaa | gaaggccatt | 120 |
| ccacctcact | gtttccagcg | ctctgttctc | cgctcattct | cctatgttgt | ttatgacctc | 180 |
| accatagcct | tctgcctcta | ttatgttgcc | acccattact | tccacctcct | tcccggtcct | 240 |
| ctctctttcg | tggcatggcc | aatctattgg | gctgtccagg | gttgcatcct | tactggtgtt | 300 |
| tgggtcattg | cccatgagtg | tggtcaccat | gcattcagtg | actaccagct | gcttgatgat | 360 |
| attgttggcc | ttatcctcca | ctccgctctc | ctagtcccgt | acttttcatg | gaaatacagc | 420 |
| catcgccgtc | accactccaa | cacaggttct | cttgagcgag | atgaagtatt | tgtgccaaag | 480 |
| cagaagtcca | gtatcatgtg | gtactctaaa | taccttaaca | atccaccagg | cagagtcctc | 540 |
| actcttgccg | tcaccctcac | gcttggttgg | cccttgtact | tggcttttaa | tgtttctgga | 600 |
| aggcctatg | atagatttgc | ttgccactat | gaccctatg | gtcccatta | ctctgaccga | 660 |
| gaacgacttc | aaatatatat | atcagatgca | ggagtacttg | cagtatgcta | tggccttttc | 720 |
| tgtcttgcca | tggcaaaagg | gcttgcctgg | gtggtgtgtg | tttatggagt | tccattgctt | 780 |
| gtggtcaatg | gattttttggt | gttgattaca | tttttgcagc | acactcaccc | tgcattgcca | 840 |
| cactacactt | cctctgagtg | ggactggttg | agaggagctt | tagcaacagt | ggatagagat | 900 |
| tatggaatcc | tgaacaaggt | cttccataat | attacagaca | ctcatgtagc | tcatcacttg | 960 |
| ttctccacaa | tgccacatta | tcatgcaatg | gaggcgacaa | aggcaataaa | gcccatcttg | 1020 |
| ggagagtatt | atcggtttga | tgggactcca | tttgtcaagg | caatgtggag | agaggcaaga | 1080 |
| gagtgtattt | atgtggagcc | agatcaaagt | actcagagca | aggtgtatt | ttggtacaac | 1140 |
| aataagttgt | ga | | | | | 1152 |

```
<210> SEQ ID NO 20
<211> LENGTH: 383
<212> TYPE: PRT
<213> ORGANISM: Glycine max
<220> FEATURE:
<221> NAME/KEY: mutagen
<222> LOCATION: (93)..(93)
<223> OTHER INFORMATION: Sequence can be mutated from Gln to a premature
      stop.
<220> FEATURE:
<221> NAME/KEY: mutagen
<222> LOCATION: (95)..(95)
<223> OTHER INFORMATION: Sequence can be mutated from Cys to Tyr.
<220> FEATURE:
<221> NAME/KEY: mutagen
<222> LOCATION: (154)..(154)
<223> OTHER INFORMATION: Sequence can be mutated from Asp to Asn.
<220> FEATURE:
<221> NAME/KEY: mutagen
<222> LOCATION: (156)..(156)
<223> OTHER INFORMATION: Sequence can be mutated from Val to Ile.
<220> FEATURE:
<221> NAME/KEY: mutagen
<222> LOCATION: (224)..(224)
<223> OTHER INFORMATION: Sequence can be mutated from Gln to His.
<220> FEATURE:
<221> NAME/KEY: mutagen
```

<222> LOCATION: (332)..(332)
<223> OTHER INFORMATION: Sequence can be mutated from Ala to Thr.
<220> FEATURE:
<221> NAME/KEY: mutagen
<222> LOCATION: (350)..(350)
<223> OTHER INFORMATION: Sequence can be mutated from Pro to Leu.
<220> FEATURE:
<221> NAME/KEY: mutagen
<222> LOCATION: (373)..(373)
<223> OTHER INFORMATION: Sequence can be mutated from Ser to Asn.

<400> SEQUENCE: 20

```
Met Gly Ala Gly Gly Arg Thr Ala Val Pro Pro Ala Asn Arg Lys Ser
1               5                   10                  15

Glu Ala Asp Pro Leu Lys Arg Val Pro Phe Glu Lys Pro Gln Phe Ser
            20                  25                  30

Leu Ser Gln Ile Lys Lys Ala Ile Pro Pro His Cys Phe Gln Arg Ser
        35                  40                  45

Val Leu Arg Ser Phe Ser Tyr Val Val Tyr Asp Leu Thr Ile Ala Phe
    50                  55                  60

Cys Leu Tyr Tyr Val Ala Thr His Tyr Phe His Leu Leu Pro Gly Pro
65                  70                  75                  80

Leu Ser Phe Val Ala Trp Pro Ile Tyr Trp Ala Val Gln Gly Cys Ile
                85                  90                  95

Leu Thr Gly Val Trp Val Ile Ala His Glu Cys Gly His His Ala Phe
            100                 105                 110

Ser Asp Tyr Gln Leu Leu Asp Asp Ile Val Gly Leu Ile Leu His Ser
        115                 120                 125

Ala Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Gln Lys Ser Ser Ile Met Trp Tyr Ser Lys Tyr Leu Asn Asn Pro Pro
                165                 170                 175

Gly Arg Val Leu Thr Leu Ala Val Thr Leu Thr Leu Gly Trp Pro Leu
            180                 185                 190

Tyr Leu Ala Phe Asn Val Ser Gly Arg Pro Tyr Asp Arg Phe Ala Cys
        195                 200                 205

His Tyr Asp Pro Tyr Gly Pro Ile Tyr Ser Asp Arg Glu Arg Leu Gln
    210                 215                 220

Ile Tyr Ile Ser Asp Ala Gly Val Leu Ala Val Cys Tyr Gly Leu Phe
225                 230                 235                 240

Cys Leu Ala Met Ala Lys Gly Leu Ala Trp Val Cys Val Tyr Gly
                245                 250                 255

Val Pro Leu Leu Val Val Asn Gly Phe Leu Val Leu Ile Thr Phe Leu
            260                 265                 270

Gln His Thr His Pro Ala Leu Pro His Tyr Thr Ser Ser Glu Trp Asp
        275                 280                 285

Trp Leu Arg Gly Ala Leu Ala Thr Val Asp Arg Asp Tyr Gly Ile Leu
    290                 295                 300

Asn Lys Val Phe His Asn Ile Thr Asp Thr His Val Ala His His Leu
305                 310                 315                 320

Phe Ser Thr Met Pro His Tyr His Ala Met Glu Ala Thr Lys Ala Ile
                325                 330                 335

Lys Pro Ile Leu Gly Glu Tyr Tyr Arg Phe Asp Gly Thr Pro Phe Val
            340                 345                 350
```

| | | |
|---|---|---|
| Lys Ala Met Trp Arg Glu Ala Arg Glu Cys Ile Tyr Val Glu Pro Asp | | |
| 355 | 360 | 365 |

| | | |
|---|---|---|
| Gln Ser Thr Gln Ser Lys Gly Val Phe Trp Tyr Asn Asn Lys Leu | | |
| 370 | 375 | 380 |

<210> SEQ ID NO 21
<211> LENGTH: 4816
<212> TYPE: DNA
<213> ORGANISM: Glycine max

<400> SEQUENCE: 21

| | | | | | |
|---|---|---|---|---|---|
| atttgccaaa | caacgtgtca | aaatataccc | cgtgggtccc | acctcaattg | gacggaaggc | 60 |
| gcactagtgc | cactgctaat | cgctcgcttt | taaataccgc | ctctctgcgt | tcccctaatc | 120 |
| tttgcccccc | tctctctcac | cctcctcttc | acacattttc | tgtgcgctct | aacaaacatt | 180 |
| ctcgttcaca | ctttcaggta | cttttctctc | cttatctctt | tatctttatt | ctttcctact | 240 |
| ttattgctta | aaccaatgct | atctatgctt | caatctcgcc | ttcttatttt | ccacttccct | 300 |
| tttctcgctt | gatctaaccg | ttttcgccct | ccgcgcttcg | attgactgag | tacatctacg | 360 |
| attctctgtt | ctttcatttc | atagatttcg | tctgattttg | gctaacttgg | tttctgttgc | 420 |
| ggccgattct | tacatatact | gattgtttag | cataaatgaa | cttgcttgtt | tagcactatc | 480 |
| tgcatatttt | cgtcacgcat | ctctttcgga | tctaaggatg | aatctcctat | ttcctccgta | 540 |
| ttatttctcg | tatctcttgt | tctgtgctaa | tgctccagaa | aatggcagca | ttgtcttctt | 600 |
| ctttgctgtt | ataagtgttt | gtgttgtgaa | tctggaagcg | attttgcgtg | aggtaacttg | 660 |
| cgacttcaac | tattatcttt | cagatctcgt | taatttatta | gctgctatta | atttgtgtgt | 720 |
| gcagtgtcaa | actgaagcac | acgactgctt | agaagttaga | atttgactga | ctgttcctct | 780 |
| ttgattttt | tctttctttt | ctttgcttac | tcggcctatt | taatgatctt | tataaataga | 840 |
| ttagtggacc | acttggttag | ttggtgagtt | atgaatattc | gaattttcta | ccacaagttg | 900 |
| ggttaaaaaa | atctctgcaa | ctacacgagg | atttttatt | ttatttagag | gaaactattc | 960 |
| tgtcatcctt | tttccgatta | cacttttcta | tcagttgttt | tgaaatatac | accttaggaa | 1020 |
| tataatatta | cccctttcgg | tcttaatata | aatatatttt | aattatttat | atttatttta | 1080 |
| atgaaattat | ttttaaaata | ctttcattta | atagaatttt | taataaagtt | aaagactttt | 1140 |
| attgtgtaga | gttaacgaa | gttaattagt | tttcttagta | aatgtaaaat | atgccttttt | 1200 |
| tgttgtttat | aatggagatt | ggaaaaaata | tactttaatt | ttttcaagt | gatgaataat | 1260 |
| tatggatgtt | ttgtcaatat | ttttgtcttg | ctatacaact | ttcagtcttg | ccattaaata | 1320 |
| attttgaatg | tgttattgat | atctctgaac | aatatttaga | gaacgaacaa | taaaatttta | 1380 |
| tatatttta | ttataattc | tttttattac | ctttttatta | tcaatttga | aatttggttt | 1440 |
| aatatctgtg | tttcattttt | gaggtctcaa | atttgatata | aggaggttca | aaatgcgttg | 1500 |
| ctagccattt | taaagattag | caggagagga | aatgtttctg | gacttaaatt | taaaatatgc | 1560 |
| ttatttgttt | ttcaagagag | agagatcaat | atttatataa | tacacttgaa | ttaatataca | 1620 |
| ccattgttgc | aaaaaaaaaa | aaatattagt | tgattgtgtg | acaatatttt | atattaaata | 1680 |
| taattagtta | atttagttca | agttgagtta | catttttaca | taccattctt | agccgccact | 1740 |
| ttttatatt | tatttgtagg | aataacttt | catctgtatc | aatttccccc | gtctaataaa | 1800 |
| aagggtttga | cttttctta | taatagagtt | ttttttttt | tgctttaagt | tattgtaaaa | 1860 |
| taattatttt | atttttttg | cctttgtaaa | ttatgtatat | ttaatgtttt | aataggaaaa | 1920 |
| aaatgttatc | aaaagcacta | aaagactaaa | attaaacaac | cataatttgc | aaagatgaaa | 1980 |

```
ataaaaaaat aattttgtaa agataaaaaa tgaaataaaa tagttaaatt ataggaattt    2040
aaaagctatt taaatcaaca aaagttaaag tttctgtaaa aaaaaagttc aattttttt     2100 ttattattga aaaagttaaa gctaatgagc gttcgatttg ggttagtatg tagtatttat    2160
tattttcaag attttggatt ttattgtcga tgtttctgat ttgaatataa ttattttcca    2220
ttcaacttgt gattttataa gaaaaaaaaa ggtacagaaa aaatcaagcg cttttttat     2280 ttcaattagt ggaggtttca ctgaaatggg taaagaatct attttgcaat cacaattatt    2340
accggtattc aactgcaaca aggaacaaaa ttcctttcgt aaatatacgg agaggaatct    2400
attttgactt gttgaattta tggtaaagta gaatttagaa tttaattatg agttgaagta    2460
attttgaata atttatatgt taaatataaa attttgtact aagttttatt cataactttg    2520
attctataat acaaacatac ataagttcaa aaataatttt aattaaaatt aattttatca    2580 attttattc aaacacgagt ctaatttgct tgatgaatta agaaaataag gaagaaaata     2640
ttaaaaacta ggagagaagt taaagagaat ttcatctta ttattctcag ttgtttcaaa     2700
aataatgaaa ggatagctat ataatactgt aactgagcca agaacatatt tgccgtccga    2760 gtaaccttt ctttcttgt tccgttttct ccgccgatga agagagggaa gggaatgtat      2820
ctttgtattt atgttttcaa agagttcgtg cataaaattg gtttaatcaa attttcata     2880 agattattat tttatgattt tttaaaataa attagtaact atattccgta agtcgtacac    2940
agttatatgt agtaagtaaa ttatatttta ataattatta tcttaaaatt ttcttaagaa    3000
cttggttaaa atattttgt ttgaaaaagt ttatgataac ttttttttgt tgaaaaaaag    3060
tttacgatta tctaactcgt acttagatta tttctaattg ggatttattg aagggttttt    3120
taagtaaaga aattgtttct tatggtttct ttttattgg acaaatttac gtagcaaaga    3180
gtgtttctta aaaacaagac atgtatcctt tgaaaaaaaa actatttctt tgaaataaaa   3240
aataatattt atctggcaca taataatgtt aaaattaaat cataattagg taaaaataaa    3300
ataaatataa aagtatgagt ttgttaagtt ttttataatt ttttattatt aaagtaaaat    3360
tatgtatgat tttttttataa tgatatgata ttttagggat cacaaaaaat aatgtggtga   3420
atacaaaagt aactcaaaaa attcatttag taaattttca ttggagatgc tattattatg    3480
ctttctgatt gctttgtcca aaaaataaag aatgtttttt tatttgaaaa ttgaaaattt    3540
ctgggtcatg ttaagatctt gtagacggta acgtcggcct aaagttgtgt gaggggtgtt    3600
gcatgcaccg atcattaatt actcgatatg gaaaacgact gaaataattt aatttgatgt    3660
tgctaatatt ggccatccct ctcatcatta ttgttttttt atttgtaaca tgacatattc    3720
ttgtgggtcc gctacggatt gggtgtttgt tgccaaaaaa tacaaaatat ctgtggaaca    3780
aggataaaca gtcttgtttg tttaattgat tgattgatga gtttgcaagc tatatttta    3840 atttatttta attaaacttt tgtgttttag ttctacaatt ttattcatct tgattttttt    3900
tttacttggc aaaatcatga tttttttaatt tttacttatg ttgaaaacaa atttattgct    3960
aaaaaaacat ttattctttt tttagaggaa aaacaaattt gtgatatgta gtgaatcaaa    4020
tgaaaatttt aaacataata tagaatactc tacaaatcaa ttttgagttt ctttatcatt    4080
ttatttattt attgacatac ttctactttc tgcaaagacc ctgactcgtg ggagatatag    4140
ggaaggttat ggaagttagt gtattgtcat atctagctat ctttgctaat tgaaaaagcc    4200 ttcccttgt ttacagatct ggataaggtt gcatgtttat tcttttcaac tgtgaatggt     4260
tctttgcatc ttttttagta tatgagatta atgttttaat taggaagaag cttttagaac    4320
```

-continued

```
atcacccgaa tccaattcgt tttggtttct gtgatcttga tgtaaatcta tactaatttg    4380
gtttgggcag gagaaaatgt tctttgctca agtcctctag gacgaaaata taaatataac    4440
agggtatatc agatctctat tcttctgtgg gtaatgatag catgtttctg ttgttttctt    4500
attcttcatt ggtcatgata acctgctaat tctatttgcc acgattgaga tgaaaaggta    4560
atgaactagt aaacaataat gagaagaata tgtcgctact attgttgaaa cggttacgcc    4620
aggcacttga gtatgatgca ctattttaat taatgcattt ttttttgctt tgatgagaac    4680
gcacattgtt cattctgatt cggtgagttt agaaactatt gctgataatc cttgatttaa    4740
gattttagtc ttgttcatgt tcattaaaag tgttgtaaaa aaatgcactg atatgtcatg    4800
tgcagattgt gtgaag                                                    4816
```

<210> SEQ ID NO 22
<211> LENGTH: 1152
<212> TYPE: DNA
<213> ORGANISM: Glycine max
<220> FEATURE:
<221> NAME/KEY: mutation
<222> LOCATION: (49)..(49)
<223> OTHER INFORMATION: Sequence can be mutated from G to A.
<220> FEATURE:
<221> NAME/KEY: mutation
<222> LOCATION: (88)..(88)
<223> OTHER INFORMATION: Sequence can be mutated from C to T.
<220> FEATURE:
<221> NAME/KEY: mutation
<222> LOCATION: (175)..(175)
<223> OTHER INFORMATION: Sequence can be mutated from G to A.
<220> FEATURE:
<221> NAME/KEY: mutation
<222> LOCATION: (259)..(259)
<223> OTHER INFORMATION: Sequence can be mutated from C to T.
<220> FEATURE:
<221> NAME/KEY: mutation
<222> LOCATION: (313)..(313)
<223> OTHER INFORMATION: Sequence can be mutated from C to A.
<220> FEATURE:
<221> NAME/KEY: mutation
<222> LOCATION: (625)..(625)
<223> OTHER INFORMATION: Sequence can be mutated from C to T.
<220> FEATURE:
<221> NAME/KEY: mutation
<222> LOCATION: (672)..(672)
<223> OTHER INFORMATION: Sequence can be mutated from A to T.
<220> FEATURE:
<221> NAME/KEY: mutation
<222> LOCATION: (781)..(781)
<223> OTHER INFORMATION: Sequence can be mutated from G to A.
<220> FEATURE:
<221> NAME/KEY: mutation
<222> LOCATION: (799)..(799)
<223> OTHER INFORMATION: Sequence can be mutated from G to A.
<220> FEATURE:
<221> NAME/KEY: mutation
<222> LOCATION: (1114)..(1114)
<223> OTHER INFORMATION: Sequence can be mutated from G to A.

<400> SEQUENCE: 22

```
atgggggcgg gtggccgaac tgatgttcct cctgccaaca ggaagtcaga ggttgaccct      60
ttgaagcggg tgccatttga aaaacctcca tttagtctca gccaaatcaa gaaggtcatt     120
ccacctcact gttccagcg ttctgttttc cgctcattct cctatgttgt ttacgacctc     180
accatagcct tctgcctcta ttatgttgcc acccattact tccacctcct tcccagccct     240
ctctctttct ggcatggcc aatctactgg gctgtccaag gttgcatcct tactggagtt     300
tgggtcattg cccatgagtg tggccaccat gcattcagtg actaccagtt gcttgatgat     360
attgttggcc ttgtcctcca ctccggtctc ctagtcccat acttttcatg gaaatacagc     420
```

```
catcgccgtc accactccaa cactggttct cttgagcggg atgaagtatt tgtgccaaag    480
cagaagtcct gtatcaagtg gtactctaaa taccttaaca atcctccagg cagagtcctc    540
actcttgctg tcaccctcac acttggttgg cccttgtact tggctttaaa tgtttctgga    600 aggcctatg atagatttgc ttgccactat gacccatatg gtcccattta ctctgatcgt     660
gaacgacttc aaatatatat atcagatgca ggagtacttg cagtatgcta tggccttttc    720
cgtcttgcca tggcaaaagg acttgcctgg gtggtgtgtg tttatggagt tccattgcta    780
gtggtcaatg gattttggt gttgattaca ttcttgcagc atactcaccc tgcattgcca     840
cattacactt cctctgagtg ggactggttg agaggagctt tagcaacagt ggatagagat    900
tatggaatcc tgaacaaggt cttccataat attacagaca ctcatgtagc acatcacttg    960
ttctccacaa tgccacatta tcatgcaatg gaggctacaa aggcaataaa acccatttg    1020 ggagagtatt atcggtttga tgagactcca tttgtcaagg caatgtggag agaggcaaga   1080
gagtgtattt atgtggagcc agatcaaagt accgagagca aggtgtattt ttggtacaac   1140
aataagttgt ga                                                      1152
```

```
<210> SEQ ID NO 23
<211> LENGTH: 383
<212> TYPE: PRT
<213> ORGANISM: Glycine max
<220> FEATURE:
<221> NAME/KEY: mutagen
<222> LOCATION: (17)..(17)
<223> OTHER INFORMATION: Sequence can be mutated from Glu to Lys.
<220> FEATURE:
<221> NAME/KEY: mutagen
<222> LOCATION: (30)..(30)
<223> OTHER INFORMATION: Sequence can be mutated from Pro to Ser.
<220> FEATURE:
<221> NAME/KEY: mutagen
<222> LOCATION: (59)..(59)
<223> OTHER INFORMATION: Sequence can be mutated from Asp to Asn.
<220> FEATURE:
<221> NAME/KEY: mutagen
<222> LOCATION: (87)..(87)
<223> OTHER INFORMATION: Sequence can be mutated from Pro to Ser.
<220> FEATURE:
<221> NAME/KEY: mutagen
<222> LOCATION: (105)..(105)
<223> OTHER INFORMATION: Sequence can be mutated from His to Asn.
<220> FEATURE:
<221> NAME/KEY: mutagen
<222> LOCATION: (209)..(209)
<223> OTHER INFORMATION: Sequence can be mutated from His to Tyr.
<220> FEATURE:
<221> NAME/KEY: mutagen
<222> LOCATION: (224)..(224)
<223> OTHER INFORMATION: Sequence can be mutated from Gln to His.
<220> FEATURE:
<221> NAME/KEY: mutagen
<222> LOCATION: (261)..(261)
<223> OTHER INFORMATION: Sequence can be mutated from Val to Met.
<220> FEATURE:
<221> NAME/KEY: mutagen
<222> LOCATION: (267)..(267)
<223> OTHER INFORMATION: Sequence can be mutated from Val to Met.
<220> FEATURE:
<221> NAME/KEY: mutagen
<222> LOCATION: (372)..(372)
<223> OTHER INFORMATION: Sequence can be mutated from Glu to Lys.

<400> SEQUENCE: 23

Met Gly Ala Gly Gly Arg Thr Asp Val Pro Pro Ala Asn Arg Lys Ser
1               5                   10                  15

Glu Val Asp Pro Leu Lys Arg Val Pro Phe Glu Lys Pro Pro Phe Ser
```

20                  25                  30
Leu Ser Gln Ile Lys Val Ile Pro Pro His Cys Phe Gln Arg Ser
         35                  40                  45

Val Phe Arg Ser Phe Ser Tyr Val Tyr Asp Leu Thr Ile Ala Phe
 50                  55                  60

Cys Leu Tyr Tyr Val Ala Thr His Tyr Phe His Leu Leu Pro Ser Pro
 65                  70                  75                  80

Leu Ser Phe Leu Ala Trp Pro Ile Tyr Trp Ala Val Gln Gly Cys Ile
                 85                  90                  95

Leu Thr Gly Val Trp Val Ile Ala His Glu Cys Gly His His Ala Phe
                100                 105                 110

Ser Asp Tyr Gln Leu Leu Asp Asp Ile Val Gly Leu Val Leu His Ser
                115                 120                 125

Gly Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Gln Lys Ser Cys Ile Lys Trp Tyr Ser Lys Tyr Leu Asn Asn Pro Pro
                165                 170                 175

Gly Arg Val Leu Thr Leu Ala Val Thr Leu Thr Leu Gly Trp Pro Leu
                180                 185                 190

Tyr Leu Ala Leu Asn Val Ser Gly Arg Pro Tyr Asp Arg Phe Ala Cys
                195                 200                 205

His Tyr Asp Pro Tyr Gly Pro Ile Tyr Ser Asp Arg Glu Arg Leu Gln
                210                 215                 220

Ile Tyr Ile Ser Asp Ala Gly Val Leu Ala Val Cys Tyr Gly Leu Phe
225                 230                 235                 240

Arg Leu Ala Met Ala Lys Gly Leu Ala Trp Val Val Cys Val Tyr Gly
                245                 250                 255

Val Pro Leu Leu Val Val Asn Gly Phe Leu Val Leu Ile Thr Phe Leu
                260                 265                 270

Gln His Thr His Pro Ala Leu Pro His Tyr Thr Ser Ser Glu Trp Asp
                275                 280                 285

Trp Leu Arg Gly Ala Leu Ala Thr Val Asp Arg Asp Tyr Gly Ile Leu
    290                 295                 300

Asn Lys Val Phe His Asn Ile Thr Asp Thr His Val Ala His His Leu
305                 310                 315                 320

Phe Ser Thr Met Pro His Tyr His Ala Met Glu Ala Thr Lys Ala Ile
                325                 330                 335

Lys Pro Ile Leu Gly Glu Tyr Tyr Arg Phe Asp Glu Thr Pro Phe Val
                340                 345                 350

Lys Ala Met Trp Arg Glu Ala Arg Glu Cys Ile Tyr Val Glu Pro Asp
                355                 360                 365

Gln Ser Thr Glu Ser Lys Gly Val Phe Trp Tyr Asn Asn Lys Leu
                370                 375                 380

<210> SEQ ID NO 24
<211> LENGTH: 3422
<212> TYPE: DNA
<213> ORGANISM: Glycine max

<400> SEQUENCE: 24
aaaggctgcg agaaaataac aggaacgaac gatgatatta tcggcaaaga aagagagaaa      60
aatgtcctca tcagcaaaaa taataataat aataataata aataaagaa tatgatgggt     120

```
aacccttcac tcgagggaaa ccttcatttc gtggagagaa gtaatatagc ataaatactc      180
tttatcttcc ctcatctcct tacaaattct tcgtctgcat cttctctcct tcagatacag      240
agggagaaag atacaaaacc ttttcactcg tccttcttct tcaggttttt accctaact       300 tatgcttcat ttcttttctt ttttcttttt attttattt gccttctatg tttcttcttt       360
tatatatgtt tttgtttgtt gtgattaatg cttatatatt gccaatagat ataatcacga      420
ggtttaattt ccagctgagt cttattttca cgattgcatc tttgctagat ctaaatcatc      480
taataattgc ccctttttct gtcgttcatg taccttctag atgtttaacg ttgatttacc      540
ttcttggtgc ttgtttaaa gtttatttgg ttcaatgtgg ttttactctg aaatcgaatt       600
gtgactacaa ctatagttac gtgcatcaac catatttat tcaaagacgg agtgcatcat       660
acatgttctt tttgttaacg tttagaactt ttcttggatc caaggatgaa catctttttc      720
tgcttttcat gattaatttt tcgtatttgt tgttatgtaa tggggatctc gtgacagtgt      780
tacgctttct cgtgagttca atttcatctt atagctacca atgaatacga tcatcgtatg      840
acgtcgtagg gttttaagc cgataaaaaa aacgttaggg ttttaatttt taaaatatta       900
ttaatattat ttttgttaa attaatatat attttatctt ttattccaat ttttcctata      960
tttgacttaa tatttaattt tttatactgc ataattttct aaagaaacaa gagttcaagg     1020
ttaacaaatt ctttctctaa ttgataaaag tctgttcata ataataaatt tacctttgct     1080
ttatttcttg tgcttttcaa tttcttagtg gaagatcttt ttttttttaa tggataaaat     1140
gatcatttgt ggttaattat ttatttgata tgggtggctc ttattgcacg gctgctatgc     1200
aaggattcat ttcaacagca aaaagagcaa ttataaaatt aagagaagag ttaacagttc     1260
tttaatgtag taattttatt aatatatttt ttagttaaaa tttatgttgt gagttttatt     1320
aatttgaaga tgaaatgggg aaggaaactc acatatttca tgaaactcac gtaatttgca     1380
taagaaaagt gtatttgaat tttttaaaac atgttgctaa cttttctcat taaaaaatat     1440
gatttccaag ctgcccacac catgcataat ttccatgtga ttatactttg tcaaattatt     1500
ttaatgcgca tttaattatc tatgttgtaa acttcgttga aatggacttg caagtaattc     1560
cctagatagt agttttaatt ttccacggct ccattttgtt cacaattgag tgtagactgt     1620
agttgtattc tattgttttg tttgttaggt ttgcactgtg caagctactt aactatttgt     1680
ttatgttgac tgattaccat cttccgcata catttgacac gttcatagaa tagacatatt     1740
cttgtagaca aaattaatt atcttttcaa actccaccaa atcttatatt ggaacggaat      1800
gtgaaaggat tgtaaaacgt gcgtcgtaaa aattagaatc cgaaaagtat gtgttagcat     1860
accaaactct tatattgatt ctttaaaaga aaataaaaga gtgggtccaa aattgcgaat     1920
acgtgttctt ttattaaaat atgattttaa gaatgacgca tctttattgt caactacagt     1980
gtatgataac gcttttttgc ctatatatag gccatttga attttatacg attctacaat      2040
agaaaagttt ttaatttaca tacgctttag tgcttgtgta actgaacaaa ctagccttat     2100
actatacatg cgctgatatt tacgtaatta ctatggtaat tgttggagat ggaggaatat     2160
taatctttga cttattggag ttggcctact ggtggagtta aagtacgta gatgtatgag       2220 gactcaactc agcaaaaaca aatgtatgag gacttgatat aattattgct gtcgttacaa     2280 aaaaaatta agagaaatgt taagaataca aatacaattt ctaacacatt attttatgag     2340
tttcacatgg tattcaaatg actacatatg tcaattttaa ctccagagat tattaactaa     2400
gataactaat ttttcttatg tttgacaaca ccacataagg aaccacatca tatagtactc     2460
```

| | |
|---|---|
| atattagtac tataaagcac tcatgaattc attttctttt ttatcatgaa tatcatacac | 2520 |
| ttaaagatat gcaagatttc aattttcatc ttcgacaagc caacattaga tttgaagtta | 2580 |
| gcgtcgattt agatgctaac tacaacaata aaaaaattaa gaaaaacatg ttattagctt | 2640 |
| acatgacaat gatgtaataa tgataatgtg atattctatc tgtcacgtca tcgtttaata | 2700 |
| gataaatatt aacgataggt gccaaagcaa aaaaaactga aacatgaga tagaaaaatc | 2760 |
| aaattttttt ataagtaaca atctaaaaaa gagatatatc ttaggtaaga aaacatatt | 2820 |
| taagtctttt taatatattt taactgatta aagagtgagt atttaaagta gtacattaaa | 2880 |
| gattccgctc ctgcctaatt agacataacc tatttcatgt tagttttttga agttactgct | 2940 |
| cattctataa ggtcacctat tattacttgc gtgcatggaa tgctagagac attttttta | 3000 |
| tattctctaa cactcttgga ttgactactc ttggattgac taaaaattta ttgaaaattg | 3060 |
| tcaattttgg tgggtcttaa ttctaaatta agagagaatc attatataaa aagtgaaatt | 3120 |
| tattaaaatt tattatttta ataaatttta ttcaatcata gacataatat aatattagaa | 3180 |
| agagtttccc tagtacttct ccattaccta tgtttaatca gataaattat atttgagatg | 3240 |
| ttcatgagga tgttaaaaaa tcatattcac tagctgtgat agtgatgtgg tcaaaataat | 3300 |
| taatataaat agaagataag atcttatttg atgagttagt tttgcaatta agtcacatca | 3360 |
| taatccaaat tccaatacta atcaacaaac ttttctattc atgttttagg ttgcgcgata | 3420 |
| aa | 3422 |

```
<210> SEQ ID NO 25
<211> LENGTH: 1368
<212> TYPE: DNA
<213> ORGANISM: Glycine max
<220> FEATURE:
<221> NAME/KEY: mutation
<222> LOCATION: (439)..(439)
<223> OTHER INFORMATION: Sequence can be mutated from C to T.
<220> FEATURE:
<221> NAME/KEY: mutation
<222> LOCATION: (510)..(510)
<223> OTHER INFORMATION: Sequence can be mutated from G to A.
<220> FEATURE:
<221> NAME/KEY: mutation
<222> LOCATION: (579)..(579)
<223> OTHER INFORMATION: Sequence can be mutated from G to A.
<220> FEATURE:
<221> NAME/KEY: mutation
<222> LOCATION: (622)..(622)
<223> OTHER INFORMATION: Sequence can be mutated from A to T.
<220> FEATURE:
<221> NAME/KEY: mutation
<222> LOCATION: (643)..(643)
<223> OTHER INFORMATION: Sequence can be mutated from C to T.
<220> FEATURE:
<221> NAME/KEY: mutation
<222> LOCATION: (751)..(751)
<223> OTHER INFORMATION: Sequence can be mutated from C to T.
<220> FEATURE:
<221> NAME/KEY: mutation
<222> LOCATION: (905)..(905)
<223> OTHER INFORMATION: Sequence can be mutated from G to A.
<220> FEATURE:
<221> NAME/KEY: mutation
<222> LOCATION: (1020)..(1020)
<223> OTHER INFORMATION: Sequence can be mutated from A to T.
<220> FEATURE:
<221> NAME/KEY: mutation
<222> LOCATION: (1094)..(1094)
<223> OTHER INFORMATION: Sequence can be mutated from G to T.

<400> SEQUENCE: 25
```

| | |
|---|---|
| atgggaggtg gtggtcgaag ctcagctact ctcaagcatc aaaactcaat tgaaaaccat | 60 |

```
tcaaagaaga agcgtgtccc acatgcaaag ccacccttca ctctaagcca actgaagaag      120
gcaatttcac cacattgctt ccaccgttca acattccgtt cattctccta cgtcctctat      180
gacctaacca tagcctcatg cctcttctat gccgcagtaa attacatccc tacccttccc      240
catgaaaacc tctccctcct agcatggcct ctctattggt tcatccaagg ttccatccta      300
accggggttt gggtcatcgc acacgaatgc ggccaccacg cctttagcga tcaccaatgg      360
ctcgatgacc ttgttggcct aatcctccac tcacttctcc tagtgcccta ttttcatgg       420 aaatatagcc accgccgcca ccactcgaac acaggatcac tcgaacgtga tgaagtgttt      480
gtgccaaaaa caaagtctag tatgggttgg tattctaaat accttaacaa ctcgccaggg      540
agggttctca cacttgctat aaccctaacc ctaggttggc ctctttattt agctttcaat      600
gtttcgggta ggtcttatga gagatttgca tgtcactatg acccttatgg ccccatttac      660
tcaaaccgtg aaaggcttca gatttatgta tccgatgctg ggattcttgc ggtgtgtttt      720
ggtctctaca aggctgtctt ggcaaaaggg cttgtttggg ttgtttgtgt ttatggggtg      780
cctttgttgg tggttaatgg gttcttggtg ttgatcactt tcttgcaaca cactcaccct      840
gcggttcctc actatgattc ctccgagtgg gattggttga gaggtgcttt ggccactgtg      900
gatagagatt atgggatttt gaataaggtt ttgcataaca tcactgacac acacgtggca      960
catcacttgt tttccacaat gccgcattat catgcaatgg aggctactaa ggctataaaa     1020
ccaattttgg gagagtatta tcactttgat gagactccta tttataaggc aatgtggaga     1080
gaggcaaagg agtgcatgta tgttgagcct gataaagggt ctaatgggaa aggtgtttat     1140
tggtacaata ataagttgta aacattagag ctattgagta ttggttgaga ctcgagagtt     1200
tagagtttag gttgttatg tacgaatctc taatgttcct tatgggtctt ataaataat       1260 ttcataatca gtggtagaaa aggagaatgt aatgagtgta tgcctatgtt gttatgcata     1320
tggtgggttg aaatcagttt atggctttca cttaatggtt gggaagct                  1368
```

<210> SEQ ID NO 26
<211> LENGTH: 386
<212> TYPE: PRT
<213> ORGANISM: Glycine max
<220> FEATURE:
<221> NAME/KEY: mutagen
<222> LOCATION: (147)..(147)
<223> OTHER INFORMATION: Sequence can be mutated from His to Tyr.
<220> FEATURE:
<221> NAME/KEY: mutagen
<222> LOCATION: (170)..(170)
<223> OTHER INFORMATION: Sequence can be mutated from Trp to a premature stop.
<220> FEATURE:
<221> NAME/KEY: mutagen
<222> LOCATION: (193)..(193)
<223> OTHER INFORMATION: Sequence can be mutated from Trp to a premature stop.
<220> FEATURE:
<221> NAME/KEY: mutagen
<222> LOCATION: (208)..(208)
<223> OTHER INFORMATION: Sequence can be mutated from Arg to a premature stop.
<220> FEATURE:
<221> NAME/KEY: mutagen
<222> LOCATION: (215)..(215)
<223> OTHER INFORMATION: Sequence can be mutated from Pro to Ser.
<220> FEATURE:
<221> NAME/KEY: mutagen
<222> LOCATION: (251)..(251)
<223> OTHER INFORMATION: Sequence can be mutated from Leu to Phe.
<220> FEATURE:
<221> NAME/KEY: mutagen

```
<222> LOCATION: (302)..(302)
<223> OTHER INFORMATION: Sequence can be mutated from Arg to Lys.
<220> FEATURE:
<221> NAME/KEY: mutagen
<222> LOCATION: (340)..(340)
<223> OTHER INFORMATION: Sequence can be mutated from Lys to Asn.
<220> FEATURE:
<221> NAME/KEY: mutagen
<222> LOCATION: (365)..(365)
<223> OTHER INFORMATION: Sequence can be mutated from Cys to Phe.

<400> SEQUENCE: 26
```

Met Gly Gly Gly Gly Arg Ser Ser Ala Thr Leu Lys His Gln Asn Ser
1               5                   10                  15

Ile Glu Asn His Ser Lys Lys Arg Val Pro His Ala Lys Pro Pro
            20                  25                  30

Phe Thr Leu Ser Gln Leu Lys Lys Ala Ile Ser Pro His Cys Phe His
            35                  40                  45

Arg Ser Thr Phe Arg Ser Phe Ser Tyr Val Leu Tyr Asp Leu Thr Ile
        50                  55                  60

Ala Ser Cys Leu Phe Tyr Ala Ala Val Asn Tyr Ile Pro Thr Leu Pro
65                  70                  75                  80

His Glu Asn Leu Ser Leu Leu Ala Trp Pro Leu Tyr Trp Phe Ile Gln
                85                  90                  95

Gly Ser Ile Leu Thr Gly Val Trp Val Ile Ala His Glu Cys Gly His
            100                 105                 110

His Ala Phe Ser Asp His Gln Trp Leu Asp Asp Leu Val Gly Leu Ile
        115                 120                 125

Leu His Ser Leu Leu Leu Val Pro Tyr Phe Ser Trp Lys Tyr Ser His
130                 135                 140

Arg Arg His His Ser Asn Thr Gly Ser Leu Glu Arg Asp Glu Val Phe
145                 150                 155                 160

Val Pro Lys Thr Lys Ser Ser Met Gly Trp Tyr Ser Lys Tyr Leu Asn
                165                 170                 175

Asn Ser Pro Gly Arg Val Leu Thr Leu Ala Ile Thr Leu Thr Leu Gly
            180                 185                 190

Trp Pro Leu Tyr Leu Ala Phe Asn Val Ser Gly Arg Ser Tyr Glu Arg
        195                 200                 205

Phe Ala Cys His Tyr Asp Pro Tyr Gly Pro Ile Tyr Ser Asn Arg Glu
210                 215                 220

Arg Leu Gln Ile Tyr Val Ser Asp Ala Gly Ile Leu Ala Val Cys Phe
225                 230                 235                 240

Gly Leu Tyr Lys Ala Val Leu Ala Lys Gly Leu Val Trp Val Val Cys
                245                 250                 255

Val Tyr Gly Val Pro Leu Leu Val Asn Gly Phe Leu Val Leu Ile
            260                 265                 270

Thr Phe Leu Gln His Thr His Pro Ala Val Pro His Tyr Asp Ser Ser
        275                 280                 285

Glu Trp Asp Trp Leu Arg Gly Ala Leu Ala Thr Val Asp Arg Asp Tyr
290                 295                 300

Gly Ile Leu Asn Lys Val Leu His Asn Ile Thr Asp Thr His Val Ala
305                 310                 315                 320

His His Leu Phe Ser Thr Met Pro His Tyr His Ala Met Glu Ala Thr
                325                 330                 335

Lys Ala Ile Lys Pro Ile Leu Gly Glu Tyr Tyr His Phe Asp Glu Thr
            340                 345                 350

Pro Ile Tyr Lys Ala Met Trp Arg Glu Ala Lys Glu Cys Met Tyr Val
        355                 360                 365

Glu Pro Asp Lys Gly Ser Asn Gly Lys Gly Val Tyr Trp Tyr Asn Asn
        370                 375                 380

Lys Leu
385

<210> SEQ ID NO 27
<211> LENGTH: 2000
<212> TYPE: DNA
<213> ORGANISM: Glycine max

<400> SEQUENCE: 27

```
ccttaaaccc aatggttgat agagattttt ctccaacatc tctgttgata actaattagc     60
ttgtgatctt tcttatctac taatacaaac tacactaatg ttctcacgc atcctcaact    120
catggccaaa taaaccctcg tagtcacaat tcctctactt ctactgaccc tccaaacaac    180
aacactcaat ggggtaatgt ctctcactca gtccctgcat gccagtattg tggtcgttgt    240
gaccacactg ccaaaacatg ttacaagctg catggtattg gaccccctct gatcatcatc    300
tctactaagc aaatatgtca caacatgata acagttctga tcccaattgg ttgcttgatt    360
tgtgatcttg gaaatttatc cgtctctttt ttcaacactc tggctccacc tctatacttt    420
ggcatggtat attttggta gcactagaaa tctcacttct ccaacttgca atcagccttt    480
aaataataca tactgttggt gtatcatttt taagattccc tatcatggaa ttggtggatc    540
gtacgtctac ttgattttag gtctctcaat tcctagtcaa aattagtctc aatcattatg    600
ctttaaaaat gatgattttg acacttggga gataacaata tttcttaaag tttgattctc    660
aagtttgtat atatgaaata gtgtgttggg agaagtaaac tcttaaaata aatttttata    720
ttttagagat gattctctca ttcttatgaa ggagatatac tagaaaaaaa tgattttat     780
ttttttatt tttattatga aacttaagaa ttaagatacc aggatgaggg acaaaagtca    840
ttaattatta aaaaaaaaat acaagaatca agattattat tttaaaata taaaaaaac     900
taattttgat atataaagaa atccaggga taatacac attctatcca aatattttgt     960
taaaccccag gggcacaatg tttcgtcttt cctcaacagt tataaattgc taatgatatt   1020
atttgtcttg aattggttcc tgtggctagc atatctctgc aacttgtgca accatttggt   1080
aattcaatta agaatatata atatacttta aattactag gatgcataaa aaaccctgtg   1140
acttgtctga ccaagacttg ccaaattttt ttatcatgca ttacaaaaac cagccattg    1200
ttttatttt ttggatttct attctttcca aatgaaggcc taacagataa attgcatgtc   1260
taatttcccc ttgttattag agaaataaga aattataagc ttttgctttg actttgaac    1320
atattttaca ctctttgcag gttgcttttt atcttggaag accagaggag ttcaaaataa   1380
cagtgtcgcg gtaagtaatt gctcgtacat ttccttggta attaggtctc ttattgcgta   1440
ttgttgccat catttttgag gccttgtctg gcttgcatca caattgaaag aaattagttt   1500
gatggttaaa atggtatacc ttttgtcttc attattactc gaattacatt tagaaagacc   1560
tattaataat tacttatttg agtttatcat atcacataaa tacttattta aacgtctggg   1620
agagtattgt acgaaagtaa cataagaatt gacttaaaag ttaaatactt ttggttgaat   1680
atgtttgtca tttgatatag aagagagaaa gaaaatatct gtcaattaaa caatttatta   1740
gtaaattttt ttttgtagca ttccattttt atttttttt tggaattgtt tgcacaatgt   1800
ttcgtctttc cccaacagtt ataaattgct aatgatatta tttgtcttga attggtttgg   1860
```

```
aatgtttaaa tgtgcaccct aagtttgaaa tgtgattcat ttgcgacctc accatagcct    1920
tctacctcta ttatgttgcc acccattact tccacctcct tcccagccct ctctctttct    1980
tggcatggcc aatctactag                                                2000
```

```
<210> SEQ ID NO 28
<211> LENGTH: 882
<212> TYPE: DNA
<213> ORGANISM: Glycine max
<220> FEATURE:
<221> NAME/KEY: mutation
<222> LOCATION: (61)..(61)
<223> OTHER INFORMATION: Sequence can be mutated from G to A.
<220> FEATURE:
<221> NAME/KEY: mutation
<222> LOCATION: (166)..(166)
<223> OTHER INFORMATION: Sequence can be mutated from T to A.
<220> FEATURE:
<221> NAME/KEY: mutation
<222> LOCATION: (167)..(167)
<223> OTHER INFORMATION: Sequence can be mutated from C to T.
<220> FEATURE:
<221> NAME/KEY: mutation
<222> LOCATION: (328)..(328)
<223> OTHER INFORMATION: Sequence can be mutated from G to A.
<220> FEATURE:
<221> NAME/KEY: mutation
<222> LOCATION: (329)..(329)
<223> OTHER INFORMATION: Sequence can be mutated from G to A.
<220> FEATURE:
<221> NAME/KEY: mutation
<222> LOCATION: (334)..(334)
<223> OTHER INFORMATION: Sequence can be mutated from C to T.
<220> FEATURE:
<221> NAME/KEY: mutation
<222> LOCATION: (350)..(350)
<223> OTHER INFORMATION: Sequence can be mutated from C to T.
<220> FEATURE:
<221> NAME/KEY: mutation
<222> LOCATION: (397)..(397)
<223> OTHER INFORMATION: Sequence can be mutated from C to T.
<220> FEATURE:
<221> NAME/KEY: mutation
<222> LOCATION: (502)..(502)
<223> OTHER INFORMATION: Sequence can be mutated from C to T.
<220> FEATURE:
<221> NAME/KEY: mutation
<222> LOCATION: (595)..(595)
<223> OTHER INFORMATION: Sequence can be mutated from T to A.
<220> FEATURE:
<221> NAME/KEY: mutation
<222> LOCATION: (605)..(605)
<223> OTHER INFORMATION: Sequence can be mutated from G to A.
<220> FEATURE:
<221> NAME/KEY: mutation
<222> LOCATION: (626)..(626)
<223> OTHER INFORMATION: Sequence can be mutated from G to A.
<220> FEATURE:
<221> NAME/KEY: mutation
<222> LOCATION: (628)..(628)
<223> OTHER INFORMATION: Sequence can be mutated from G to A.
<220> FEATURE:
<221> NAME/KEY: mutation
<222> LOCATION: (706)..(706)
<223> OTHER INFORMATION: Sequence can be mutated from C to T.
<220> FEATURE:
<221> NAME/KEY: mutation
<222> LOCATION: (721)..(721)
<223> OTHER INFORMATION: Sequence can be mutated from G to A.
<220> FEATURE:
<221> NAME/KEY: mutation
<222> LOCATION: (751)..(751)
<223> OTHER INFORMATION: Sequence can be mutated from G to A.
<220> FEATURE:
<221> NAME/KEY: mutation
<222> LOCATION: (754)..(754)
<223> OTHER INFORMATION: Sequence can be mutated from G to A.
```

```
<220> FEATURE:
<221> NAME/KEY: mutation
<222> LOCATION: (803)..(803)
<223> OTHER INFORMATION: Sequence can be mutated from A to T.
<220> FEATURE:
<221> NAME/KEY: mutation
<222> LOCATION: (829)..(829)
<223> OTHER INFORMATION: Sequence can be mutated from C to T.

<400> SEQUENCE: 28
gctgtccaag gttgcatcct tactggagtt tgggtcattg cccatgagtg tggccaccat      60
gcattcagtg actaccagtt gcttgatgat attttggcc ttgtcctcca ctccggtctc     120
ctagtcccat acttttcatg gaaatacagc catcgccgtc accactccaa cactggttct     180
cttgagcgag atgaagtatt tgtgccaaag cagaagtcct gtatcaagtg gtactctaaa     240
taccttaaca atcctccagg cagagtcctc actcttgctg tcaccctcac acttggttgg     300
cccttgtact tggctttaaa tgtttctgga aggccttatg atagatttgc ttaccactat     360
gacccatatg gtcccattta ctctgatcgt gaacgacttc aaatatatat atcagatgca     420
ggagtacttg cagtatgcta tggccttttc cgtcttgcca tggcaaaagg acttgcctgg     480
gtggtgtgtg tttatggagt tccattgcta gtggtcaatg ggttttcggt gttgattaca     540
ttcttgcagc atactcaacc tgcattgcca cattacactt cctctgagtg ggactggttg     600
agaggagctt tagcaacagt ggatagagat tatggaatcc tgaacaaggt cttccacaat     660
attacagaca ctcatgtagc acatcacttg ttctccacaa tgccacatta tcatgcaatg     720
gaggctacaa aggcaataaa acccattttg ggagagtatt atcggtttga tgagactcca     780
tttgtcaagg caatgtggag agaggcaaga gagtgtattt atgtggagcc agatcaaagt     840
accgagagca aggtgtatat ttggtacaac aataagttgt ga                       882

<210> SEQ ID NO 29
<211> LENGTH: 293
<212> TYPE: PRT
<213> ORGANISM: Glycine max
<220> FEATURE:
<221> NAME/KEY: mutagen
<222> LOCATION: (21)..(21)
<223> OTHER INFORMATION: Sequence can be mutated from Ala to Thr.
<220> FEATURE:
<221> NAME/KEY: mutagen
<222> LOCATION: (56)..(56)
<223> OTHER INFORMATION: Sequence can be mutated from Ser to Phe or Thr.
<220> FEATURE:
<221> NAME/KEY: mutagen
<222> LOCATION: (110)..(110)
<223> OTHER INFORMATION: Sequence can be mutated from Gly to Glu or Arg.
<220> FEATURE:
<221> NAME/KEY: mutagen
<222> LOCATION: (112)..(112)
<223> OTHER INFORMATION: Sequence can be mutated from Pro to Ser.
<220> FEATURE:
<221> NAME/KEY: mutagen
<222> LOCATION: (117)..(117)
<223> OTHER INFORMATION: Sequence can be mutated from Ala to Val.
<220> FEATURE:
<221> NAME/KEY: mutagen
<222> LOCATION: (133)..(133)
<223> OTHER INFORMATION: Sequence can be mutated from Leu to Phe.
<220> FEATURE:
<221> NAME/KEY: mutagen
<222> LOCATION: (168)..(168)
<223> OTHER INFORMATION: Sequence can be mutated from Pro to Ser.
<220> FEATURE:
<221> NAME/KEY: mutagen
<222> LOCATION: (199)..(199)
<223> OTHER INFORMATION: Sequence can be mutated from Trp to Arg.
<220> FEATURE:
```

```
<221> NAME/KEY: mutagen
<222> LOCATION: (202)..(202)
<223> OTHER INFORMATION: Sequence can be mutated from Gly to Glu.
<220> FEATURE:
<221> NAME/KEY: mutagen
<222> LOCATION: (209)..(209)
<223> OTHER INFORMATION: Sequence can be mutated from Arg to Lys.
<220> FEATURE:
<221> NAME/KEY: mutagen
<222> LOCATION: (210)..(210)
<223> OTHER INFORMATION: Sequence can be mutated from Asp to Asn.
<220> FEATURE:
<221> NAME/KEY: mutagen
<222> LOCATION: (236)..(236)
<223> OTHER INFORMATION: Sequence can be mutated from His to Tyr.
<220> FEATURE:
<221> NAME/KEY: mutagen
<222> LOCATION: (241)..(241)
<223> OTHER INFORMATION: Sequence can be mutated from Glu to Lys.
<220> FEATURE:
<221> NAME/KEY: mutagen
<222> LOCATION: (251)..(251)
<223> OTHER INFORMATION: Sequence can be mutated from Gly to Arg.
<220> FEATURE:
<221> NAME/KEY: mutagen
<222> LOCATION: (252)..(252)
<223> OTHER INFORMATION: Sequence can be mutated from Glu to Lys.
<220> FEATURE:
<221> NAME/KEY: mutagen
<222> LOCATION: (268)..(268)
<223> OTHER INFORMATION: Sequence can be mutated from Glu to Val.
<220> FEATURE:
<221> NAME/KEY: mutagen
<222> LOCATION: (277)..(277)
<223> OTHER INFORMATION: Sequence can be mutated from Pro to Ser.

<400> SEQUENCE: 29

Ala Val Gln Gly Cys Ile Leu Thr Gly Val Trp Val Ile Ala His Glu
1               5                   10                  15

Cys Gly His His Ala Phe Ser Asp Tyr Gln Leu Leu Asp Asp Ile Phe
            20                  25                  30

Gly Leu Val Leu His Ser Gly Leu Leu Val Pro Tyr Phe Ser Trp Lys
        35                  40                  45

Tyr Ser His Arg Arg His His Ser Asn Thr Gly Ser Leu Glu Arg Asp
    50                  55                  60

Glu Val Phe Val Pro Lys Gln Lys Ser Cys Ile Lys Trp Tyr Ser Lys
65                  70                  75                  80

Tyr Leu Asn Asn Pro Pro Gly Arg Val Leu Thr Leu Ala Val Thr Leu
                85                  90                  95

Thr Leu Gly Trp Pro Leu Tyr Leu Ala Leu Asn Val Ser Gly Arg Pro
            100                 105                 110

Tyr Asp Arg Phe Ala Tyr His Tyr Asp Pro Tyr Gly Pro Ile Tyr Ser
        115                 120                 125

Asp Arg Glu Arg Leu Gln Ile Tyr Ile Ser Asp Ala Gly Val Leu Ala
    130                 135                 140

Val Cys Tyr Gly Leu Phe Arg Leu Ala Met Ala Lys Gly Leu Ala Trp
145                 150                 155                 160

Val Val Cys Val Tyr Gly Val Pro Leu Leu Val Val Asn Gly Phe Ser
                165                 170                 175

Val Leu Ile Thr Phe Leu Gln His Thr Gln Pro Ala Leu Pro His Tyr
            180                 185                 190

Thr Ser Ser Glu Trp Asp Trp Leu Arg Gly Ala Leu Ala Thr Val Asp
        195                 200                 205

Arg Asp Tyr Gly Ile Leu Asn Lys Val Phe His Asn Ile Thr Asp Thr
    210                 215                 220
```

```
His Val Ala His His Leu Phe Ser Thr Met Pro His Tyr His Ala Met
225                 230                 235                 240

Glu Ala Thr Lys Ala Ile Lys Pro Ile Leu Gly Glu Tyr Tyr Arg Phe
                245                 250                 255

Asp Glu Thr Pro Phe Val Lys Ala Met Trp Arg Glu Ala Arg Glu Cys
            260                 265                 270

Ile Tyr Val Glu Pro Asp Gln Ser Thr Glu Ser Lys Gly Val Phe Trp
        275                 280                 285

Tyr Asn Asn Lys Leu
    290
```